United States Patent
Sun et al.

(10) Patent No.: US 12,226,491 B2
(45) Date of Patent: Feb. 18, 2025

(54) NANO-SATELLITE COMPLEXES

(71) Applicant: The Regents of the University of Michigan, Ann Arbor, MI (US)

(72) Inventors: Duxin Sun, Ann Arbor, MI (US); Ryan Clauson, Ann Arbor, MI (US); Hongwei Chen, Ann Arbor, MI (US); Chengyi Li, Ann Arbor, MI (US); Wei Gao, Ann Arbor, MI (US); Luke Bugada, Ann Arbor, MI (US); Fei Wen, Ann Arbor, MI (US); Brett Hill, Ann Arbor, MI (US); Syed Monem Rizvi, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 935 days.

(21) Appl. No.: 17/232,751

(22) Filed: Apr. 16, 2021

(65) Prior Publication Data

US 2021/0346478 A1 Nov. 11, 2021

Related U.S. Application Data

(63) Continuation-in-part of application No. PCT/US2019/056765, filed on Oct. 17, 2019.

(60) Provisional application No. 62/746,755, filed on Oct. 17, 2018.

(51) Int. Cl.
| | |
|---|---|
| *A61K 47/69* | (2017.01) |
| *A61K 9/16* | (2006.01) |
| *A61K 38/19* | (2006.01) |
| *A61K 39/00* | (2006.01) |
| *A61K 39/295* | (2006.01) |
| *A61K 39/39* | (2006.01) |
| *A61K 45/06* | (2006.01) |
| *A61K 47/02* | (2006.01) |
| *A61K 47/64* | (2017.01) |
| *A61P 35/00* | (2006.01) |

(52) U.S. Cl.
CPC .......... *A61K 47/6929* (2017.08); *A61K 9/167* (2013.01); *A61K 38/191* (2013.01); *A61K 39/0011* (2013.01); *A61K 39/001106* (2018.08); *A61K 39/295* (2013.01); *A61K 39/39* (2013.01); *A61K 39/4611* (2023.05); *A61K 39/4612* (2023.05); *A61K 39/4622* (2023.05); *A61K 39/464406* (2023.05); *A61K 45/06* (2013.01); *A61K 47/02* (2013.01); *A61K 47/646* (2017.08); *A61P 35/00* (2018.01); *A61K 2039/60* (2013.01); *A61K 2039/627* (2013.01); *A61K 2039/64* (2013.01); *A61K 2239/49* (2023.05)

(58) Field of Classification Search
None
See application file for complete search history.

(56) References Cited

U.S. PATENT DOCUMENTS

| | | |
|---|---|---|
| 2014/0086828 A1 | 3/2014 | Foster et al. |
| 2015/0065858 A1 | 3/2015 | Chen et al. |

OTHER PUBLICATIONS

Fan and Moon, Vaccine, 2015, 3:662-685 (Year: 2015).*
Skeate et al., Front Immunol., published online May 15, 2020, vol. 11, Article 922, 11 pages (Year: 2020).*
International Search Report and Written Opinion for PCT/US19/56765. Mailed Mar. 3, 2020. 15 pages.
Bachmann et al., The influence of antigen organization on B cell responsiveness. Science. Nov. 26, 1993;262(5138):1448-51.
Bachmann et al., Vaccine delivery: a matter of size, geometry, kinetics and molecular patterns. Nat Rev Immunol. Nov. 2010;10(11):787-96.
Balmelli et al., Nasal immunization of mice with human papillomavirus type 16 virus-like particles elicits neutralizing antibodies in mucosal secretions. J Virol. Oct. 1998;72(10):8220-9.
Beachler et al., Multisite HPV16/18 Vaccine Efficacy Against Cervical, Anal, and Oral HPV Infection. J Natl Cancer Inst. Oct. 14, 2015;108(1):djv302. 1-8.
Bekaii-Saab et al., Phase I Immunotherapy Trial with Two Chimeric HER-2 B-Cell Peptide Vaccines Emulsified in Montanide ISA 720VG and Nor-MDP Adjuvant in Patients with Advanced Solid Tumors. Clin Cancer Res. Jun. 15, 2019;25(12):3495-3507.

(Continued)

*Primary Examiner* — Stacy B Chen
(74) *Attorney, Agent, or Firm* — Jason R. Bond; Casimir Jones, S.C.

(57) ABSTRACT

The present invention provides, in some embodiments, methods, compositions, systems, and kits comprising nano-satellite complexes comprising: a core nanoparticle complex comprising a biocompatible coating surrounding a nanoparticle core; 3-25 satellite particles attached to, or absorbed to, said biocompatible coating; a plurality of antigenic peptides conjugated to, or absorbed to, said satellite particles; and at least one additional property. In other embodiments, provided herein are nano-satellite complexes comprising: a core nanoparticle complex comprising a biocompatible coating surrounding a nanoparticle core; a plurality of satellite particles attached to, or absorbed to, said biocompatible coating; a plurality of antigenic peptides conjugated to, or absorbed to, said satellite particles; and a plurality of LIGHT (TNFSF14) peptides conjugated to, or absorbed to, said satellite particles. In some embodiments, administration of the nanosatellite complexes to a subject with cancer achieves long-term cancer remission (e.g., when combined with an immune checkpoint inhibitor, such as αPD1).

9 Claims, 20 Drawing Sheets
(17 of 20 Drawing Sheet(s) Filed in Color)
Specification includes a Sequence Listing.

(56) References Cited

OTHER PUBLICATIONS

Benavides et al., The impact of HER2/neu expression level on response to the E75 vaccine: from U.S. Military Cancer Institute Clinical Trials Group Study I-01 and I-02. Clin Cancer Res. Apr. 15, 2009;15(8):2895-904.
Billi et al., The female-biased factor VGLL3 drives cutaneous and systemic autoimmunity. JCI Insight. Apr. 18, 2019;4(8):e127291.
Brink et al., Visualizing the effects of antigen affinity on T-dependent B-cell differentiation. Immunol Cell Biol. Jan. 2008;86(1):31-9.
Cabrita et al., Tertiary lymphoid structures improve immunotherapy and survival in melanoma. Nature. Jan. 2020;577(7791):561-565.
Carrasco et al., B cells acquire particulate antigen in a macrophage-rich area at the boundary between the follicle and the subcapsular sinus of the lymph node. Immunity. Jul. 2007;27(1):160-71.
Carter et al., Humanization of an anti-p185HER2 antibody for human cancer therapy. Proc Natl Acad Sci U S A. May 15, 1992;89(10):4285-9.
Cascalho et al., A quasi-monoclonal mouse. Science. Jun. 14, 1996;272(5268):1649-52.
Chackerian et al., Conjugation of a self-antigen to papillomavirus-like particles allows for efficient induction of protective autoantibodies. J Clin Invest. Aug. 2001;108(3):415-23.
Chang et al., Safety and tolerability of chikungunya virus-like particle vaccine in healthy adults: a phase 1 dose-escalation trial. Lancet. Dec. 6, 2014;384(9959):2046-52.
Chattopadhyay et al., Nanoparticle Vaccines Adopting Virus-like Features for Enhanced Immune Potentiation. Nanotheranostics. Jun. 9, 2017;1(3):244-260.
Chen et al., Facile Fabrication of Near-Infrared-Resonant and Magnetic Resonance Imaging-Capable Nanomediators for Photothermal Therapy. ACS Appl Mater Interfaces. Jun. 17, 2015;7(23):12814-23.
Chen et al., Highly crystallized iron oxide nanoparticles as effective and biodegradable mediators for photothermal cancer therapy. J Mater Chem B. Feb. 21, 2014;2(7):757-765.
Chen et al., Uhrf1 regulates germinal center B cell expansion and affinity maturation to control viral infection. J Exp Med. May 7, 2018;215(5):1437-1448.
Chen et al., Nanobiomaterial-based vaccination immunotherapy of cancer. Biomaterials. Mar. 2021;270:120709. 1-26.
Cheng. The Density Code for the Development of a Vaccine? J Pharm Sci. Nov. 2016;105(11):3223-3232.
Chertok et al., Comparison of electron spin resonance spectroscopy and inductively-coupled plasma optical emission spectroscopy for biodistribution analysis of iron-oxide nanoparticles. Mol Pharm. Apr. 5, 2010;7(2):375-85.
Chevrier et al., An Immune Atlas of Clear Cell Renal Cell Carcinoma. Cell. May 4, 2017;169(4):736-749.e18.
Clauson et al., Size-Controlled Iron Oxide Nanoplatforms with Lipidoid-Stabilized Shells for Efficient Magnetic Resonance Imaging-Trackable Lymph Node Targeting and High-Capacity Biomolecule Display. ACS Appl Mater Interfaces. Jun. 20, 2018;10(24):20281-20295.
Costa et al., The clinical development of vaccines for HER2+ breast cancer: Current landscape and future perspectives. Cancer Treat Rev. Dec. 2017;61:107-115.
Crowe et al., Select human anthrax protective antigen epitope-specific antibodies provide protection from lethal toxin challenge. J Infect Dis. Jul. 15, 2010;202(2):251-60.
Cubas et al., Virus-like particle (VLP) lymphatic trafficking and immune response generation after immunization by different routes. J Immunother. Feb.-Mar. 2009;32(2):118-28.
De Silva et al., Dynamics of B cells in germinal centres. Nat Rev Immunol. Mar. 2015;15(3):137-48.
Disis et al., Concurrent trastuzumab and HER2/neu-specific vaccination in patients with metastatic breast cancer. J Clin Oncol. Oct. 1, 2009;27(28):4685-92.

Elsayed et al., Intrastructural Help: Harnessing T Helper Cells Induced by Licensed Vaccines for Improvement of HIV Env Antibody Responses to Virus-Like Particle Vaccines. J Virol. Jun. 29, 2018;92(14):e00141-18.
Fleige et al., IL-17-induced CXCL12 recruits B cells and induces follicle formation in BALT in the absence of differentiated FDCs. J Exp Med. Apr. 7, 2014;211(4):643-51.
Forsell et al., Regulation of Subunit-Specific Germinal Center B Cell Responses to the HIV-1 Envelope Glycoproteins by Antibody-Mediated Feedback. Front Immunol. Jun. 30, 2017;8:738. 1-9.
Franklin et al., Insights into ErbB signaling from the structure of the ErbB2-pertuzumab complex. Cancer Cell. Apr. 2004;5(4):317-28.
Franz et al., Ex vivo characterization and isolation of rare memory B cells with antigen tetramers. Blood. Jul. 14, 2011;118(2):348-57.
Fridman et al., B cells and cancer: To B or not to B? J Exp Med. Jan. 4, 2021;218(1):e20200851. 1-11.
Fries et al., Advances in nanomaterial vaccine strategies to address infectious diseases impacting global health. Nat Nanotechnol. Apr. 2021;16(4):1-14.
Fuenmayor et al., Production of virus-like particles for vaccines. N Biotechnol. Oct. 25, 2017;39(Pt B):174-180.
Furtado et al., Lymphotoxin beta receptor signaling is required for inflammatory lymphangiogenesis in the thyroid. Proc Natl Acad Sci U S A. Mar. 20, 2007;104(12):5026-31.
Galluzzi et al., Heavy Metal to Rock the Immune Infiltrate. Trends Immunol. Aug. 2017;38(8):539-541.
Garaud et al., Tumor infiltrating B-cells signal functional humoral immune responses in breast cancer. JCI Insight. Aug. 13, 2019;5(18):e129641. 1-20.
Gobin et al., Near-infrared-resonant gold/gold sulfide nanoparticles as a photothermal cancer therapeutic agent. Small. Mar. 22, 2010;6(6):745-52.
Gomes et al., Harnessing Nanoparticles for Immunomodulation and Vaccines. Vaccines (Basel). Feb. 14, 2017;5(1):6.
Gray et al., Lymph node macrophages. J Innate Immun. 2012;4(5-6):424-36.
Guedj et al., M1 macrophages act as LTβR-independent lymphoid tissue inducer cells during atherosclerosis-related lymphoid neogenesis. Cardiovasc Res. Mar. 1, 2014;101(3):434-43.
Guo et al., The Role of Tumor-Infiltrating B Cells in Tumor Immunity. J Oncol. Sep. 24, 2019;2019:2592419. 1-9.
Hailemichael et al., Persistent antigen at vaccination sites induces tumor-specific CD8+ T cell sequestration, dysfunction and deletion. Nat Med. Apr. 2013;19(4):465-72.
Helmink et al., B cells and tertiary lymphoid structures promote immunotherapy response. Nature. Jan. 2020;577(7791):549-555.
Hill et al., Engineering Virus-like Particles for Antigen and Drug Delivery. Curr Protein Pept Sci. 2018;19(1):112-127.
Hinton et al., Pattern recognition by B cells: the role of antigen repetitiveness versus Toll-like receptors. Curr Top Microbiol Immunol. 2008;319:1-15.
Hladikova et al., Tumor-infiltrating B cells affect the progression of oropharyngeal squamous cell carcinoma via cell-to-cell interactions with CD8+ T cells. J Immunother Cancer. Oct. 17, 2019;7(1):261. 1-16.
Hollern et al., B Cells and T Follicular Helper Cells Mediate Response to Checkpoint Inhibitors in High Mutation Burden Mouse Models of Breast Cancer. Cell. Nov. 14, 2019;179(5):1191-1206. e21.
Ingale et al., High-Density Array of Well-Ordered HIV-1 Spikes on Synthetic Liposomal Nanoparticles Efficiently Activate B Cells. Cell Rep. May 31, 2016; 15(9):1986-99.
Iwasaki et al., Why and How Vaccines Work. Cell. Oct. 15, 2020;183(2):290-295.
Jasinska et al., Inhibition of tumor cell growth by antibodies induced after vaccination with peptides derived from the extracellular domain of Her-2/neu. Int J Cancer. Dec. 20, 2003;107(6):976-83.
Jegerlehner et al., Carrier induced epitopic suppression of antibody responses induced by virus-like particles is a dynamic phenomenon caused by carrier-specific antibodies. Vaccine. Jul. 26, 2010;28(33):5503-12.

(56) References Cited

OTHER PUBLICATIONS

Johansson-Percival et al., De novo induction of intratumoral lymphoid structures and vessel normalization enhances immunotherapy in resistant tumors. Nat Immunol. Nov. 2017;18(11):1207-1217.

Junt et al., Subcapsular sinus macrophages in lymph nodes clear lymph-borne viruses and present them to antiviral B cells. Nature. Nov. 1, 2007;450(7166):110-4.

Kamala. Hock immunization: a humane alternative to mouse footpad injections. J Immunol Methods. Dec. 1, 2007;328(1-2):204-14.

Kaumaya. B-cell epitope peptide cancer vaccines: a new paradigm for combination immunotherapies with novel checkpoint peptide vaccine. Future Oncol. Aug. 2020;16(23):1767-1791.

Kenter et al., Phase I immunotherapeutic trial with long peptides spanning the E6 and E7 sequences of high-risk human papillomavirus 16 in end-stage cervical cancer patients shows low toxicity and robust immunogenicity. Clin Cancer Res. Jan. 1, 2008;14(1):169-77.

Kenter et al., Vaccination against HPV-16 oncoproteins for vulvar intraepithelial neoplasia. N Engl J Med. Nov. 5, 2009;361(19):1838-47.

Kokate et al., One pot synthesis of magnetite-silica nanocomposites: applications as tags, entrapment matrix and in water purification. J Mater Chem A, 2013; 1(6), 2022-2029.

Kroeger et al., Tumor-Infiltrating Plasma Cells are Associated with Tertiary Lymphoid Structures, Cytolytic T-Cell Responses, and Superior Prognosis in Ovarian Cancer. Clin Cancer Res. Jun. 15, 2016;22(12):3005-15.

Kuai et al., Designer vaccine nanodiscs for personalized cancer immunotherapy. Nat Mater. Apr. 2017; 16(4):489-496.

Kuka et al., The role of lymph node sinus macrophages in host defense. Ann N Y Acad Sci. Jun. 2014;1319:38-46.

Landry et al., Preclinical and clinical development of plant-made virus-like particle vaccine against avian H5N1 influenza. PLoS One. Dec. 22, 2010;5(12):e15559. 1-12.

Lavin et al., Innate Immune Landscape in Early Lung Adenocarcinoma by Paired Single-Cell Analyses. Cell. May 4, 2017;169(4):750-765. e17.

Lee et al., Intranasal vaccination with M2e5x virus-like particles induces humoral and cellular immune responses conferring cross-protection against heterosubtypic influenza viruses. PLoS One. Jan. 11, 2018;13(1):e0190868. 1-15.

Lee et al., Rabies Virus-Inspired Silica-Coated Gold Nanorods as a Photothermal Therapeutic Platform for Treating Brain Tumors. Adv Mater. Apr. 2017;29(13). 1-8.

Lee et al., Virus-mimetic polymer nanoparticles displaying hemagglutinin as an adjuvant-free influenza vaccine. Biomaterials. Nov. 2018;183:234-242.

Lee et al., Antibody Production with Synthetic Peptides. Methods Mol Biol. 2016;1474:25-47.

Lochner et al., Microbiota-induced tertiary lymphoid tissues aggravate inflammatory disease in the absence of RORgamma t and LTi cells. J Exp Med. Jan. 17, 2011;208(1):125-34.

Loo et al., Lymphatic Vessels Balance Viral Dissemination and Immune Activation following Cutaneous Viral Infection. Cell Rep. Sep. 26, 2017;20(13):3176-3187.

Lowenfeld et al., Dendritic Cell Vaccination Enhances Immune Responses and Induces Regression of HER2pos DCIS Independent of Route: Results of Randomized Selection Design Trial. Clin Cancer Res. Jun. 15, 2017;23(12):2961-2971.

Lu et al., Determination of the concentration and the average number of gold atoms in a gold nanoparticle by osmotic pressure. Langmuir. Jun. 26, 2012;28(25):9282-7.

Lu et al., Role of the Lymphotoxin/LIGHT System in the Development and Maintenance of Reticular Networks and Vasculature in Lymphoid Tissues. Front Immunol. Feb. 11, 2014;5:47. 1-15.

Lu et al., Complement Signals Determine Opposite Effects of B Cells in Chemotherapy-Induced Immunity. Cell. Mar. 19, 2020;180(6):1081-1097.e24.

Masavuli et al., Preclinical Development and Production of Virus-Like Particles as Vaccine Candidates for Hepatitis C. Front Microbiol. Dec. 5, 2017;8:2413. 1-11.

McCluskie et al., The effect of preexisting anti-carrier immunity on subsequent responses to CRM197 or Qb-VLP conjugate vaccines. Immunopharmacol Immunotoxicol. Jun. 2016;38(3):184-96.

McHeyzer-Williams et al., Antigen-specific memory B cell development. Annu Rev Immunol. 2005;23:487-513.

McHeyzer-Williams et al., Molecular programming of B cell memory. Nat Rev Immunol. Dec. 9, 2011;12(1):24-34.

Melero et al., Therapeutic vaccines for cancer: an overview of clinical trials. Nat Rev Clin Oncol. Sep. 2014;11(9):509-24.

Mingueneau et al., Single-cell mass cytometry of TCR signaling: amplification of small initial differences results in low ERK activation in NOD mice. Proc Natl Acad Sci U S A. Nov. 18, 2014;111(46):16466-71.

Minor. Live attenuated vaccines: Historical successes and current challenges. Virology. May 2015;479-480:379-92.

Mittendorf, et al., Final report of the phase I/II clinical trial of the E75 (nelipepimut-S) vaccine with booster inoculations to prevent disease recurrence in high-risk breast cancer patients. Ann Oncol. Sep. 2014;25(9):1735-1742.

Mittendorf et al., Primary analysis of a prospective, randomized, single-blinded phase II trial evaluating the HER2 peptide AE37 vaccine in breast cancer patients to prevent recurrence. Ann Oncol. Jul. 2016;27(7):1241-8.

Miyako et al., Antitumor effect of new HER2 peptide vaccination based on B cell epitope. Anticancer Res. Oct. 2011;31(10):3361-8.

Mohsen et al., Interaction of Viral Capsid-Derived Virus-Like Particles (VLPs) with the Innate Immune System. Vaccines (Basel). Jul. 2, 2018;6(3):37. 1-12.

Mohsen et al., Major findings and recent advances in virus-like particle (VLP)-based vaccines. Semin Immunol. Dec. 2017;34:123-132.

Munoz-Erazo et al., Tertiary lymphoid structures in cancer—considerations for patient prognosis. Cell Mol Immunol. Jun. 2020;17(6):570-575.

Nayerossadat et al., Viral and nonviral delivery systems for gene delivery. Adv Biomed Res. 2012;1:27. 1-11.

Nguyen et al., Sequential B-cell epitopes of Bacillus anthracis lethal factor bind lethal toxin-neutralizing antibodies. Infect Immun. Jan. 2009;77(1):162-9.

Ni et al., Tumor-infiltrating B cell is associated with the control of progression of gastric cancer. Immunol Res. Feb. 2021;69(1):43-52.

Ocana et al., Dual targeting of HER2-positive breast cancer with trastuzumab emtansine and pertuzumab: understanding clinical trial results. Oncotarget. Aug. 7, 2018;9(61):31915-31919.

Olsson et al., Induction of immune memory following administration of a prophylactic quadrivalent human papillomavirus (HPV) types 6/11/16/18 L1 virus-like particle (VLP) vaccine. Vaccine. Jun. 21, 2007;25(26):4931-9.

Ong et al., Virus like particles as a platform for cancer vaccine development. PeerJ. Nov. 15, 2017;5:e4053. 1-31.

Oracki et al., Plasma cell development and survival. Immunol Rev. Sep. 2010;237(1):140-59.

Palladini et al., Virus-like particle display of HER2 induces potent anti-cancer responses. Oncoimmunology. Jan. 5, 2018;7(3):e1408749. 1-12.

Palomares et al., Challenges for the production of virus-like particles in insect cells: The case of rotavirus-like particles. Biochem Eng J, 2009; 45, 158-167.

Pape et al., Different B cell populations mediate early and late memory during an endogenous immune response. Science. Mar. 4, 2011;331(6021):1203-7.

Patel et al., The role of B lymphocytes in the immuno-biology of non-small-cell lung cancer. Cancer Immunol Immunother. Mar. 2020;69(3):325-342.

Peoples et al., Clinical trial results of a HER2/neu (E75) vaccine to prevent recurrence in high-risk breast cancer patients. J Clin Oncol. Oct. 20, 2005;23(30):7536-45.

Peoples et al., Combined clinical trial results of a HER2/neu (E75) vaccine for the prevention of recurrence in high-risk breast cancer

(56) References Cited

OTHER PUBLICATIONS patients: U.S. Military Cancer Institute Clinical Trials Group Study I-01 and I-02. Clin Cancer Res. Feb. 1, 2008;14(3):797-803.
Peters et al., Th17 cells induce ectopic lymphoid follicles in central nervous system tissue inflammation. Immunity. Dec. 23, 2011;35(6):986-96.
Petitprez et al., B cells are associated with survival and immunotherapy response in sarcoma. Nature. Jan. 2020;577(7791):556-560.
Pierce et al., The tipping points in the initiation of B cell signalling: how small changes make big differences. Nat Rev Immunol. Nov. 2010;10(11):767-77.
Plummer et al., Viral nanoparticles and virus-like particles: platforms for contemporary vaccine design. Wiley Interdiscip Rev Nanomed Nanobiotechnol. Mar.-Apr. 2011;3(2):174-196.
Pokorski et al., The art of engineering viral nanoparticles. Mol Pharm. Feb. 7, 2011;8(1):29-43.
Riitho et al., Design and evaluation of the immunogenicity and efficacy of a biomimetic particulate formulation of viral antigens. Sci Rep. Oct. 23, 2017;7(1):13743.
Rockberg et al., Discovery of epitopes for targeting the human epidermal growth factor receptor 2 (HER2) with antibodies. Mol Oncol. Jun. 2009;3(3):238-47.
Rodriguez-Limas et al., Virus-like particles: the future of microbial factories and cell-free systems as platforms for vaccine development. Curr Opin Biotechnol. Dec. 2013;24(6):1089-93.
Roldao et al., Virus-like particles in vaccine development. Expert Rev Vaccines. Oct. 2010;9(10):1149-76.
Roy et al., Virus-like particles as a vaccine delivery system: myths and facts. Hum Vaccin. Jan.-Feb. 2008;4(1):5-12.
Sanchez et al., A general process for the development of peptide-based immunoassays for monoclonal antibodies. Cancer Chemother Pharmacol. Oct. 2010;66(5):919-25.
Schiller et al., Understanding and learning from the success of prophylactic human papillomavirus vaccines. Nat Rev Microbiol. Oct. 2012;10(10):681-92.
Schneble et al., The HER2 peptide nelipepimut-S (E75) vaccine (NeuVax™) in breast cancer patients at risk for recurrence: correlation of immunologic data with clinical response. Immunotherapy. 2014;6(5):519-31.
Shi et al., GARDASIL: prophylactic human papillomavirus vaccine development—from bench top to bed-side. Clin Pharmacol Ther. Feb. 2007;81(2):259-64.
Shtykova et al., Structure and properties of iron oxide nanoparticles encapsulated by phospholipids with poly(ethylene glycol) tails. J Phys Chem C, 2007, 111, 18078-18086.
Shukla et al., Presentation of HER2 epitopes using a filamentous plant virus-based vaccination platform. J Mater Chem B. Oct. 7, 2014;2(37):6249-6258.
Somiya et al., Current Progress of Virus-mimicking Nanocarriers for Drug Delivery. Nanotheranostics. Oct. 31, 2017;1(4):415-429.
Spohn et al., Exploiting viral properties for the rational design of modern vaccines. Expert Rev Vaccines. Feb. 2008;7(1):43-54.
Swain et al., Pertuzumab, trastuzumab, and docetaxel in HER2-positive metastatic breast cancer. N Engl J Med. Feb. 19, 2015;372(8):724-34.
Tam et al., Sustained antigen availability during germinal center initiation enhances antibody responses to vaccination. Proc Natl Acad Sci U S A. Oct. 25, 2016;113(43):E6639-E6648.
Tan et al., Mitigating SOX2-potentiated Immune Escape of Head and Neck Squamous Cell Carcinoma with a STING-inducing Nanosatellite Vaccine. Clin Cancer Res. Sep. 1, 2018;24(17):4242-4255.

Tokatlian et al., Innate immune recognition of glycans targets HIV nanoparticle immunogens to germinal centers. Science. Feb. 8, 2019;363(6427):649-654.
Tong et al., Self-assembly of phospholipid-PEG coating on nanoparticles through dual solvent exchange. Nano Lett. Sep. 14, 2011;11(9):3720-6.
Treanor et al., A novel intramuscular bivalent norovirus virus-like particle vaccine candidate—reactogenicity, safety, and immunogenicity in a phase 1 trial in healthy adults. J Infect Dis. Dec. 1, 2014;210(11):1763-71.
Udenfriend et al., Fluorescamine: a reagent for assay of amino acids, peptides, proteins, and primary amines in the picomole range. Science. Nov. 24, 1972;178(4063):871-2.
Van Der Burg et al., Vaccines for established cancer: overcoming the challenges posed by immune evasion. Nat Rev Cancer. Apr. 2016;16(4):219-33.
Van Loon et al., Enzyme-linked immunosorbent assay for quantitation of toxoplasma antibodies in human sera. J Clin Pathol. Jul. 1980;33(7):635-9.
Van Poelgeest et al., Vaccination against Oncoproteins of HPV16 for Noninvasive Vulvar/Vaginal Lesions: Lesion Clearance is Related to the Strength of the T-Cell Response. Clin Cancer Res. May 15, 2016;22(10):2342-50.
Vanblargan et al., Deconstructing the Antiviral Neutralizing-Antibody Response: Implications for Vaccine Development and Immunity. Microbiol Mol Biol Rev. Oct. 26, 2016;80(4):989-1010.
Veneziano et al., Role of nanoscale antigen organization on B-cell activation probed using DNA origami. Nat Nanotechnol. Aug. 2020;15(8):716-723.
Wang et al., Virus-like particles for the prevention of human papillomavirus-associated malignancies. Expert Rev Vaccines. Feb. 2013;12(2):129-41.
Wang et al., Tumor-infiltrating B cells: their role and application in anti-tumor immunity in lung cancer. Cell Mol Immunol. Jan. 2019;16(1):6-18.
Welters et al., Induction of tumor-specific CD4+ and CD8+ T-cell immunity in cervical cancer patients by a human papillomavirus type 16 E6 and E7 long peptides vaccine. Clin Cancer Res. Jan. 1, 2008;14(1):178-87.
Welters et al., Success or failure of vaccination for HPV16-positive vulvar lesions correlates with kinetics and phenotype of induced T-cell responses. Proc Natl Acad Sci U S A. Jun. 29, 2010;107(26):11895-9.
Welters et al., Vaccination during myeloid cell depletion by cancer chemotherapy fosters robust T cell responses. Sci Transl Med. Apr. 13, 2016;8(334):334ra52. 1-13.
Whittington et al., Her-2 DNA versus cell vaccine: immunogenicity and anti-tumor activity. Cancer Immunol Immunother. May 2009;58(5):759-67.
Wouters et al., Prognostic Significance of Tumor-Infiltrating B Cells and Plasma Cells in Human Cancer. Clin Cancer Res. Dec. 15, 2018;24(24):6125-6135.
Yuen et al., B lymphocytes and cancer: a love-hate relationship. Trends Cancer. Dec. 2016;2(12):747-757.
Zarebski et al., Analysis of epitope information related to Bacillus anthracis and Clostridium botulinum. Expert Rev Vaccines. Feb. 2008;7(1):55-74.
Zeltins. Construction and characterization of virus-like particles: a review. Mol Biotechnol. Jan. 2013;53(1):92-107.
Zhang et al., Landscape of infiltrating B cells and their clinical significance in human hepatocellular carcinoma. Oncoimmunology. Feb. 7, 2019;8(4):e1571388. 1-11.

\* cited by examiner

FIG. 4

```
>Ag000001_ERBB2
MELAALCRWGLLLALLPPGAASTQVCTGTDMKLRLPASPETHLDMLRHLYQGCQVVQGNLELTYLPTNAS
LSFLQDIQEVQGYVLIAHNQVRQVPLQRLRIVRGTQLFEDNYALAVLDNGDPLNNTTPVTGASPGGLREL
QLRSLTEILKGGVLIQRNPQLCYQDTILWKDIFHKNNQLALTLIDTNRSRACHPCSPMCKGSRCWGESSE
DCQSLTRTVCAGGCARCKGPLPTDCCHEQCAAGCTGPKHSDCLACLHFNHSGICELHCPALVTYNTDTFE
SMPNPEGRYTFGASCVTACPYNYLSTDVGSCTLVCPLHNQEVTAEDGTQRCEKCSKPCARVCYGLGMEHL
REVRAVTSANIQEFAGCKKIFGSLAFLPESFDGDPASNTAPLQPEQLQVFETLEEITGYLYISAWPDSLP
DLSVFQNLQVIRGRILHNGAYSLTLQGLGISWLGLRSLRELGSGLALIHHNTHLCFVHTVPWDQLFRNPH
QALLHTANRPEDECVGEGLACHQLCARGHCWGPGPTQCVNCSQFLRGQECVEECRVLQGLPREYVNARHC
LPCHPECQPQNGSVTCFGPEADQCVACAHYRDPPFCVARCPSGVKPDLSYMPIWKFPDEEGACQPCPINC
THSCVDLDDKGCPAEQRASPLTSIISAVVGILLVVVLGVVFGILIKRRQQKIRKYTMRRLLQETELVEPL
TPSGAMPNQAQMRILKETELRKVKVLGSGAFGTVYKGIWIPDGENVKIPVAIKVLRENTSPKANKEILDE
AYVMAGVGSPYVSRLLGICLTSTVQLVTQLMPYGCLLDHVRENRGRLGSQDLLNWCMQIAKGMSYLEDVR
LVHRDLAARNVLVKSPNHVKITDFGLARLLDIDETEYHADGGKVPIKWMALESILRRRFTHQSDVWSYGV
TVWELMTFGAKPYDGIPAREIPDLLEKGERLPQPPICTIDVYMIMVKCWMIDSECRPRFRELVSEFSRMA
RDPQRFVVIQNEDLGPASPLDSTFYRSLLEDDDMGDLVDAEEYLVPQQGFFCPDPAPGAGGMVHHRHRSS
STRSGGGDLTLGLEPSEEEAPRSPLAPSEGAGSDVFDGDLGMGAAKGLQSLPTHDPSPLQRYSEDPTVPL
PSETDGYVAPLTCSPQPEYVNQPDVRPQPPSPREGPLPAARPAGATLERPKTLSPGKNGVVKDVFAFGGA
VENPEYLTPQGGAAPQPHPPPAFSPAFDNLYYWDQDPPERGAPPSTFKGTPTAENPEYLGLDVPV
```

FIG. 10
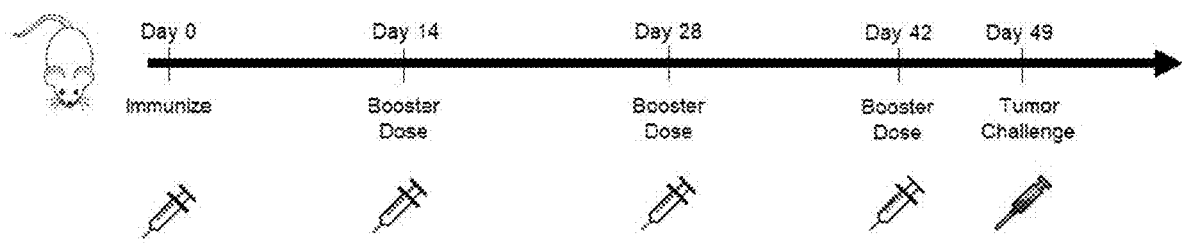
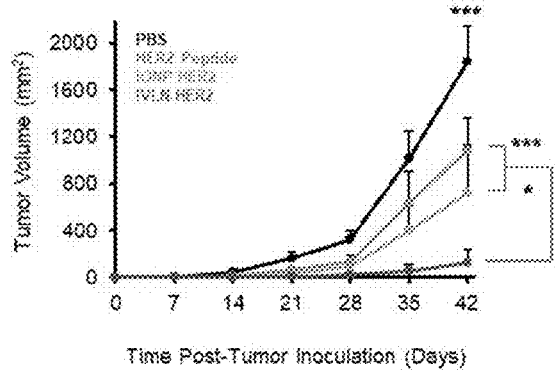
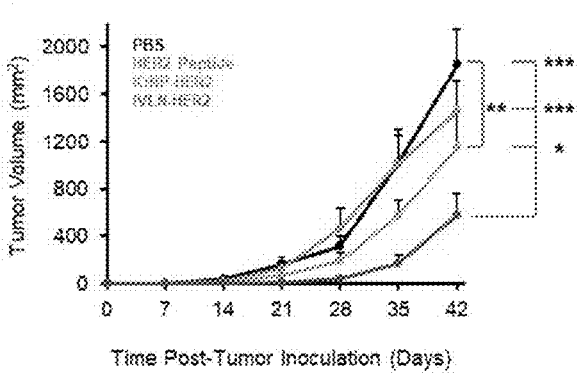

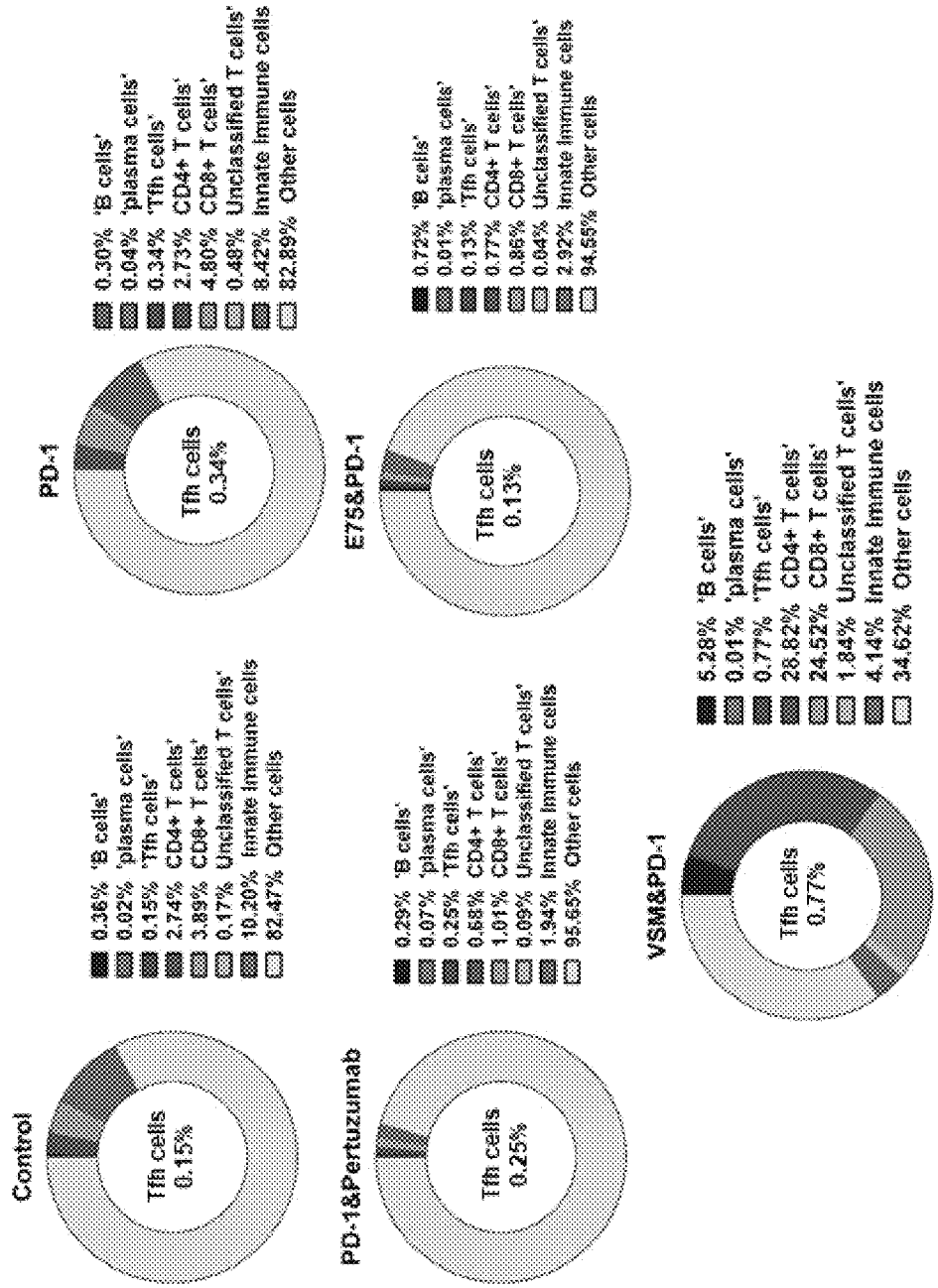

FIG. 16

Exemplary Human LIGHT Peptide Amino Acid Sequence (SEQ ID NO: 5)

```
  1 meesvvrpsv fvvdgqtdip ftrlgrshrr qscsvarvgl glllllmgag lavqgwfllq
 61 lhwrlgemvt rlpdgpagsw eqliqerrsh evnpaahltg anssltgsgg pllwetqlgl
121 aflrglsyhd galvvtkagy yyiyskvqlg gvgcplglas tithglykrt prypeelell
181 vsqqspcgra tsssrvwwds sflggvvhle agekvvvrvl derivrlrdg trsyfgafmv
```

NANO-SATELLITE COMPLEXES

The present application is a continuation-in-part of International Application PCT/US2019/056765 filed Oct. 17, 2019, which claims priority to U.S. Provisional application Ser. No. 62/746,755, filed Oct. 17, 2018, both of which are herein incorporated by reference in their entireties.

STATEMENT REGARDING FEDERAL FUNDING

This invention was made with government support under AI154072 awarded by the National Institutes of Health. The government has certain rights in the invention.

SEQUENCE LISTING

The text of the computer readable sequence listing filed herewith, titled "37046-502_SEQUENCE_LISTING_ST25", created Apr. 16, 2021, having a file size of 27,618 bytes, is hereby incorporated by reference in its entirety.

FIELD OF THE INVENTION

The present invention provides, in some embodiments, methods, compositions, systems, and kits comprising nano-satellite complexes comprising: a core nanoparticle complex comprising a biocompatible coating surrounding a nanoparticle core; 3-25 satellite particles attached to, or absorbed to, said biocompatible coating; a plurality of antigenic peptides conjugated to, or absorbed to, said satellite particles; and at least one additional property. In other embodiments, provided herein are nano-satellite complexes comprising: a core nanoparticle complex comprising a biocompatible coating surrounding a nanoparticle core; a plurality of satellite particles attached to, or absorbed to, said biocompatible coating; a plurality of antigenic peptides conjugated to, or absorbed to, said satellite particles; and a plurality of LIGHT (TNFSF14) peptides conjugated to, or absorbed to, said satellite particles.

BACKGROUND

Viruses are known to be tremendously efficient delivery vehicles, mediators of cellular uptake and efficacious immunological agents. As such, it has become desirable to utilize viruses and viral properties in wide variety of biotechnology and medicinal applications. However, traditional live attenuated or inactivated viruses remain too dangerous to be employed in this way. To address this concern, virus-like particles have emerged.

Virus-like particles are protein-based nanoparticles that are composed of viral capsid proteins that self-assemble into geometrically rigid nanostructures that directly resemble viral structure and confirmation without the viral genome. Thus, viral-like particles are considered a viable and safe alternative to traditional viruses. Despite this advantage however, numerous obvious disadvantages of virus-like particle technology remain including reliance on protein self-assembly, difficult manufacturing, limited application versatility and significant anti-carrier responses that limits re-dosing potential in-vivo. As a result of these challenges, there has been increasing interest in the development of alternative nanoparticle systems that are viral inspired.

These so-called, viral mimicking nanoparticles are rationally designed and engineered based on an understanding of viral physical and chemical material properties. The viral material properties most commonly utilized to inform the design of viral mimicking nanoparticles include: particle size, particle shape, charge, hydrophobicity, antigen display, antigen organization, antigen density and surface topography. While many advances have been made in the design, engineering and application of viral-mimicking nanoparticles, no one generally applicable nanoparticle system has emerged.

SUMMARY OF THE INVENTION

The present invention provides methods, compositions, systems, and kits comprising nano-satellite complexes comprising: a core nanoparticle complex comprising a biocompatible coating surrounding a nanoparticle core; 3-25 satellite particles attached to, or absorbed to, said biocompatible coating; a plurality of antigenic peptides conjugated to, or absorbed to, said satellite particles; and at least one additional property: i) a weight-to-weight ratio of all of the satellite particles to the nanoparticle core of 10-40%; a diameter of each of the satellite particles is 2-20 nm; iii) the satellite particles are present at density of 500-20,000 or 15,00-30,000 per square micron; iv) the plurality of antigenic peptides is 100-4000 antigenic peptides; v) 10-300 of the plurality of the antigenic peptides are present on each of the satellite particles; and/or vi) the average distance between each of the satellite particles is 5-20 nm. In certain embodiments, the diameter of the nano-satellite complex is about 20-70 nm (e.g., about 25 nm, about 40-50 nm, or about 60 nm). In other embodiments, provided herein are nano-satellite complexes comprising: a core nanoparticle complex comprising a biocompatible coating surrounding a nanoparticle core; a plurality of satellite particles attached to, or absorbed to, said biocompatible coating; a plurality of antigenic peptides conjugated to, or absorbed to, said satellite particles; and a plurality of LIGHT (TNFSF14) peptides conjugated to, or absorbed to, said satellite particles (e.g., a LIGHT protein is at least 190, 200, or 210 consecutive amino acids from a human light protein). In some embodiments, the nanosatellite complexes are efficient for LN homing, unique B cell zone localization, and B cell receptor crosslinking; promote T follicular helper cell (Tfh)-dependent B cell activation in the lymph nodes (LNs) and tertiary lymphoid structures (TLS) neogenesis in tumor and achieve long-term cancer remission (e.g., when combined with an immune checkpoint inhibitor, such as αPD1).

In certain embodiments, provided herein are compositions comprising: a nano-satellite complex, wherein the nano-satellite complex comprises: a) a core nanoparticle complex comprising a biocompatible coating surrounding a nanoparticle core; b) 3-25 satellite particles (e.g., 3 . . . 7 . . . 13 . . . 17 . . . 21 . . . or 25) attached to, or absorbed to, the biocompatible coating; c) a plurality of antigenic peptides (e.g., from Table 4 or Table 1, Table 2, or Table 3), or a plurality of haptens, conjugated to, or absorbed to, the satellite particles; and d) wherein the nano-satellite complex comprises at least one (e.g., 1, 2, 3, 4, 5, or 6) of the following properties: i) wherein the weight-to-weight ratio of all of the satellite particles to the nanoparticle core is 10-40% (e.g., 10% . . . 20% . . . 30% . . . or 40%); ii) wherein the diameter of each of the satellite particles is 2-20 nm (e.g., 2 . . . 5 . . . 8 . . . 13 . . . 17 . . . 20 nm); iii) wherein the satellite particles are present at density of 500-20,000 per square micron (e.g., 500 . . . 1000 . . . 4000 . . . 8000 . . . 13,000 . . . 17,000 . . . or 20,000 per square micron); iv) wherein the plurality of antigenic peptides, or plurality of haptens, is 100-4000 antigenic peptides (e.g., 100 . . . 500 . . . 1000 . . . 2000 . . . 3000 . . . or 4000); v) wherein 10-300 (e.g., 10 . . . 40 . . . 100 . . . 175 . . . 225 . . . or 300) of the plurality of the antigenic peptides, or of the plurality of haptens, are present on each of the satellite particles; and vi) wherein the average distance between each of the satellite particles is 5-20 nm (e.g., 5.0 . . . 6.5 . . . 7.5 . . . 10 . . . 13 . . . 17 . . . or 20 nm).

In certain embodiments, provided herein are compositions, kits, and systems comprising: a nano-satellite complex, wherein said nano-satellite complex comprises: a) a core nanoparticle complex comprising a biocompatible coating surrounding a nanoparticle core (e.g., wherein the nanoparticle core is about 12-18 nm in diameter); b) 10-20 satellite particles attached to, or absorbed to, said biocompatible coating; c) a plurality of antigenic peptides (e.g., from Table 4 or Table 1, Table 2, or Table 3) conjugated to, or absorbed to, said satellite particles; and d) wherein said nano-satellite complex comprises at least one of the following properties: i) wherein the weight-to-weight ratio of all of said satellite particles to said nanoparticle core is 10-40% (e.g., 10% . . . 20% . . . 30% . . . 40%): ii) wherein the diameter of each of said satellite particles is 1-5 nm (e.g., about 1, 2, 3, 4, or 5 nm); iii) wherein said satellite particles are present at density of 15,00-30,000 per square micron (e.g., 15,000 . . . 18,000 . . . 21,000 . . . 25,000 . . . 28,000 . . . or 30,000); iv) wherein said plurality of antigenic peptides is 1500-3000 antigenic peptides (e.g., about 1500 . . . 1900 . . . 2200 . . . 2300 . . . 2600 . . . 3000); v) wherein 100-400 (e.g., 100 . . . 200 . . . 250 . . . 300 . . . 400) of said plurality of said antigenic peptides are present on each of said satellite particles; and vi) wherein the average distance between each of said satellite particles is 4-7 nm (e.g., 4.0 . . . 5.0 . . . 5.2 . . . 5.9 . . . 6.1 . . . or 7.0 nm).

In some embodiments, provided herein are kits and systems comprising: a) a core nanoparticle complex comprising a biocompatible coating surrounding a nanoparticle core; b) 3-25 satellite particles configured to be attached to, or absorbed to, the biocompatible coating; c) a plurality of antigenic peptides, or a plurality of haptens, configured to be conjugated to, or absorbed to, the satellite particles; and d) at least one of the following: i) wherein the weight-to-weight ratio of all of the satellite particles to the nanoparticle core is 10-40%; ii) wherein the diameter of each of the satellite particles is 2-20 nm; and iii) wherein the plurality of antigenic peptides, or plurality of haptens, is 100-4000 antigenic peptides.

In certain embodiments, provided herein are compositions comprising: a nano-satellite complex, wherein the nano-satellite complex comprises: a core nanoparticle complex comprising a biocompatible coating surrounding a nanoparticle core; b) a plurality of satellite particles attached to, or absorbed to, the biocompatible coating; c) a plurality of antigenic peptides conjugated to, or absorbed to, the satellite particles; and d) a plurality of LIGHT (TNFSF14) peptides conjugated to, or absorbed to, the satellite particles (e.g., wherein the LIGHT peptides binds to lymphotoxin-β-receptor (LTβR)).

In certain embodiments, the LIGHT peptide is a full-length human LIGHT peptide or a N-terminal truncated, C-terminal truncated, or mutated version of full-length LIGHT peptide. In other embodiments, the nano-satellite complex comprises at least one of the following properties: i) wherein the weight-to-weight ratio of all of the satellite particles to the nanoparticle core is 10-40%; ii) wherein the diameter of each of the satellite particles is 2-20 nm; iii) wherein the plurality of antigenic peptides is 100-4000 antigenic peptides; iv) wherein 10-300 of the plurality of the antigenic peptides are present on each of the satellite particles; and v) wherein the average distance between each of the satellite particles is 5-20 nm. In further embodiments, the compositions further comprise an immune checkpoint inhibitor. In certain embodiments, provided herein are methods of eliciting an immune response in a subject comprising: administering to a subject a composition herein such that antibodies to the antigenic peptides are generated. In further embodiments, the subject is further administered an immune-checkpoint inhibitor.

In particular embodiments, provided herein are methods of eliciting an immune response in a subject comprising: administering to a subject the composition as described herein such that antibodies to the antigenic peptides, or haptens, are generated. In certain embodiments, the subject is a human. In other embodiments, the subject is an animal (e.g., dog, cat, pig, horse, etc.). In additional embodiments, the methods further comprise taking a sample from the subject, and purifying at some of the antibodies from the sample. In additional embodiments, no adjuvant is administered as part of the composition or otherwise. In some embodiments, the subject is administering a type I interferon agonist agent, either in the composition or separately. In further embodiments, the subject is administering an immune checkpoint inhibitor, either in the composition or separately. In certain embodiments, the antigenic peptides comprise B-Cell epitopes, or T-cell epitopes, or both (see, e.g., Table 4 or Table 1, Table 2, or Table 3). In other embodiments, the nanosatellite complex does not generate detectable non-specific antibody against said nano-satellite complex in the subject. In further embodiments, the nanosatellite complex homes to a lymph node of said subject (e.g., at a level equal to a virus). In further embodiments, the nanosatellite complex homes to a B-cell zone or T-cell zone of a lymph node of said subject. In further embodiments, the nanosatellite complex is taken up by subcapsular sinus macrophages in said subject at a rate equal to a virus.

In certain embodiments, the satellite particles comprise gold. In other embodiments, the core nanoparticle comprises $Fe_3O_4$. In some embodiments, the biocompatible coating comprises polysiloxane. In other embodiments, the nanoparticle core comprises $Fe_3O_4$, the biocompatible coating comprises polysiloxane, and the at least one satellite particle comprises a plurality of satellite particles composed of gold.

In some embodiments, the 3-25 satellite particles is 10-15 satellite particles. In other embodiments, the at least one property is wherein the weight-to-weight ratio of all of the satellite particles to the nanoparticle core is 10-40% (e.g., about 30%). In additional embodiments, the weight-to-weight ratio of all of the satellite particles to the nanoparticle core is 25-35%. In certain embodiments, the weight-to-weight ratio of all of the satellite particles to the nanoparticle core is 29-31%.

In some embodiments, the at least one property is wherein the diameter of each of the satellite particles is 2-20 nm. In certain embodiments, the diameter of each of the satellite particles is 5-15 nm. In further embodiments, the diameter of each of the satellite particles is 4-6 nm.

In particular embodiments, the at least one property is wherein the satellite particles are present at density of 500-20,000 per square micron. In other embodiments, the satellite particles are present at a density of 13,000 to 17,000 per square micron.

In some embodiments, the at least one property is wherein the plurality of antigenic peptides is 100-4000 antigenic peptides or 100-4000 haptens. In other embodiments, the plurality of antigenic peptides is 1500-2500 antigenic peptides, or wherein the plurality of haptens is 1500-2500.

In other embodiments, the at least one property is wherein 10-300 of the plurality of the antigenic peptides, or haptens, are present on each of the satellite particles. In further embodiments, 225-275 of the plurality of antigenic peptides, or haptens, are present on each of the satellite particles.

In some embodiments, the at least one property is wherein the average distance between each of the satellite particles is 5-20 nm. In certain embodiments, the average distance between each of the satellite particles is 6-8 nm.

In further embodiments, the at least one property is at least two or three of the properties. In some embodiments, the at least one property is at least four or five of the properties. In additional embodiments, the at least one property is all six of the properties.

In certain embodiments, the antigenic peptide comprises: i) a neoantigenic determinant, ii) at least one epitope from a tumor antigen, iii) at least one epitope from a viral oncoprotein, iv) a least one epitope from an infectious virus, v) at least one epitope from a parasite, or vi) at least one epitope from an infectious bacteria. In further embodiments, the compositions, systems, and kits further comprise a physiologically compatible aqueous solution and/or cancer cells and/or antigen presenting cells.

In some embodiments, the plurality of antigenic peptides are not uniformly distributed on the satellite particles. In other embodiments, the nano-satellite complex is a diameter of 50-100 nm (e.g., 55-65 nm). In further embodiments, the surface of the nano-satellite complex is negatively charged (e.g., −10 to −20 mV). In other embodiments, the core nanoparticle has a diameter of 10-25 nm (e.g., 15-20 nm).

In some embodiments, the composition further comprises a type I interferon agonist agent. In other embodiments, the type I interferon agonist agent is electrostatically attracted to, or absorbed to, i) the antigenic peptides or haptens, ii) the plurality of satellite particles, and/or iii) the core nanoparticle. In additional embodiments, the compositions are adjuvant-free. In additional embodiments, the compositions further comprise an immune checkpoint inhibitor.

In further embodiments, the antigenic peptide comprises at least one neoantigenic determinant, including, for example, an oncogenic viral antigenic determinant. In some embodiments, the antigenic peptides comprise at least one epitope from a tumor antigen, including a viral oncoprotein. In certain embodiments, the antigenic peptide comprises a least one epitope from an infectious virus, at least one epitope from a parasite, and/or at least one epitope from an infectious bacteria. Suitable antigens from viruses, parasites, and bacteria for immunizing subject (e.g., human subjects) are well known in the art (see, e.g., Tables 2 and 3). Additional antigens are in development for vaccines including, for example: Adenovirus vaccine, Coxsackie B virus vaccine, Cytomegalovirus vaccine, Dengue vaccine, Eastern Equine encephalitis virus vaccine, Ebola vaccine, Enterovirus 71 vaccine, Epstein-Barr vaccine, Hepatitis C vaccine, HIV vaccine, HTLV-1 T-lymphotropic leukemia vaccine, Marburg virus disease vaccine; Norovirus vaccine; Respiratory syncytial virus vaccine; Severe acute respiratory syndrome (SARS) vaccine; West Nile virus vaccine; Zika fever; Caries vaccine; Ehrlichiosis vaccine; Leprosy vaccine; Lyme disease vaccine; *Staphylococcus aureus* vaccine; *Streptococcus pyogenes* vaccine; Syphilis vaccine; Tularemia vaccine; *Yersinia pestis* vaccine; Malaria vaccine; Schistosomiasis vaccine; Chagas disease vaccine; Hookworm vaccine; Onchocerciasis river blindness vaccine for humans; Trypanosomiasis vaccine; and Visceral leishmaniasis vaccine.

In certain embodiments, the methods of administering the nano-satellite complexes herein to a subject kills at least some cancer cells and/or modulates antigen-specific immune response in the subject. In further embodiments, the cancer cells are from a type of cancer selected from the group consisting of: head and neck squamous-cell carcinoma (HNSCC), HPV-positive cancer, odontogenic tumors, bladder cancer, breast cancer, cervical cancer, colorectal cancer, leukemia, melanoma, non-small lung cell cancer (NSCLC), ovarian cancer, pancreatic cancer, and prostate cancer. In additional embodiments, the cancer cells are part of a tumor in the subject. In further embodiments, the tumor is a hypo-immunogenic "cold" tumor, which is characterized by insufficient elicitation of tumor-specific immunity and resistance to immunogenic cytotoxicity.

In certain embodiments, the nano-satellite complexes can be also used as a photothermal agent and/or an MRI contrast agent. In certain embodiments, the type I interferon agonist agent comprises activators of a type I interferon signaling adaptor protein, stimulator of interferon genes (STING), which include cyclic dinucleotides selected from c-di-GMP, c-di-AMP, and cGAMP, or its analogs. In other embodiments, the STING agonist agent is selected from the group consisting of: c-di-IMP, c-di-UMP, and 5,6-dimethylxanthenone-4-acetic acid (DMXAA), 2'3'-cGAM(PS)$_2$ (Rp/Sp), and 2'3'-c-di-AM(PS)$_2$(Rp,Rp). In other embodiments, the type I interferon agonist agent comprises a Toll-like Receptor (TLR) family protein agonist, such as TLR9 agonist CpG. In particular embodiments, the kits, compositions, and systems further comprise a physiologically compatible aqueous solution and/or cancer cell lysates.

In certain embodiments, the subject is a human or other mammal. In some embodiments, the methods comprise combining the aforementioned nanosatellite complex with the administration of an immune checkpoint inhibitor agent to the subject. These immune checkpoint inhibitors may include monoclonal antibodies, such as anti-PD-L1, anti-CLTA-4, or anti-PD-1. In further embodiments, the immune check-point inhibitor agent is selected from: YERVOY (ipilimumab), KEYTRUDA (pembrolizumab), OPDIVO (nivolumab), and TECENTRIQ (atezolizumab).

In some embodiments, the core comprises a material selected from: near-infrared photothermal agent material and MRI contrast agent material, and the at least one satellite particle comprises near-infrared photothermal agent material, MRI contrast agent material, and near-infrared optical dye material. In additional embodiments, the nanoparticle core comprises a material that is selected from the group consisting of: $Fe_3O_4$, silicon, gold, copper, and carbon. In some embodiments, the at least one satellite particle comprises a material is selected from the group consisting of: gold sulfide ($Au_2S$), copper sulfide ($Cu_2S$), carbon nanotubes, and graphene. In certain embodiments, there is no shell surrounding the core, but instead, there are the one or more satellite particles are clearly visible as discrete particles (e.g., as view by a tunneling electron microscope).

In embodiments, the nanoparticle core comprises $Fe_3O_4$, and/or biocompatible coating comprises polysiloxane, and/or the at least one satellite particle comprises a plurality of satellite particles composed of gold. In certain embodiments, the core particle has a diameter of 15-20 nm. In other embodiments, the satellite particles have an average diameter of 2-6 nm. In particular embodiments, the core particle is spherical or cubical in shape.

In further embodiments, the core nanoparticle comprises a first type of material is selected from the group consisting of: $Fe_3O_4$, silicon, gold, copper, and carbon. In particular embodiments, the first type of material comprises $Fe_3O_4$. In additional embodiments, the $Fe_3O_4$ is highly crystallized and has an X-ray diffraction (XRD) pattern where the brightest diffraction ring is from the 440 plane. In further embodiments, the $Fe_3O_4$ has a preferred lattice orientation along the 400 and 440 XRD diffraction planes. In other embodiments, the satellite particle comprise a second type of material that is selected from the group consisting of: gold, gold sulfide ($Au_2S$), copper, copper sulfide ($Cu_2S$), carbon, carbon nanotubes, and graphene. In certain embodiments, the second type of material comprises gold sulfide ($Au_2S$). In other embodiments, the near-infrared optical dye material is selected from the group consisting of: IR820, ICG, and 5, aminolevulinic acid (5-ALA). The present invention is not limited by the shape of the core or the satellite particle. Examples of shapes include, but are not limited to, spherical, cubic, rod shaped, disc shaped, etc.

In some embodiments, each of the satellite particles has a size between 0.5 nm and 25 nm in diameter (e.g., 0.5 . . . 1.5 . . . 10 . . . 15 . . . 20 . . . 23 . . . and 25 nm). In further embodiments, the satellite particles have a size between 2 nm and 7 nm in diameter (e.g., about 5 nm or about 2-4 nm). In further embodiments, the nanoparticle core has a size between 35 and 100 nm in diameter. In further embodiments, the nano-satellite complex is present in the composition at a concentration of between 1.0 and 5.0 mg/mL (e.g., 1.0 . . . 3.3 . . . and 5.0 mg/ml). In other embodiments, the biocompatible coating comprises a material selected from the group consisting of: human serum albumin (HSA), polyethylene glycol, triblock copolymer, PEO-b-PPO-b-PEO (F121), PEO-b-PVP, glucosylated poly(pentafluorostyrene), chitosan, silica, and gum Arabic, gluconic acid, lactobionic acid, polyacrylic acid, apatite, and Casein. In additional embodiments, the biocompatible coating is functionalized with thiol groups or amine groups. In particular, one can use siloxane molecules like (3-Mercaptopropyl)trimethoxysilane (MPTMS) to produce thiol groups or (3-Aminopropyl)triethoxysilane to produce amine groups on nanoparticle surfaces to functionalize polymer coated nanoparticles.

In some embodiments, the administering the nano-satellite complexes to a subject generates a plurality of core-satellite nanocomposite-impregnated cancer cells in the subject. In further embodiments, the methods comprise: subjecting the subject to photothermal therapy and/or imaging, wherein the photothermal therapy: A) comprises the use of a treatment device that emits electromagnetic radiation, and B) causes at least a portion of the core-satellite nanocomposite-impregnated cancer cells to be damaged or killed; and wherein the imaging: A) comprises the use of an imaging device configured for MRI/NMR detection and/or optical detection, and B) causes at least a portion of the core-satellite nanocomposite-impregnated cancer cells to be visualized ex-vivo.

DESCRIPTION OF THE FIGURES

The patent or application file contains at least one drawing executed in color. Copies of this patent or patent application publication with color drawings will be provided by the Office upon request and payment of the necessary fee.

FIG. 1, bottom, shows a simplified schematic for generating lipid-coated iron-oxide nanoparticle (Lipid-IONP), which are used as controls in Example 1.

FIG. 3A shows the experimental timeline and immunization schedule. FIG. 3B shows the antigen-specific IgG titers at different IVLN formulation conditions and peptide densities 10 days after boost 1. FIG. 3C shows the antibody quantification and antigen-specific IgG titers for IVLN versus soluble and nanoparticle-type controls.

FIG. 4 shows the amino acid sequence of ERBB2/HER2 protein (SEQ ID NO:4), with identified T cell epitopes or HLA ligands are highlighted in gray shading, as provided by TANTIGEN, the Tumor T-cell Antigen Database.

FIG., panels A-C, 7 shows data from Example 2 which showed that the tested IVLN-HER2 Enhanced antigen-specific antibody production. (A) Animal study immunization and analytical sampling timeline. (B) Quantification of non-specific total IgG and antigen-specific antibody titers (IgG, IgG1 and IgG2a) from the serum of BALB/c mice at day 38 and at 5 μg HER2 peptide+10 μg cGAMP as adjuvant. (C) Quantification of non-specific total IgG and antigen-specific antibody titers (IgG, IgG1 and IgG2a) from the serum of BALB/c mice at day 38 and at 50 μg HER2 peptide+10 μg cGAMP as adjuvant; data represent mean±SE, n=5. Data represent mean±SE, n=5. Statistical comparisons are based on one-way ANOVA, followed by post hoc Tukey's pairwise comparisons. The asterisks denote statistical significance at the level of *$p<0.05$, $p<0.01$, *$p<0.001$. ANOVA, analysis of variance; SE, standard error; n.s., no statistical significance.

Figure 8:
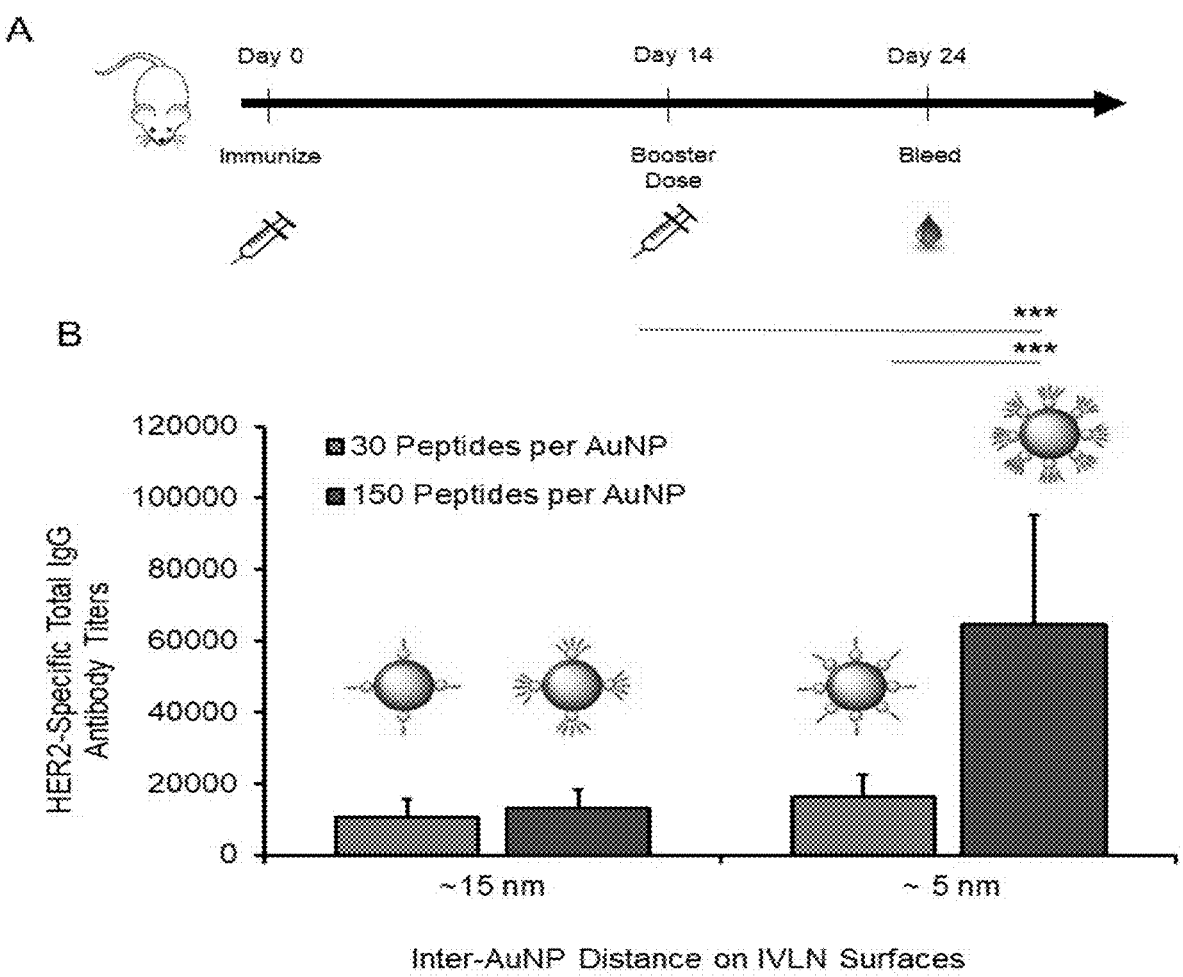

FIG. 8, panels A-B, shows results from Example 2, including results with an IVLN with the following properties: antigen clusters (14 clusters), distance between antigen clusters (5-6 nm), and localized antigen density (2000 peptides/IVLN, ~150 peptides/AuNP) for generation of HER2-specific IgG. (A) Immunization scheme in mice. (B) Quantification of antigen-specific IgG antibodies by ELISA represented as antibody titer; data represent mean±SE, n=5. Statistical comparisons are based on one-way ANOVA, followed by post hoc Tukey's pairwise comparisons. The asterisks denote statistical significance at the level of *$p<0.05$, $p<0.01$, *$p<0.001$. ANOVA, analysis of variance; SE, standard error.

Figure 9:
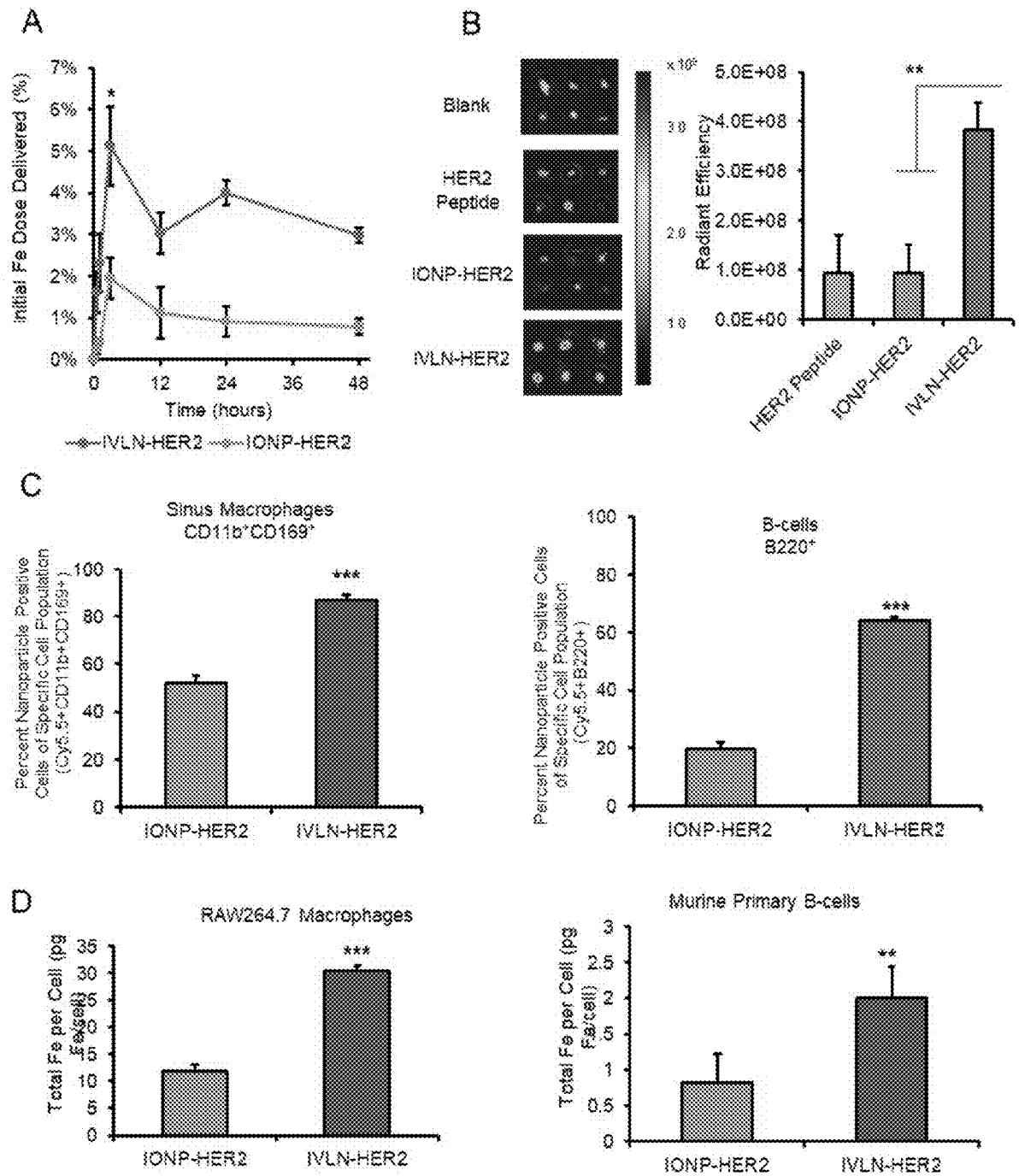

FIG. 9, panels A-D, shows results from Example 2 that shows IVLN-HER2 improved lymph node delivery and B cell zone distribution in comparison with IONP-HER2.

FIG. 9 A Quantification of nanoparticle delivery to lymph nodes (popliteal+inguinal) ipsilateral to the administration site at designated time intervals represented as the percentage of initial iron-oxide delivered using ICP-MS; data represent mean±SE, n=3. FIG. 9 B Representative ex-vivo IVIS fluorescence images and semi-quantitative analysis (popliteal (top)+inguinal (bottom)) of peptide delivery to lymph nodes acquired 3 hours after administration of Cy5.5-labeled soluble HER2 peptide, IONP-HER2-Cy5.5 and IVLN-HER2-Cy5.5 (Ex/Em=675/720 nm, exposure=0.5 s). The color bar represents mean radiant efficiency (p/s/cm$^2$/sr)/(μW/cm$^2$); data represent mean±SD, n=3. FIG. 9 C Quantification of in-vivo nanoparticle distribution to specific immune cell populations in the lymph nodes as identified by flow cytometry (Cy5.5-labeled nanoparticles); Subcapsular sinus macrophages are identified as CD11b$^+$ CD169$^{high}$; B-cells are identified as B220$^+$; data represent mean±SD, n=3. FIG. 9 D Quantification of in-vitro cell uptake of nanoparticles in RAW264.7 macrophages and murine primary B-cells by ICP-MS quantification of total Fe standardized by cell count (pg Fe per cell). Data represent mean±SD, n=3. Statistical comparisons are based on one-way ANOVA, followed by post hoc Tukey's pairwise comparisons or by Student's unpaired T-test. The asterisks denote statistical significance at the level of $p<0.01$, *$p<0.001$. ANOVA, analysis of variance; SD, standard deviation; SE, standard error.

FIG. 10, panels A-C, shows results from Example 2 that show IVLN-HER2 induced HER2-specific antibody has function to inhibit HER2+ cancer. (A) Animal study immunization and HER2$^+$ breast cancer (D2F2/E2) tumor inoculation timeline. (B) Tumor volume growth curves for D2F2/E2 tumors subcutaneously implanted into the flank of BALB/c mice at 250,000 cells per mouse treated with 50 μg HER2 peptide dose+10 μg cGAMP. (C) Tumor volume growth curves for D2F2/E2 tumors subcutaneously implanted into the flank of BALB/c mice at 250,000 cells per mouse treated with 5 μg HER2 peptide dose+10 μg cGAMP. Data represent mean±SE, n=5. Statistical comparisons are based on one-way ANOVA, followed by post hoc Tukey's pairwise comparisons. The asterisks denote statistical significance at the level of *$p<0.05$, $p<0.01$, *$p<0.001$. ANOVA, analysis of variance; SE, standard error.

Figure 11:
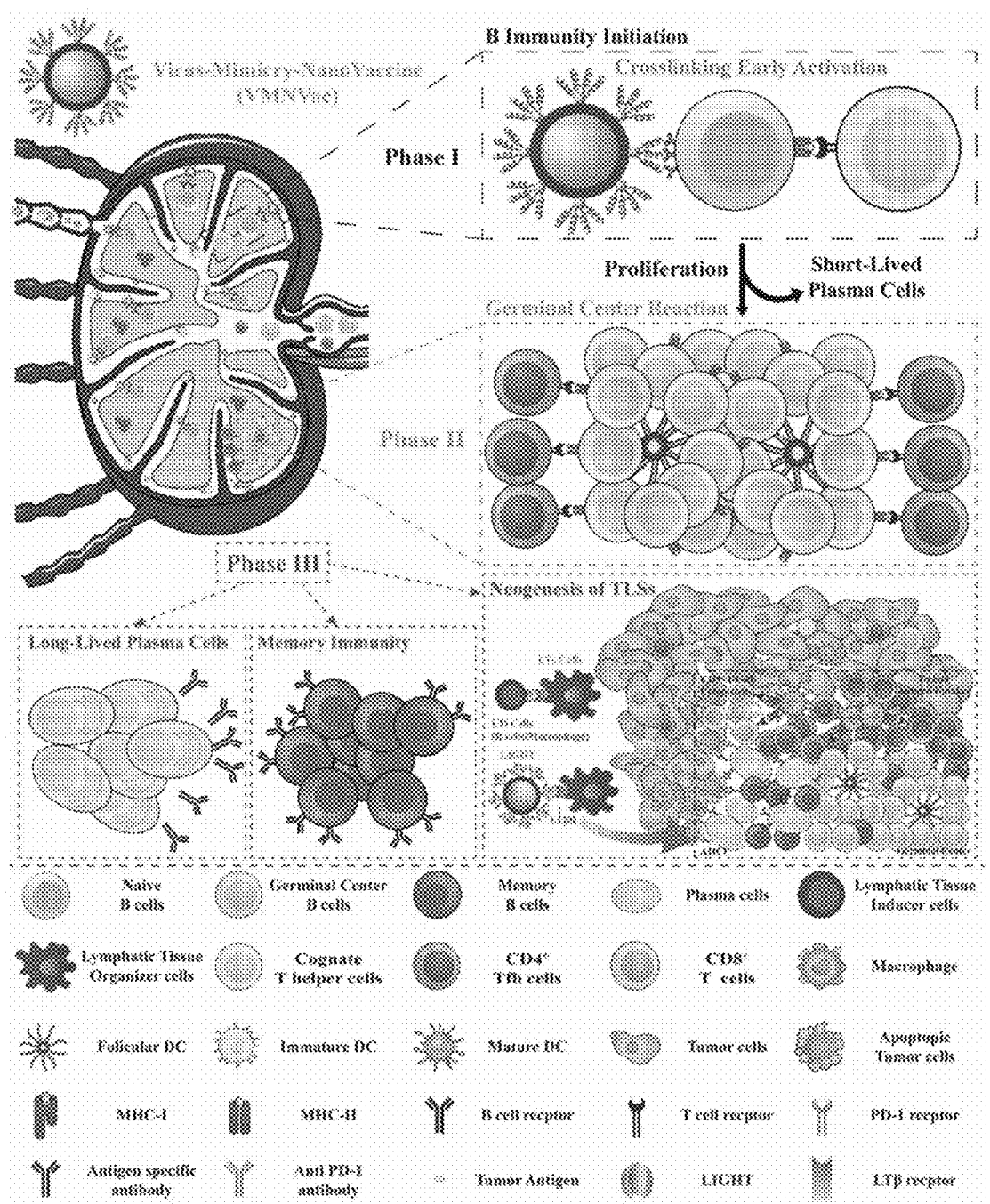

FIG. 11 shows an exemplary scheme (Scheme 1), where an exemplary virus-spike-mimicry B cell nanovaccine is combined with a checkpoint inhibitor (e.g., αPD1) to achieve remission in HER2+ breast cancer by promoting Tfh-dependent B cell activation in lymph node and tertiary lymphoid structure in tumors.

Figure 12A:
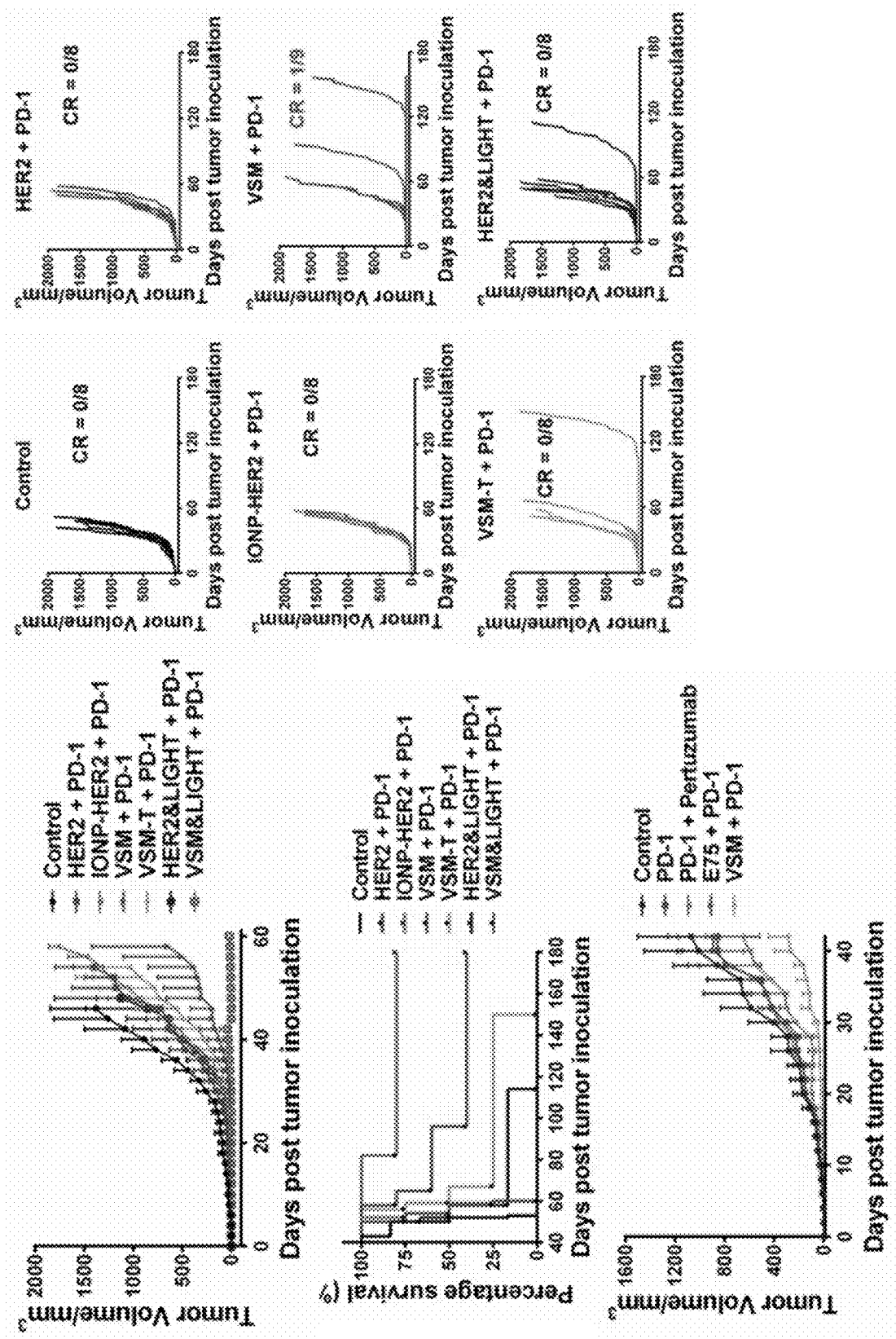

FIG. 12A shows the anti-tumor effects of nanovaccines herein based on different regimens which achieve remission in HER2+ breast cancer by virus spike mimicry nanovaccine (VSMVax) and LIGHT.

Figure 12B:
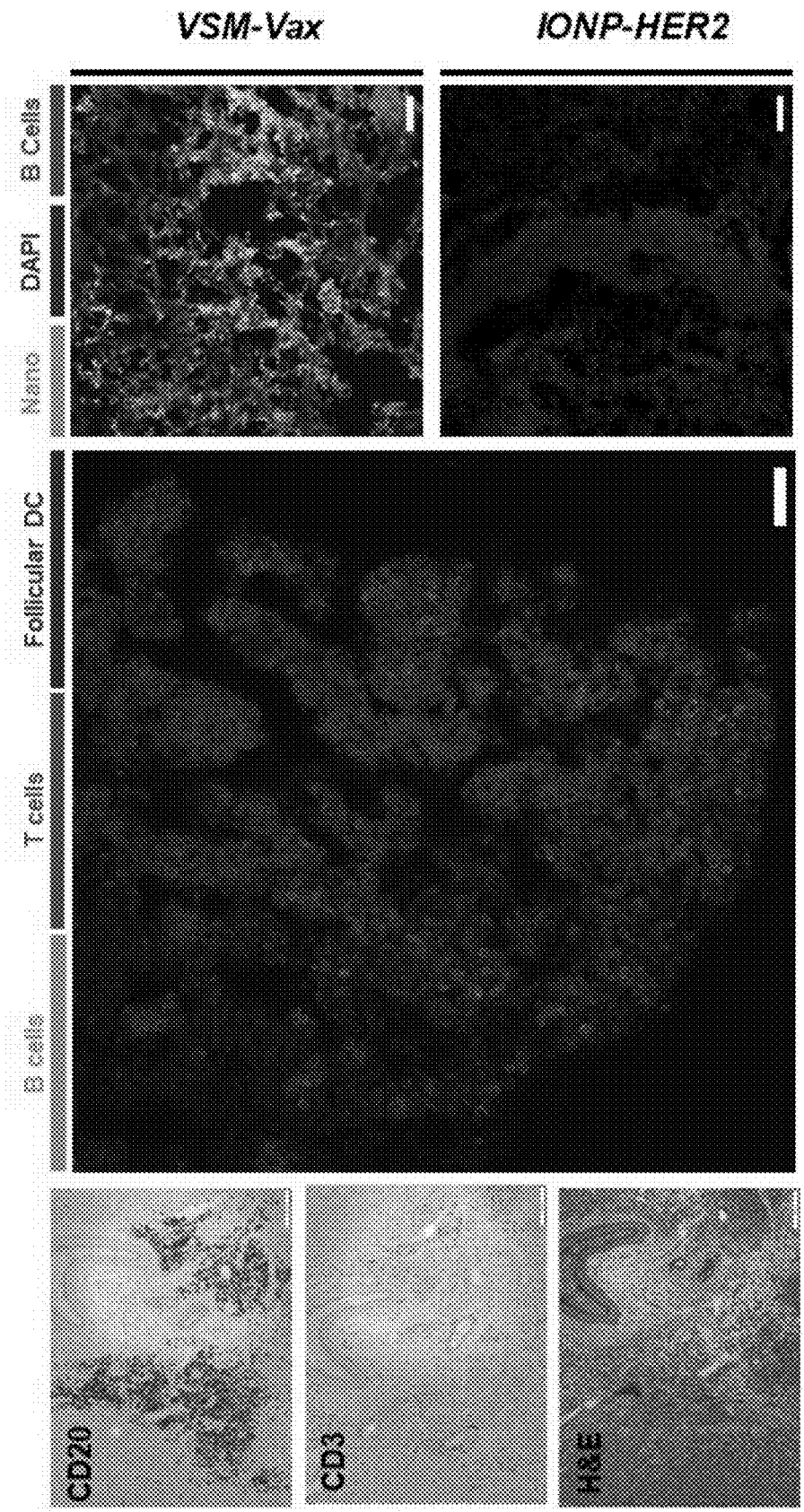

FIG. 12B shows tertiary lymphoid structures in tumor by VSMVax

Figure 13:
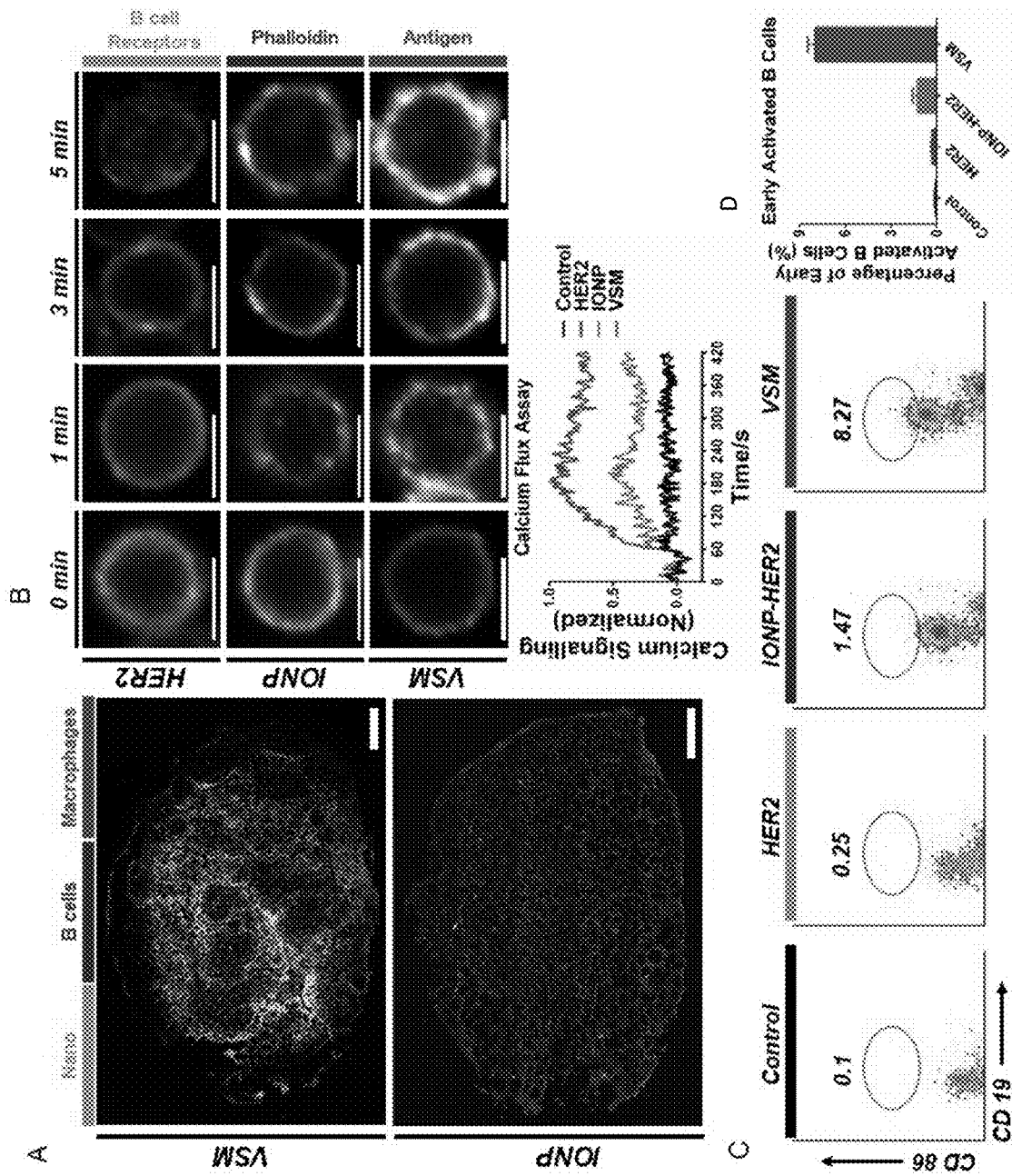

FIG. 13, panels A-C, shows results of Example 3, that show efficient lymph node draining and efficient Macrophage/B cell uptake. (A) shows results of lymph node draining of VSM nanovax. (B) shows B cell zone localization. (C) shows B cell receptor (BCR) crosslink activation. (D) shows B cell early activation.

Figure 14:
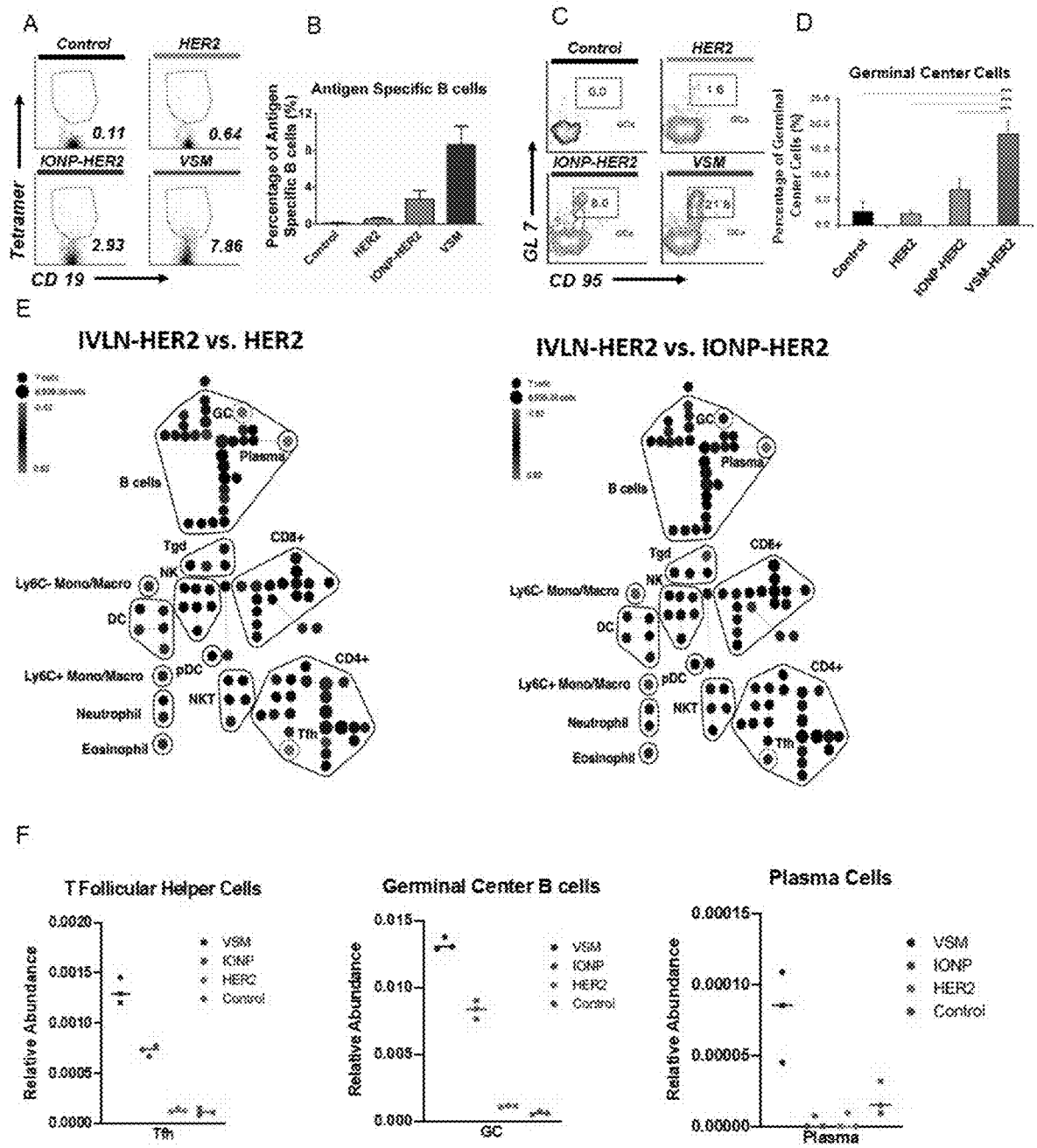

FIG. 14, panels A-F, shows the VSMVax in Example 3 increased 6-fold higher Ag-specific B cell activation and GC formation vs. IONP-HER2. (A) Representative FACS plots for the gating strategy of HER2-specific B-cells using B-cell receptor tetramer staining, identified as the CD19$^+$ Tetramer+ population. (B) Quantification of the percentage of HER2-specific B-cells of total viable cells induced 10 days after the primary immunization at 50 μg HER2 peptide dose+10 μg cGAMP as adjuvant; data represent mean±SE, n≥3. (C) Representative FACS plots for the gating strategy of GC cells. GC cells were identified as the B220$^+$IgD$_{low}$ population that was double-positive for mature GC cell marker CD95 and GL-7. (D) Quantification of percentage of GC type cells of the total B220$^+$ B-cell population induced 10 days after the primary immunization at 50 μg HER2 peptide dose+10 μg cGAMP as adjuvant; data represent mean±SE, n≥3. Statistical comparisons are based on one-way ANOVA, followed by post hoc Tukey's pairwise comparisons. The asterisks denote statistical significance at the level of *$p<0.05$, ***$p<0.001$. ANOVA, analysis of variance; SE, standard error. (E) shows a CyTOF analysis of immune cells reveals that IVLN-HER2 promoted Tfh-dependent B cell activation in the lymph node. CyTOF analysis of immune cells in the lymph node 38 days after first immunization (10 days after second boost). Global analysis using SPADE unsupervised clustering analysis. Nodes contain cells with similar marker expression. Nodes are colored based on whether the relative number of cells within that node is higher (blue) or lower (red) in IVLN-HER2 samples in comparison with IONP-HER2 or HER2. (F) The frequencies of germinal center B cells (CD19+/GL7+ or B220+/GL7+) in the lymph node in mice immunized with INLN-HER2, INOP-HER2, and HER2 peptide alone. The frequencies of CD4+T follicular helper T cells (CD4+/CXCR5+/PD-1+) in the lymph nodes of the mice immunized with INLN-HER2, INOP-HER2, and HER2 peptide. The frequencies of plasma cells in the lymph nodes of the mice immunized with INLN-HER2, INOP-HER2, and HER2 peptide. (50 ug HER2 Peptide, 10 ug cGAMP). FIG. 14F antibody production by VSMvax in example 3.

Figure 15A:
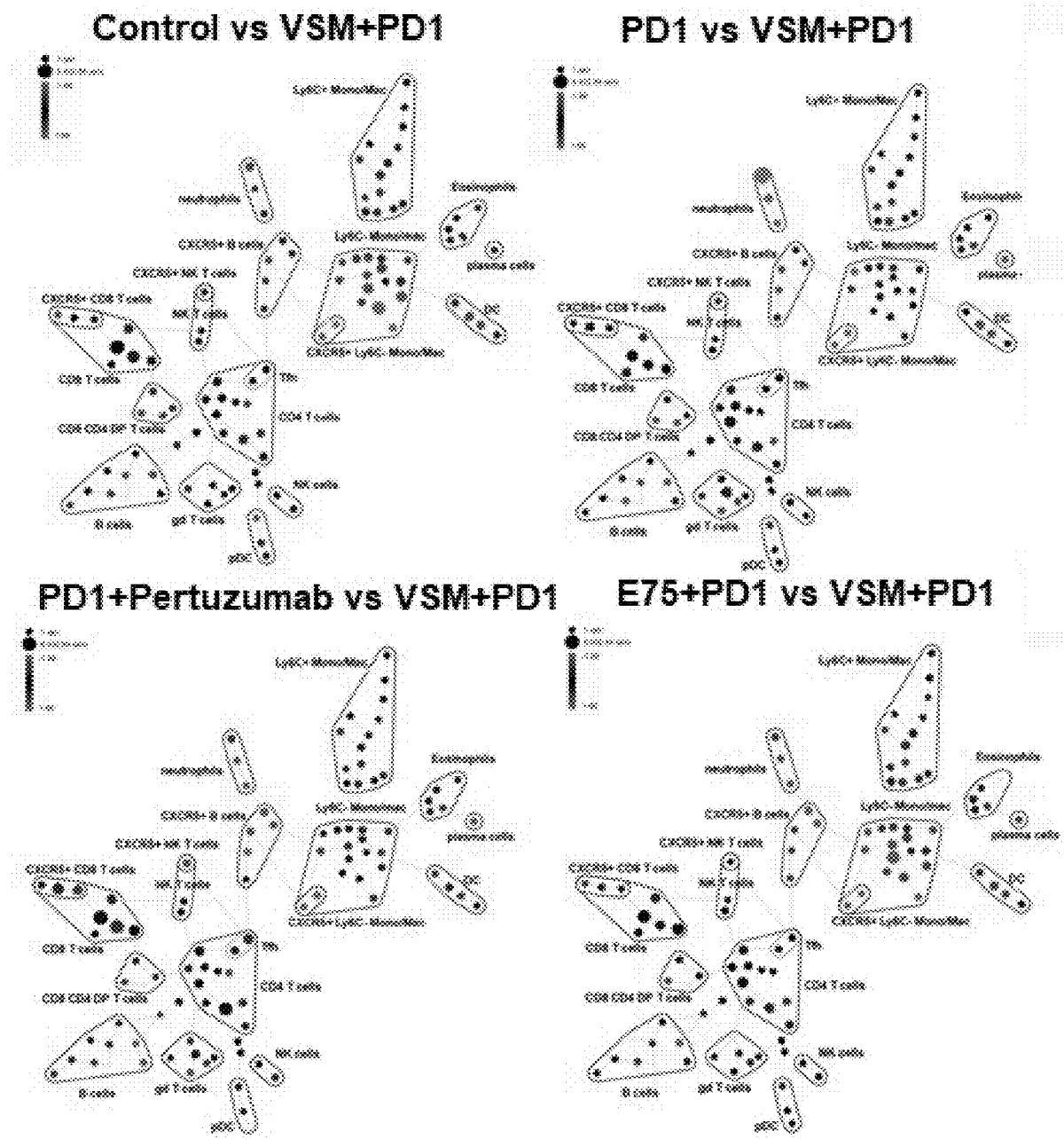

FIGS. 15A-B show VSMVax increase 4d B cells, Tfh-cells in tumors as analyzed by CyTOF analysis. FIG. 15A, Spade analysis of all immune cells in tumors in different treatment groups. FIG. 15 B describes the percentage changes of immune cells in tumors after VSMvax treatment as shown in example 3.

FIG. 16 shows the amino acid sequence of an exemplary human LIGHT peptide. In some embodiments, the nano-satellite complexes employ a peptide with this sequence, or at least part of one at accession number NP_742011 or NP_001363816. In particular embodiments, the nano-satellite complexes employ a portion or fragment of a human LIGHT peptide that still binds to lymphotoxin-β-receptor (LTβR) (e.g., where 5-15 amino acids are removed from either end, or both ends, of the full-length peptide; or a LIGHT peptide that is at least 190, 200, or 210 consecutive amino acids from a human light protein). Portions that bind this receptor can be determined in an in vitro screening assay by, for example, using N-terminal, or C-terminal deletions or mutants of human LIGHT peptide. The fragments of different lengths of LIGHT also have similar effect to stimulate TLS formation and enhance anticancer efficacy.

DETAILED DESCRIPTION

The present invention, in some embodiments, provides methods, compositions, systems, and kits comprising nano-satellite complexes comprising: a core nanoparticle complex comprising a biocompatible coating surrounding a nanoparticle core; 3-25 (or 2-35) satellite particles attached to, or absorbed to, said biocompatible coating; a plurality of antigenic peptides (or haptens with carrier) conjugated to, or absorbed to, said satellite particles; and at least one additional property: i) a weight-to-weight ratio of all of the satellite particles to the nanoparticle core of 10-40%; a diameter of each of the satellite particles is 2-20 nm; iii) the satellite particles are present at density of 500-20,000 or 15,00-30,000 per square micron; iv) the plurality of antigenic peptides is 100-4000 antigenic peptides; v) 10-300 of the plurality of the antigenic peptides are present on each of the satellite particles; and/or vi) the average distance between each of the satellite particles is 5-20 nm. In certain embodiments, the nanosatellite complexes have a viral-like topology with virus-like antigen patch distances and a 3D patch topology. In other embodiments, provided herein are nano-satellite complexes comprising: a core nanoparticle complex comprising a biocompatible coating surrounding a nanoparticle core; a plurality of satellite particles attached to, or absorbed to, said biocompatible coating; a plurality of antigenic peptides conjugated to, or absorbed to, said satellite particles; and a plurality of LIGHT (TNFSF14) peptides conjugated to, or absorbed to, said satellite particles.

Viruses are nature's most efficient delivery vehicles and efficacious immunological agents. As such, for decades now, viral material properties have been inspirational to nanoparticle design and engineering. These so-called viral mimicking nanoparticles have the potential to be widely exploited for applications including drug delivery, molecular imaging, cancer immunotherapy and genetic transfections. However, to date, this potential has been limited by a selective material property approach to viral mimicry. Here, we demonstrate that a holistic approach to viral mimicking nanoparticle design is vital for functional efficacy. Specifically, in some embodiments, described herein are nano-satellite complexes that, in comparison to traditional nanoparticle systems, has unique surface roughness, epitope organization and epitope density. Work conducted during developments of embodiments, herein, it was found that, in the context of B-cell immunity and lymph node delivery, these nanoparticles features resulted in 18.5-fold improvement in antigen-specific IgG antibody production in a mouse model (see Example 1). Mechanistically, it was shown that this significant improvement in antibody production is the result of a 3-fold improvement in lymph node delivery and 2 to 3-fold higher retention with relevant immune cell populations, which facilitates an increase in B-cell activation and germinal center formation, respectively.

In certain embodiments, the nano-satellite complexes herein employ a hybrid Fe@Au core/satellite nanoparticle with a poly(siloxane) containing diblock copolymer coated iron-oxide nanoparticle core (e.g., IONP, 15-20 nm) that anchors a controlled quantity of gold nanoparticles (e.g., AuNP, 2-3 nm) to the surface. Through these gold nanoparticles, terminally cysteine modified peptides are conjugated at defined quantities and densities utilizing the Au—S bond.

While the present disclosure is not limited to any particular mechanism, it is believed that, compared to traditional viral mimicking nanoparticle systems, the nano-satellite nanoparticle complexes herein incorporates more biologically relevant surface topography, as well as antigen display at spatially defined and locally high density that is akin to the geometric rigidity of viruses. The nano-satellite nanoparticles herein can be harnessed for a myriad of biological applications, including use in the context of B-cell immunity. In this context, these unique material properties would manifest as enhanced antigen-presenting cell uptake and B-cell immunity due to improved B-cell receptor crosslinking.

In work conducted during development of embodiments, herein, the results generated (in Example 1) indicate that nano-satellite complexes can be successfully prepared as approximately 60 nm particles hydrodynamically with 10-15 AuNPs per IONP core, which correlates to a less than 7.5 nm distance between AuNPs that is ideal for B-cell receptor crosslinking. Additionally, the nano-satellite complexes herein can be prepared with about 2,000 peptides per particle with specific localization to AuNPs.

In certain embodiments, the nano-satellite complexes herein employ the combination of B cell epitopes, CD4 T cell epitopes or CD8 T cell epitopes (to induce both B cell immunity and T cell immunity), and LIGHT peptides to induce tertiary lymphoid structures (TIS). Such nano-satellite complexes allow, in certain embodiments: i) for efficient lymph node homing and B cell zone localization, ii) induction of both B cell immunity and T cell immunity; iii) induction of Tfh cells; iv) induction of GC B cells, long term memory B cells; v) induction of long term antibody production with high specificity and affinity; and/or vi) induction of TLS in tumors. In some embodiments, such nano-satellite complexes achieve long term tumor remission (alone or in combination with anti-PD1/PD-L1 therapy) to treat or prevent various cancer types.

The present disclosure is not limited by the type of antigen that is used with in the nano-satellite complexes. In certain embodiments, a B-cell antigen and/or T-cell antigen is employed. In certain embodiments, at least a portion of a human tumor-associated antigen is employed. Examples of human tumor-associated antigens (TAAs) include differentiation antigens (such as melanocyte differentiation antigens), mutational antigens (such as p53), overexpressed cellular antigens (such as HER2), viral antigens (such as human papillomavirus proteins), and cancer/testis (CT) antigens that are expressed in germ cells of the testis and ovary but are silent in normal somatic cells (such as MAGE and NY-ESO-1). In other embodiments, antigens from bacteria or viruses are employed.

Figure 5:
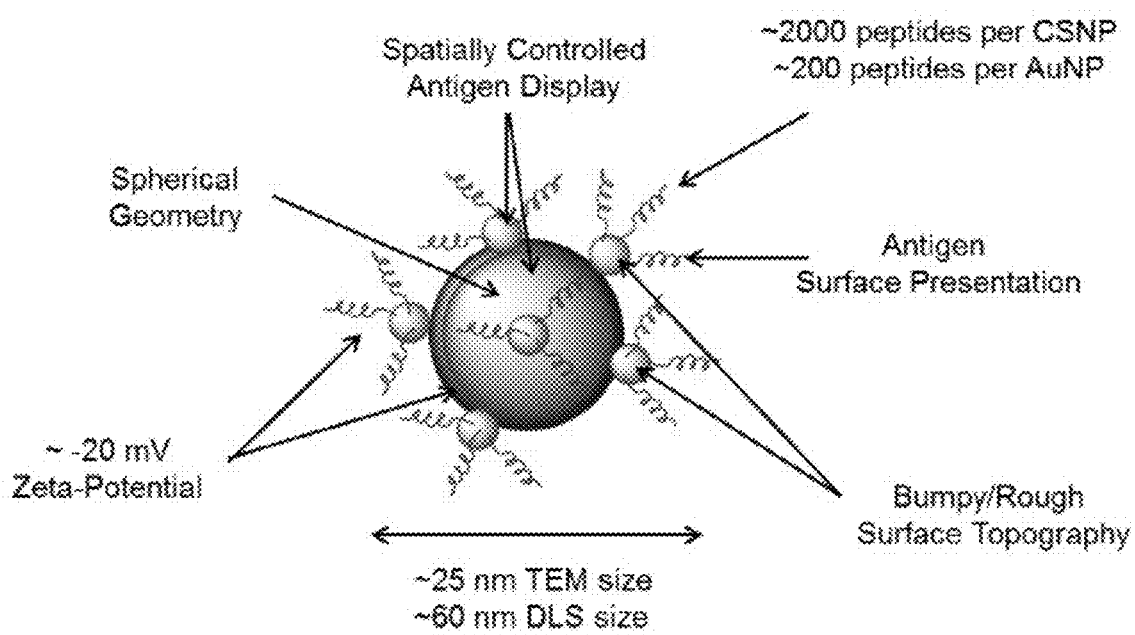
FIG. 5 shows an exemplary nano-satellite complex, with various exemplary parameters labelled.

In certain embodiments, the antigen is provided from the TANTIGEN web site that provide a comprehensive database of tumor T cell antigens (See, Olson et al., Cancer Immunol Immunother. 2017 Mar. 9, which is herein incorporated by reference in its entirety). Table 1 below provides a list of antigens, at least a portion of which may be employed with the nano-satellite complexes provided herein. The TANTIGEN web site may be used to select portions of a particular antigen (see, "http://" followed by "projects.met-hilab.org/tadb/index.php"). For example, with regard to the ERBB2/HER2 antigen, the TANTIGEN web site shows the amino acid sequence for this antigen, providing highlighted short antigenic regions of this antigen that are immunogenic (as shown in FIG. 5, for the TANTIGEN accession number "Ag000001"). One may employ one or more of the highlighted regions of this antigen in the complexes described herein. The same procedure may be employed with any of the antigens listed in Tables 1 and 4 using the TANTIGEN web site or similar resource. In further embodiments, ongoing cancer deep sequencing provides new tools for additional neoantigen discovery which may be employed with the present disclosure. The nano-satellite complex and/or the serum albumin carrier-antigen-adjuvant complex are not limited by the specific sequences of the antigenic peptides. Both systems provide methods, compositions, and kits to specifically modulate the additional neoantigen-targeted immune response.

TABLE 1

| Antigen Name | Common Name |
|---|---|
| ERBB2 | HER2 |
| BIRC5 | Survivin |
| CEACAM5 | CEA |
| WDR46 | BING4 |
| BAGE | BAGE1 |
| CSAG2 | TRAG-3 |
| DCT | TRP-2 |
| MAGED4 | |
| GAGE1 | GAGE-1 |
| GAGE2 | GAGE-2 |
| TGAGE3 | GAGE-3 |
| GAGE4 | GAGE-4 |
| GAGE5 | GAGE-5 |
| GAGE6 | GAGE-6 |
| GAGE7 | GAGE-7 |
| GAGE8 | GAGE-8 |
| IL13RA2 | Interleukin 13 receptor alpha 2 |
| MAGEA1 | MAGE-A1 |
| MAGEA2 | MAGE-A2 |
| MAGEA3 | MAGE-A3 |
| MAGEA4 | MAGE-A4 |
| MAGEA6 | MAGE-A6 |
| MAGEA9 | MAGE-A9 |
| MAGEA10 | MAGE-A10 |
| MAGEA12 | MAGE-A12 |
| MAGEB1 | MAGE-B1 |
| MAGEB2 | MAGE-B2 |
| MAGEC2 | MAGE-C2 |
| TP53 | |
| TYR | Tyrosinase |
| TYRP1 | TRP-1 |
| SAGE1 | SAGE |
| SYCP1 | HOM-TES-14/SCP1 |
| SSX2 | SSX2 or HOM-MEL-40 |
| SSX4 | |
| KRAS | K-ras |
| PRAME | |
| NRAS | N-ras |

TABLE 1-continued

| Antigen Name | Common Name |
|---|---|
| ACTN4 | Alpha-actinin-4 |
| CTNNB1 | |
| CASP8 | Caspase-8 |
| CDC27 | |
| CDK4 | |
| EEF2 | |
| FN1 | Fibronectin |
| HSPA1B | Hsp70 |
| LPGAT1 | KIAA0205 |
| ME1 | Malic enzyme |
| HHAT | MART-2 |
| TRAPPC1 | MUM-2 |
| MUM3 | MUM-3 |
| MYO1B | Unconventional myosin class I gene |
| PAPOLG | neo-PAP |
| OS9 | OS-9 |
| PTPRK | Receptor-like protein tyrosine phosphatase kappa |
| TPI1 | Triosephosphate isomerase or TPI1 |
| ADFP | Perilipin-2 |
| AFP | Alpha-fetoprotein |
| AIM2 | |
| ANXA2 | Annexin II |
| ART4 | Endoplasmic reticulum-resident protein |
| CLCA2 | |
| CPSF1 | CPSF |
| PPIB | Cyclophilin B |
| EPHA2 | EphA2 |
| EPHA3 | EphA3 |
| FGF5 | Fibroblast growth factor 5 or FGF5 |
| CA9 | Carbonic anhydrase IX |
| TERT | hTERT |
| MGAT5 | GNT-V or N-acetylglucosaminytransferase V |
| CEL | intestinal carboxylesterase |
| F4.2 | |
| CAN | CAN protein |
| ETV6 | TEL1 or ETV6 |
| BIRC7 | Livin/ML-IAP |
| CSF1 | Macrophage colony stimulating factor |
| OGT | |
| MUC1 | Mucin or MUC1 |
| MUC2 | |
| MUM1 | MUM-1 |
| CTAG1 | NY-ESO-1 or LAGE-2 |
| CTAG2 | NY-ESO-ORF2 or LAGE-1 |
| CAMEL | |
| MRPL28 | Melanoma antigen p15 |
| FOLH1 | Prostate-specific membrane antigen |
| RAGE | |
| SFMBT1 | Renal ubiquitous protein 1 |
| KAAG1 | RU2AS |
| SART1 | SART-1 |
| TSPYL1 | SART-2 |
| SART3 | |
| SOX10 | |
| TRG | |
| WT1 | |
| TACSTD1 | Ep-CAM |
| SILV | Pmel 17 or gp100 |
| SCGB2A2 | Mammaglobin A |
| MC1R | |
| MLANA | MART-1 or Melan-A |
| GPR143 | OA1 |
| OCA2 | P polypeptide |
| KLK3 | PSA or Prostate-specific antigen |
| SUPT7L | ART-1 |
| ARTC1 | |
| BRAF | |
| CASP5 | Caspase-5 |
| CDKN2A | |
| UBXD5 | COA-1 |
| EFTUD2 | Elongation factor Tu GTP binding domain containing or SNRP116 |
| GPNMB | |
| NFYC | |

TABLE 1-continued

| Antigen Name | Common Name |
|---|---|
| PRDX5 | Peroxiredoxin 5 |
| ZUBR1 | E3 ubiquitin-protein ligase UBR4 |
| SIRT2 | |
| SNRPD1 | |
| HERV-K-MEL | |
| CXorf61 | Kita-kyushu lung cancer antigen 1; |
| CCDC110 | KM-HN-1 |
| VENTXP1 | NA88-A |
| SPA17 | Sperm protein 17 |
| KLK4 | |
| ANKRD30A | NY-BR-1 |
| RAB38 | NY-MEL-1 or RAB38 |
| CCND1 | Cyclin D1 |
| CYP1B1 | P450 1B1 or CYP1B1 |
| MDM2 | |
| MMP2 | Matrix metalloproteinase-2 |
| ZNF395 | Papillomavirus binding factor (PBF) |
| RNF43 | |
| SCRN1 | Secernin 1 |
| STEAP1 | STEAP |
| 707-AP | |
| TGFBR2 | TGF-beta receptor type IIB |
| PXDNL | MG50 |
| AKAP13 | Lymphoid blast crisis oncogene (Lbc) oncoproptein |
| PRTN3 | Proteinase 3 |
| PSCA | Prostate stem cell antigen |
| RHAMM | RHAMM/CD168 |
| ACPP | Prostatic acid phosphatase |
| ACRBP | OY-TES-1 |
| LCK | Lck |
| RCVRN | Recoverin |
| RPS2 | Ribosomal protein S2 |
| RPL10A | Ribosomal protein L10a |
| SLC45A3 | Prostein |
| BCL2L1 | Bcl-xL |
| DKK1 | Dickkopf-1 (DKK1) |
| ENAH | Human Mena protein |
| CSPG4 | Melanoma-associated chondroitin sulfate proteoglycan (MCSP) |
| RGS5 | |
| BCR | Breakpoint cluster region |
| BCR-ABL | |
| ABL-BCR | |
| DEK | DEK oncogene |
| DEK-CAN | |
| ETV6-AML1 | |
| LDLR-FUT | |
| NPM1-ALK1 | |
| PML-RARA | |
| SYT-SSX1 | |
| SYT-SSX2 | |
| FLT3 | FLT1 |
| ABL1 | Proto-oncogene tyrosine-protein kinase ABL1 |
| AML1 | AML |
| LDLR | Low density lipid receptor (LDLR) |
| FUT1 | GDP-L-fucose |
| NPM1 | NPM |
| ALK | |
| PML1 | promyelocytic leukemia or PML |
| RARA | RAR alpha |
| SYT | |
| SSX1 | |
| MSLN | Mesothelin |
| UBE2V1 | Ubiquitin-conjugating enzyme variant Kua |
| HNRPL | |
| WHSC2 | |
| EIF4EBP1 | |
| WNK2 | |
| OAS3 | |
| BCL-2 | Bcl-2 |
| MCL1 | Mcl-1 |
| CTSH | Cathepsin H |
| ABCC3 | Multidrug resistance-associated protein 3 (MRP3) |
| BST2 | HM1.24 |
| MFGE8 | Milk fat globule membrane protein BA46 (lactadherin) |
| TPBG | 5T4 oncofetal antigen |
| FMOD | Fibromodulin (FMOD) |
| XAGE1 | XAGE antigen |
| RPSA | Oncofetal Ag immature laminin receptor (OFA-iLR) |
| COTL1 | Coactosin-like 1 |
| CALR3 | CRT2 |
| PA2G4 | ErbB3-binding protein 1 |
| EZH2 | Polycomb group protein enhancer of zeste homolog 2 (EZH2) |
| FMNL1 | Formin-related protein in leukocytes 1 (FMNL1) |
| HPSE | Heparanase |
| APC | |
| UBE2A | |
| BCAP31 | |
| TOP2A | |
| TOP2B | |
| ITGB8 | |
| RPA1 | |
| ABI2 | |
| CCNI | |
| CDC2 | |
| SEPT2 | |
| STAT1 | |
| LRP1 | |
| ADAM17 | |
| JUP | |
| DDR1 | |
| ITPR2 | |
| HMOX1 | heme oxygenase-1 (HO-1) |
| TPM4 | Tropomyosin-4 |
| BAAT | |
| DNAJC8 | |
| TAPBP | |
| LGALS3BP | Mac-2-binding protein |
| PAGE4 | PAGE-4 |
| PAK2 | P21-activated serin kinase 2 (PAK2) |
| CDKN1A | cyclin-dependent kinase inhibitor 1A (CDKN1A) |
| PTHLH | Parathyroid hormone-related protein (PTHrP) |
| SOX2 | |
| SOX11 | |
| TRPM8 | Prostate-specific protein transient receptor potential-p8 (trp-p8) |
| TYMS | Thymidylate synthase (TYMS) |
| ATIC | 5'-aminoimidazole-4-carboxamide-1-beta-d-ribonucleotide transfolmylase/inosinicase (AICRT/I) |
| PGK1 | phosphoglycerate kinase 1 (PKG1) |
| SOX4 | SOX-4 |
| TOR3A | ATP-dependent interferon-responsive (ADIR) |
| TRGC2 | T-cell receptor gamma alternate reading frame protein (TARP) |
| BTBD2 | BTB domain containing 2 (BTBD2) |
| SLBP | hairpin-binding protein |
| EGFR | Epidermal growth factor receptor (EGFR) |
| IER3 | immediate early response gene X-1 (IEX-1) |
| TTK | TTK protein kinase (TTK) |
| LY6K | lymphocyte antigen 6 complex locus K (LY6K) |
| IGF2BP3 | insulin-like growth factor (IGF)-II mRNA binding protein 3 (IMP-3) |
| GPC3 | glypican-3 (GPC3) |
| SLC35A4 | |
| HSMD | HMSD-v-encoded mHA |
| H3F3A | |
| ALDH1A1 | aldehyde dehydrogenase 1 family member A1 (ALDH1A1) |
| MFI2 | Melanotransferrin |
| MMP14 | |
| SDCBP | |
| PARP12 | |
| MET | c-Met protein |
| CCNB1 | cyclin B1 |
| PAX3-FKHR | |
| PAX3 | |
| FOXO1 | FKHR |
| XBP1 | XBP1 |
| SYND1 | CD138 |
| ETV5 | |
| HSPA1A | |
| HMHA1 | |
| TRIM68 | |
| ACSM2A | ACSM2A |
| ATR | ATR |

TABLE 1-continued

| Antigen Name | Common Name |
|---|---|
| USB1 | USB1 |
| RTCB | RTCB |
| C6ORF89 | C6ORF89 |
| CDC25A | CDC25A |
| CDK12 | CDK12 |
| CRYBA1 | CRYBA1 |
| CSNK1A1 | CSNK1A1 |
| DSCAML1 | DSCAML1 |
| F2R | F2R |
| FNDC3B | FNDC3B |
| GAS7 | GAS7 |
| HAUS3 | HAUS3 |
| HERC1 | HERC1 |
| HMGN2 | HMGN2 |
| SZT2 | SZT2 |
| LRRC41 | LRRC41 |
| MATN2 | Matrilin-2 |
| NIN | Ninein |
| PLEKHM2 | PLEKHM2 |
| POLR2A | POLR2A |
| PPP1R3B | PPP1R3B |
| RALGAPB | RALGAPB |
| SF3B1 | SF3B1 |
| SLC46A1 | SLC46A1 |
| STRAP | STRAP |
| SYT15 | SYT15 |
| TBC1D9B | TBC1D9B |
| THNSL2 | THNSL2 |
| THOC6 | THOC6 |
| WHSC1L1 | WHSC1L1 |
| XPO1 | XPO1 |
| BCL11A | BCL11A |
| SPEN | SPEN |
| VPS13D | VPS13D |
| SOGA1 | SOGA1 |
| MAP1A | MAP1A |
| ZNF219 | ZNF219 |
| SYNPO | SYNPO |
| NFATC2 | NFATC2 |
| NCBP3 | NCBP3 |
| HIVEP2 | HIVEP2 |
| NCOA1 | NCOA1 |
| LPP | LPP |
| ARID1B | ARID1B |
| SYNM | SYNM |
| SVIL | SVIL |
| SRRM2 | SRRM2 |
| RREB1 | RREB1 |
| EP300 | EP300 |
| RCSD1 | RCSD1 |
| CEP95 | CEP95 |
| IP6K1 | IP6K1 |
| RSRP1 | RSRP1 |
| MYL9 | MYL9 |
| TBC1D10C | TBC1D10C |
| MACF1 | MACF1 |
| MAP7D1 | MAP7D1 |
| MORC2 | MORC2 |
| RBM14 | RBM14 |
| GRM5 | GRM5 |
| NIFK | NIFK |
| TLK1 | TLK1 |
| IRS2 | IRS2 |
| PPP1CA | PPP1CA |
| GPSM3 | GPSM3 |
| SIK1 | SIK1 |
| HMGN1 | HMGN1 |
| MAP3K11 | MAP3K11 |
| GFI1 | GFI1 |
| KANSL3 | KANSL3 |
| KLF2 | KLF2 |
| CCDC88B | CCDC88B |
| TNS3 | TNS3 |
| N4BP2 | N4BP2 |
| TPX2 | TPX2 |
| KMT2A | KMT2A |
| SRSF7 | SRSF7 |
| GRK2 | GRK2 |
| GIGYF2 | GIGYF2 |
| SCAP | SCAP |
| MIIP | MIIP |
| ZC3H14 | ZC3H14 |
| ZNF106 | ZNF106 |
| SKI | SKI |
| SETD2 | SETD2 |
| ATXN2L | ATXN2L |
| SRSF8 | SRSF8 |
| LUZP1 | LUZP1 |
| KLF10 | KLF10 |
| RERE | RERE |
| MEF2D | MEF2D |
| PCBP2 | PCBP2 |
| LSP1 | LSP1 |
| MEFV | MEFV |
| ARHGAP30 | ARHGAP30 |
| CHAF1A | CHAF1A |
| FAM53C | FAM53C |
| ARHGAP17 | ARHGAP17 |
| HSPB1 | HSPB1 |
| NCOR2 | NCOR2 |
| ATXN2 | ATXN2 |
| RBM15 | RBM15 |
| RBM17 | RBM17 |
| SON | SON |
| TSC22D4 | TSC22D4 |
| MYC | MYC |
| ANKRD17 | ANKRD17 |

In certain embodiments, the antigen employed in the complexes described herein is from a human oncogenic or tumor virus. Viruses that are associated with human malignancies include: HTLV-1 (adult T-cell leukemia (ATL), HPV (cervical cancer, skin cancer in patients with epidermodysplasia verruciformis (EV), head and neck cancers, and other anogenital cancers); HHV-8 (Kaposi's sarcoma (KS), primary effusion lymphoma, and Castleman's disease), EBV (Burkitt's Lymphoma (BL), nasopharyngeal carcinoma (NPC), MCPyV (Merkel Cell Carcinoma), post-transplant lymphomas, and Hodgkin's disease), HBV, and HCV (hepatocellular carcinoma (HCC)). Additionally, viruses with possible roles in human malignancies include: simian vacuolating virus 40 (SV40) (brain cancer, bone cancer, and mesothelioma), BK virus (BKV) (prostate cancer), JC virus (JCV) (brain cancer), human endogenous retroviruses (HERVs) (germ cell tumors, breast cancer, ovarian cancer, and melanoma), human mammary tumor virus (HMTV) (breast cancer), and (vi) Torque teno virus (TTV) (gastrointestinal cancer, lung cancer, breast cancer, and myeloma).

In certain embodiments, antigens from viruses or bacteria are employed with the nano-satellite complexes described herein. Such antigens are well known in the art. Examples of viruses (Table 2) and bacteria (Table 3) that are the source of such well-known antigens are provided below.

TABLE 2

| Viral diseases | |
|---|---|
| Virus antigen source | Diseases or conditions |
| Hepatitis A virus | Hepatitis A |
| Hepatitis B virus | Hepatitis B |
| Hepatitis E virus | Hepatitis E |
| Human papillomavirus | Cervical cancer, Genital warts, anogenital cancers |
| Influenza virus | Influenza |
| Japanese encephalitis virus | Japanese encephalitis |
| Measles virus | Measles |

TABLE 2-continued

Viral diseases

| Virus antigen source | Diseases or conditions |
| --- | --- |
| Mumps virus | Mumps |
| Polio virus | Poliomyelitis |
| Rabies virus | Rabies |
| Rotavirus | Rotaviral gastroenteritis |
| Rubella virus | Rubella |
| Tick-borne encephalitis virus | Tick-borne encephalitis |
| Varicella zoster virus | Chickenpox, Shingles |
| Variola virus | Smallpox |
| Yellow fever virus | Yellow fever |

TABLE 3

Bacterial diseases

| Bacterium antigen source | Diseases or conditions |
| --- | --- |
| *Bacillus anthracis* | Anthrax |
| *Bordetella pertussis* | Whooping cough |
| *Clostridium tetani* | Tetanus |
| *Corynebacterium diphtheriae* | Diphtheria |
| *Coxiella burnetii* | Q fever |
| *Haemophilus influenzae* type B (Hib) | Epiglottitis, meningitis, pneumonia |
| *Mycobacterium tuberculosis* | Tuberculosis |
| *Neisseria meningitidis* | Meningococcal meningitis |
| *Salmonella typhi* | Typhoid fever |
| *Streptococcus pneumoniae* | Pneumococcal pneumonia |
| *Vibrio cholerae* | Cholera |

EXAMPLES

Example 1

Virus-Like Nanoparticles for Antigen-Specific Antibody Production

This Examples describes the production and use of virus-like nanoparticles to produce antibodies.

Materials: All reagents were used as obtained from commercial sources without further purification. Iron oxide (III) (FeO(OH), hydrated, catalyst grade, 30-50 mesh), oleic acid (technical grade, 90%), 1-octadecene (technical grade, 90%), anhydrous tetrahydrofuran (THF, 99.8%), sodium sulfide, chloroauric acid, ammonium iron (II) sulfate hexahydrate (Fe(NH$_4$)$_2$(SO$_4$)$_2$·6H$_2$O, ACS reagent, 99%), nitric acid (ACS reagent, 70%), and hydrochloric acid (ACS reagent, 37%) were purchased from Sigma-Aldrich. Mouse uncoated IgG and IgM Total ELISA Ready-SET-Go! Kits, 1-Step Ultra TMB-ELISA substrate solution, HRP-conjugated goat anti-mouse IgG1 secondary antibody, HRP-conjugated goat anti-mouse IgG2a secondary antibody, Nunc Immobilizer Amino 96-well ELISA plates, BupH carbonate bicarbonate buffer packs (coating buffer), Pierce protein free PBS tween blocking buffer, 20×PBS-tween wash buffer, Geneticin (G418) selective antibiotic, Invitrogen eBioscience fixable viability dye eFluor 780, and Molecular Probes streptavidin Alexa Fluor 647 conjugate were obtained from Thermo Fisher Scientific. HRP conjugated goat anti-mouse IgG secondary antibody, Zombie UV fixable viability kit, FITC anti-mouse CD19, PE/Dazzle 594 anti-mouse CD38, Brilliant Violet 421 anti-mouse CD138, PE/Dazzle 594 anti-mouse IgD, Alexa Fluor 647 anti-mouse/house GL7 antigen, Brilliant Violet 421 and PE/Dazzle 594 anti-mouse/human CD45R/B220, FITC anti-mouse CD95, Brilliant Violet 421 anti-mouse/human CD11b, FITC anti-mouse CD169, PE/Dazzle 594 anti-mouse CD11c were purchased from BioLegend. HER2 peptides (CDDDPESFDGDPASN-TAPLQPEQLQ (SEQ ID NO: 1), Biotin-PESFDGDPASN-TAPLQPEQLQ (SEQ ID NO: 2), CDDDPESFDGDPASN-TAPLQPEQLQGGGK (SEQ ID NO: 3)) were custom synthesized. 30 nm iron-oxide nanoparticles cores stabilized by oleic acid in chloroform were purchased from Ocean Nanotech. DSPE-PEG(2000) and DSPE-PEG(2000)maleimide were obtained from Avanti Polar Lipids. 2'3'-cGAMP was acquired from InvivoGen. Fluorescamine was purchased from MP Biomedicals. Sulfo-Cy5.5 NHS ester was acquired from Lumiprobe. Microvette 500 Z-Gel serum collection vials with clotting factor were obtained from Sarstedt. Matrigel Basement Membrane Matrix was purchased from Corning. Gold and iron ICP standards were purchased from Fluka Analytical.

Mice. All animal experiments were conducted according to the protocols approved by the University of Michigan Committee on Use and Care of Animals (UCUCA). BALB/c mice ages 5-7 weeks were purchased from Charles River Labs.

Cells. All cells were maintained at 37 C, 5% CO$_2$/95% air atmosphere and approximately 85% relative humidity. D2F2/E2 cells were cultured in complete DMEM high glucose supplemented with 10% NCTC 109 media, 1% L-glutamine, 1% MEMs non-essential amino acids, 0.5% sodium pyruvate, 2.5% sodium bicarbonate, 1% pen/strep, 5% cosmic calf serum, 5% fetal bovine serum, 500 µg/mL Geneticin and 50 µM 2-mercaptoethanol. RAW264.7 macrophages were cultured in complete RPMI-1640 media supplemented with 10% fetal bovine serum, 1% L-glutamine, 1% MEMs non-essential amino acids, 1% sodium pyruvate and 1% pen/strep. DC2.4 dendritic cells were cultured in RPMI-1640 media supplemented with 10% fetal bovine serum, 1% L-glutamine, 1% MEMs non-essential amino acids, 1% HEPES buffered solution, 1% pen/strep and 50 µM 2-mercaptoethanol.

Formulation and Characterization of Inorganic Virus-Like Nanoparticles (IVLN). The IVLN was formulate as follows.

Synthesis of IONPs Coated with Polysiloxane-Containing Diblock Copolymer. Spherical IONPs (15 nm in diameter) were synthesized in organic solvent by thermal decomposition. Cubic IONPs (25 nm in edge length) were also synthesized. Diblock copolymer (PEO-b-P$_f$MPS) was synthesized by the reversible addition of fragmentation chain transfer (RAFT) polymerization. The preparation of the polymer-coated MNPs with either single or clustered core was performed. The IONP iron concentration was determined using o-phenanthroline (ACS reagent, 99%) after digestion with hydrochloric acid (ACS reagent, 37%). General methods of such synthesis are found in Chen et al., ACS Appl. Mater. Interfaces 2015, 7, 12814-12823, herein incorporated by reference.

Synthesis of AuNPs. AuNPs were synthesized by using sodium sulfide (Na$_2$S) as the reducing reagent. Gold in the form of chloroauric acid (HAuCl$_4$) was prepared to a concentration of 100 mM as a stock solution and was diluted to 2.0 mM before use. Na$_2$S (50 mM) was prepared and aged in the dark for 40-48 h prior to use and was diluted to 1.0 mM before use. The volume ratio of Na$_2$S to HAuCl$_4$ was varied from 2.5/1.0 to 3.0/1.0. UV/Vis spectra were recorded to monitor the reaction. Without specification, the reaction with a volume ratio of 3.0/1.0 was chosen to use in the following steps. General methods of such synthesis are found in Chen et al., ACS Appl. Mater. Interfaces 2015, 7, 12814-12823, herein incorporated by reference.

Synthesis of Inorganic Virus-Like Nanoparticles (IVLN). IVLNs were made by incubating AuNPs with polymer-coated IONPs at 4° C. In a typical experiment, two milligram Fe of IONPs (0.5 mL) was mixed with AuNP solution 6 mL of for spherical IONPs and 4 mL for cubic IONPs, respectively, if without specification. The formed IVLNs were purified by magnet to remove unbound AuNPs after overnight incubation.

The final Au:Fe ratio of the formulated IVLN was quantified by inductively coupled plasma mass spectrometry using a Perkin-Elmer Nexion 2000 based on established protocols. IVLN formulations were imaged by transmission electron microscopy (TEM) using the JEOL 3011 High Resolution Electron Microscope. The true particle size of AuNPs, IONPs and IVLNs was quantified using ImageJ software. The volume-weighted hydrodynamic particle size, polydispersity index and zeta-potential of all formulations in milliQ water at 25° C. was evaluated with the Malvern Zetasizer Nano-ZS using dynamic light scattering and phase analysis light scattering, respectively.

Lipid-Coated Iron-Oxide Nanoparticle Formulations (Lipid-IONP). Lipid-coated iron-oxide nanoparticles were prepared based on previously reported methods for thin-film hydration with minor modifications. 10 mg of DSPE-PEG (2000)-maleimide was added to 1 mg of 30-nm iron-oxide nanoparticle cores stabilized by oleic acid in chloroform as gently mixed. The resulting solution was subjected to solvent rotary evaporation to remove all chloroform and form a thin film. Simultaneously, this film and 100 mM PBS, pH 7.4 were heated to 75° C. in an oven. Upon reaching temperature, hot PBS was rapidly added to the film and mixed immediately and vigorously to facilitate thin film hydration. The resulting nanoparticle solution was stored at 4° C. to promote lipid self-assembly. Free phospholipids were removed by magnetic separation overnight at 4° C. using the a magnetic separator device.

Lipid-IONP-HER2 and IVLN-HER2 Formulations. HER2 peptides were conjugated to both Lipid-IONP and IVLN through thiol-mediated chemistries. Specifically, Lipid-IONP-HER2 was formulated via maleimide chemistry and IVLN-HER2 was formulated via the gold-thiol linkage. HER2 peptide was added to Lipid-IONP at 1.5× weight ratio excess in milliQ and incubated overnight at 4° C. HER2 peptide was added to IVLN-HER2 at 5× weight ratio excess in milliQ and incubated overnight at 4° C. Both materials were purified either by magnetic separation overnight at 4° C. using a magnetic separator device, or by centrifugal separation at 10,000×g for 30 minutes at 4° C.

Immunizations and Serum Collection. At day 0, mice were immunized with the equivalent of 50 µg of HER2 peptide plus 10 µg of cGAMP regardless of formulation type. Subsequently, at day 14, mice were boosted twice at two-week intervals with 50% of the original dosage for both antigen and adjuvant (day 14 and 28). To evaluate serum antibody titers, blood was collected by submandibular puncture 10 days after each immunization (day 10, 24 and 38). Serum was separated from whole blood by centrifugal separation at 10,000×g for 5 minutes at 25° C. using the Microvette 500 Ser-Gel collection vessels with clotting activator.

Enzyme-Linked Immunosorbent Assay (ELISA). Absolution quantification of total IgG and total IgM antibody analysis was performed using the mouse uncoated total IgG and total IgM ELISA kits based on protocols provided by ThermoFisher. Antigen-specific IgG, IgG1 and IgG2a antibody titers were quantified based on previously established protocols for indirect ELISA with minor modifications. Specifically, HER2 peptides (200 µL, 100 ug/mL in 100 mM carbonate buffer, pH 9.4) were chemically conjugated to ELISA plates through the terminal amine group utilizing Nunc Immobilizer Amino immunoassay plates by overnight incubation with exposure to light at room temperature. Following overnight incubation, ELISA plates were washed three times with 100 mM PBS, pH 7.4 with 2% Tween-20. Subsequently, ELISA plates were blocked overnight at 4° C. with 300 µL of ELISA blocker (Pierce Protein-Free PBS Blocking Buffer). Following blocking, the ELISA plates were washed 3×. Serum samples containing primary antibodies were serially diluted ($10^1$-$10^8$ fold) using 100 mM PBS, pH 7.4 containing 10% ELISA blocker reagent and added to each well at 2004 total for 2 hour incubation at room temperature. Following sample addition, the ELISA plates were washed 3×. 500-fold diluted anti-IgG-HRP, anti-IgG1-HRP, or anti-IgG2a-HRP was added at 1004 to each well and incubated for 1 hour at room temperature. After 1 hour, the ELISA plates were washed 5×. Next, 1004 of 1-Step Ultra TMB Substrate Solution was added to each well and allowed to incubate and develop color for 15-20 minutes at room temperature with gentle agitation. After 15-20 minutes, color development was stopped by the addition of 1004 of 100 mM sulfuric acid. Colorimetric development was quantified by absorbance spectroscopy at 450 nm using a BioTek Cytation 5. Antibody titers were determined by any absorbance signal at a given dilution factor that was greater than the PBS control absorbance signal plus 3× standard deviations.

Quantification of Nanoparticle Delivery to Lymph Nodes in-vivo. Mice were injected subcutaneously in the left hock with either Lipid-IONP or IVLN-peptide at 200 µg total Fe per mouse. At the designated time intervals, mice were sacrificed, and lymph nodes of interest were dissected for ex-vivo analysis. The extent of nanoparticle delivery to the lymph nodes was quantified using ICP-MS based on previously reported protocols.

Quantification of Peptide Delivery to Lymph Nodes in-vivo. To facilitate quantification of peptide delivery to lymph nodes, lysine terminally modified HER2 peptides were chemically conjugated to sulfo-Cy5.5 NHS Ester. This conjugation was carried out at a 5-fold molar excess of sulfo-Cy5.5 NHS Ester to HER2 peptide. IONP-HER2-Cy5.5 and IVLN-HER2-Cy5.5 were subjected to Cy5.5 functionalization after initial peptide conjugation was completed in order to enable facile purification of excess fluorescent dye by magnetic separation. Subsequent to Cy5.5 functionalization, mice were injected as previously stated. After 3 hours, mice were sacrificed and lymph nodes of interest were dissected for ex-vivo analysis by IVIS imaging. IVIS imaging was utilized for semi-quantification of peptide delivery in terms of radiant efficiency.

In-vitro Cell Uptake. IVLN-HER2 and IONP-HER2 cellular uptakes was evaluated in RAW264.7 macrophages, DC2.4 dendritic cells and primary B-cells isolated from murine spleens using an EasySep Mouse B-cell isolation kit. Nanoparticle samples were incubated at 50 µg/mL Fe with cells for 18 hours in blank RPMI media at 37 C, 5% $CO_2$/95% air atmosphere and approximately 85% relative humidity. After 18 hours, cells were lifted by cell scraping and washed thrice with phosphate-buffered saline (PBS). Following the wash steps, resulting cell pellets were re-suspend in 1 mL of PBS, cell counted and then digested in 1 mL aqua regia (1:3 molar ratio nitric acid:hydrochloric acid) for analysis by ICP-MS.

In-vivo Cell Uptake. IVLN-HER-Cy5.5 and IONP-HER2-Cy5.5 were injected subcutaneously in the left hock with either Lipid-IONP or IVLN at 200 μg total Fe per mouse. At 3 hours and 24 hours, mice were sacrificed and lymph nodes of interest were dissected for ex-vivo analysis by flow cytometry. Lymph nodes were dissociated by mechanical methods to prepare single cell suspensions. Single cell suspensions of lymph node cells were stained for analysis by flow cytometry using the MoFlo Astrios flow cytometer. The first panel was for viable cells, B-cells ($B220^+$), subcapsular sinus macrophages ($CD169^+CD11b^+$), dendritic cells ($CD11c^+$) and nanoparticle positive cells (Cy5.5). Flow cytometry data was analyzed by FCS express.

Antigen-Specific B-cell and Germinal Center Flow Cytometry. Mice were immunized as previously introduced. At day 24 and day 38, mice were sacrificed and spleens and lymph nodes were dissected for ex-vivo analysis by flow cytometry. Antigen-specific B-cell analysis was accomplished using tetramer staining. HER2/neu peptide tetramers were prepared by mixture of biotin-labeled HER2 peptide with Alexa Fluor 647 labeled streptavidin at a 4:1 molar ratio at room temperature for 1 hour without further purification. Antigen-specific B-cell population were identified as either memory B-cells ($B220^+CD38^+$ $Tetramer^+$) or plasma cells ($B220^-CD138^+$ $Tetramer^+$) using flow cytometry. Germinal center B-cell populations were identified using the following markers CD19, IgD, GL7 and CD95.

Tumor Studies. Sixty days after the primary immunization, mice were inoculated with 500,000 D2F2/E2 cells subcutaneously in the right flank. D2F2/E2 cells were prepared at 5e6 cells/mL in 100 μL and mixed at equal volume with Matrigel matrix. Tumor size was quantified by caliper measurements every 7 days. Tumor volumes were calculated using the following equation:

Tumor Volume=$xy^2/2$

End points were determined by using the End-Stage Illness Scoring System; mice receiving an End-Stage Illness Score greater than 6 were euthanized by $CO_2$ asphyxiation.

Statistics. Data are expressed as mean±standard deviation (SD), unless otherwise specified. Comparisons between two groups were made using the unpaired Student's t-test. Means of multiple groups were compared with the one-way analysis of variance (ANOVA), followed by post hoc Tukey's pairwise comparisons. All probability values are two-sided, and values of $p<0.05$ were considered statistically significant. Statistical analyses were carried out using the GraphPad Prism 7 software package.

Results

Inorganic Virus-Like Nanoparticle (IVLN) Formulation and Viral Properties

Figure 1:
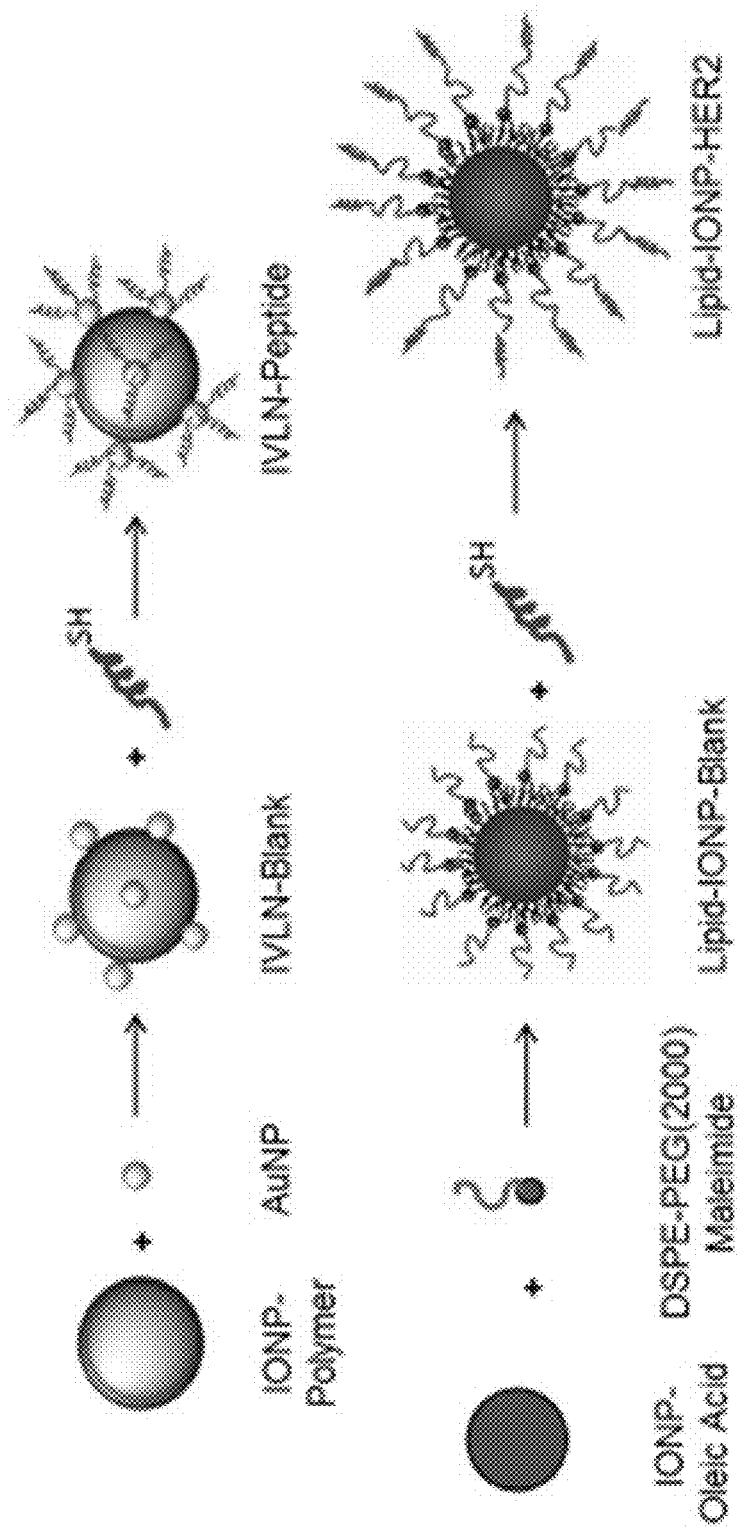
FIG. 1, top shows a simplified schematic for generating an exemplary inorganic virus-like nanoparticle (IVLN) blank and IVLN-peptide complex.
Figure 2B:
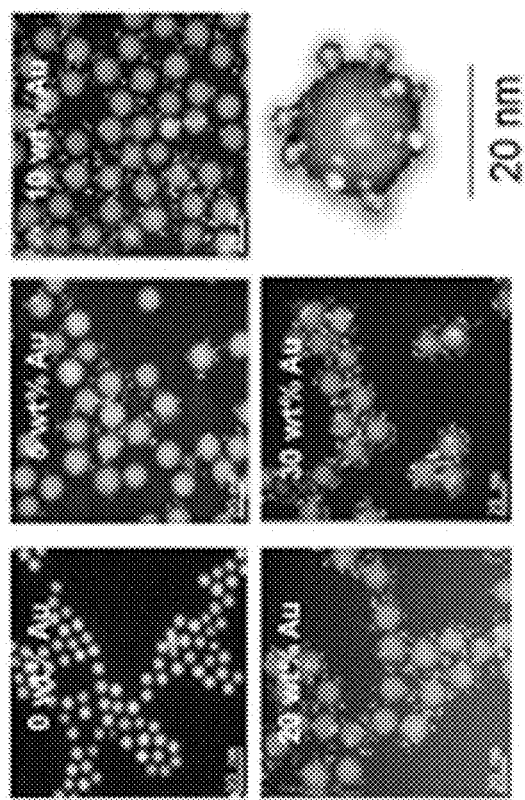
FIG. 2B shows TEM imaging of the IVLN at different formulation conditions.
Figure 2A:
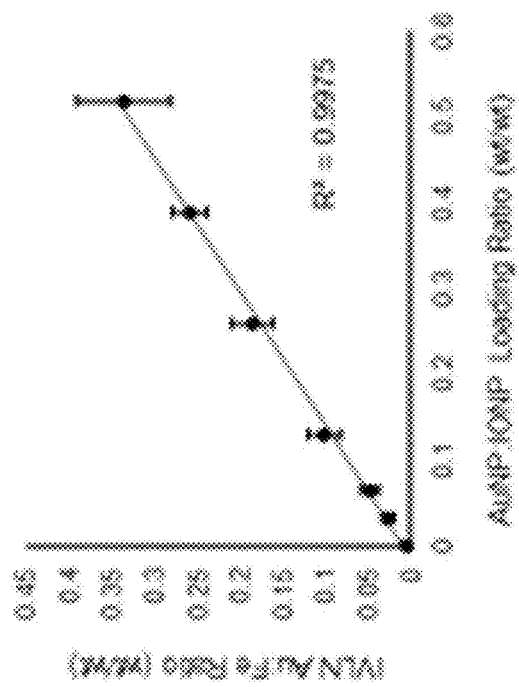
FIG. 2A shows the IVLN formulation conditions and loading efficiency of satellite particles on iron-oxide nanoparticle cores.

The IVLN is formulated by the self-assembly of two separately prepared nanoparticle systems, an iron-oxide nanoparticle core and gold nanoparticle satellites, through the association of hydrolyzed siloxane groups and gold (FIG. 1). The iron-oxide nanoparticle (IONP) core was synthesized by thermal decomposition to produce a ~15-nm spherical core stabilized by oleic acid in chloroform. To achieve aqueous stabilization, the IONP core was coated with a polysiloxane/PEG diblock copolymer (IONP-polymer). Separately, ultra-small gold nanoparticles (AuNP) with ~3 nm size were prepared using a modified self-assembly method by reduction of chloroauric acid in aged sodium sulfide. Following synthesis, AuNPs are added to the polymer-coated IONP cores in solution at defined weight ratios. To quantify the extent of AuNP loading per IONP core following self-assembly, inductively coupled plasma mass spectrometry (ICP-MS) was used. With ICP-MS, it was determined that the average loading efficiency on a per weight basis was 73±7% with a linear dependence ($R^2=0.997$) (FIG. 2A). Notably, above an initial loading ratio of 50% weight Au, destabilization of nanoparticles in solution was observed, and was therefore not the focus of further research. To provide visual confirmation of AuNP and IONP-polymer self-assembly to form the IVLN, transmission electron microscopy (TEM) was performed (FIG. 2B). TEM imaging confirmed that by controlling the initial loading ratio of AuNP to IONP-polymer cores on a per weight basis it is possible to yield IVLNs with variable gold nanoparticle surface density and viral-like character (FIG. 2B-insert). IONP-polymer core and AuNP diameters were quantified to be 15.9±1.3 nm and 2.3±0.4 nm, respectively. TEM imaging was further utilized to estimate the AuNP loading per IONP-polymer core. Specifically, 10%, 20% and 30% weight Au conditions yielded IVLNs with 4±2, 9±3 and 13±5 AuNPs per IONP-polymer core, respectively.

Figure 2D:
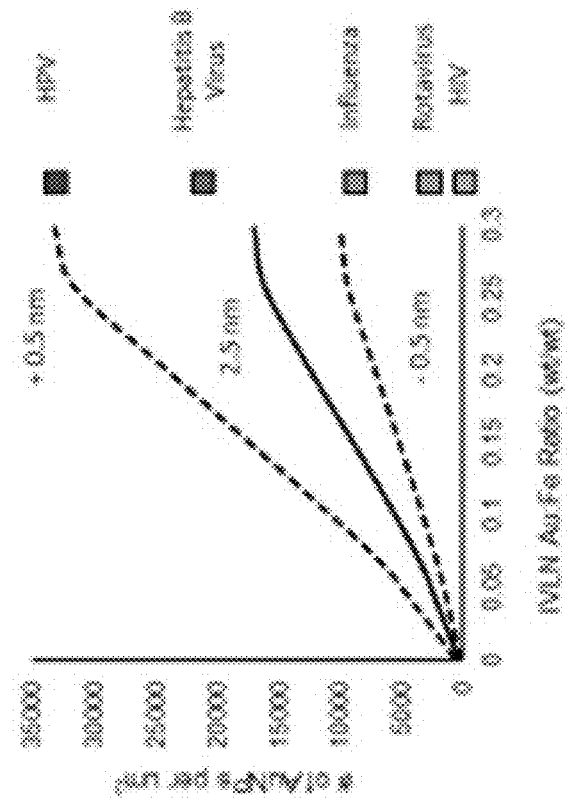
FIG. 2D shows mathematical modeling of satellite density on nanoparticle surfaces at different formulation conditions.
Figure 2C:
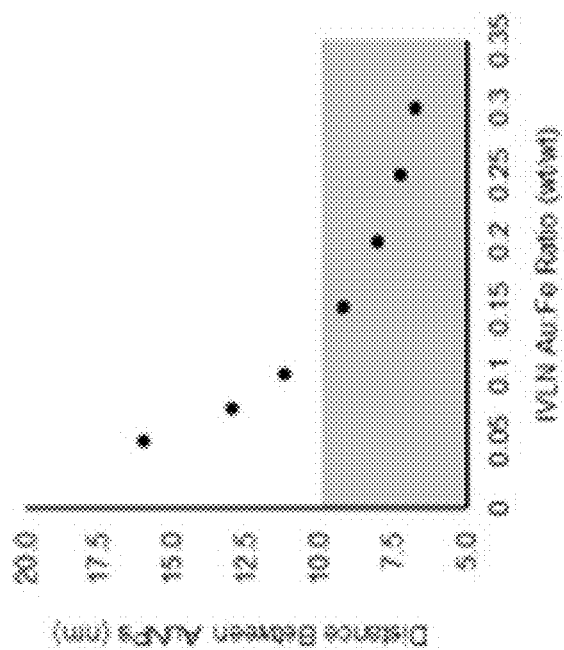
FIG. 2C shows mathematical modeling of distance between satellites at different formulation conditions.

Following ICP-MS quantification and TEM visualization of IVLN formulations, elementary mathematical modeling was performed in order to determine the structural relevance of IVLN as compared to virus-like particles. Given the crystalline nature of AuNPs and IONPs, it is feasible to determine the number of particles of a determined particle size for a given weight of either Au or Fe, respectively. Based on the ICP-MS measurements performed in FIG. 2A and the particle size confirmation by TEM in FIG. 2B, it is therefore possible to estimate the average distance between AuNPs on the IONP surface, as well as the average number of AuNPs per unit area on IONP surfaces. From this analysis, it was determined that depending on the initial weight loading ratio of Au to Fe, IVLNs can be formulated with a minimum average distance of 6.75 nm between AuNPs—a preferred distance for B-cell receptor crosslinking (FIG. 2C). In addition to AuNP spatial distribution, at this same initial loading ratio, the number of AuNPs per unit area was determined to be approximately 12,500-17,000 AuNPs per square micron—a value that compares favorable with the antigen density reported for viral-like particles (e.g. Hepatitis B Virus) (FIG. 2D).

To further evaluate the viral-like potential of the IVLN, we next evaluated the capacity for and mechanism of peptide loading in this system. The peptide of interest in these studies is a human HER2/neu-specific peptide that, based on previously published works, contains a B-cell epitope with an overlapping CD4 helper T-cell epitope. In addition to these functional epitopes, a cysteine containing terminal flank was added to facilitate facile loading to the IVLN via the Au—S linkage (CDDDPESFDGDPASNTAPLQPEQLQ, SEQ ID NO:1). The capacity for peptide conjugation to the IVLN was quantified utilizing a modified fluorescamine peptide assay. Peptide loading was evaluated under three separate IVLN formulation conditions: 0%, 10% and 30% Au to Fe final weight loading ratio (wt/wt Au/Fe). In terms of AuNPs per IONP-polymer core, these values approximately translate to 0 AuNPs, 4 AuNPs and 10 AuNPs per IONP-polymer core, respectively. Peptide conjugation was performed in water at 4° C. overnight with subsequent purification by centrifugal separations. Fluorescent peptide quantification analysis revealed that, at maximum peptide loading conditions, the 0%, 10% and 30% wt/wt formulations were loaded with 232±73, 888±42 and 1954±157 peptides per IVLN, respectively (FIG. 2E). When these same values were standardized by total AuNPs it was determined that maximum peptide loading per AuNP was 227±5. Additionally, this analysis revealed a positive correlation between peptide loading and AuNP number (R=0.95). Taken together, these results suggest although there is low-level non-specific physical association to the core (~12% under maximum loading conditions), peptide loading is AuNP dependent. Thus, peptide conjugation to IVLN surface is AuNP localized, which indicates that the IVLN-peptide is characterized by heterogeneous and patchy peptide distribution. This patterned antigen display is viral-like in nature and can not be reproduced by traditional nanoparticle systems that employ homogeneous antigen distribution on their surfaces.

Figure 2F:
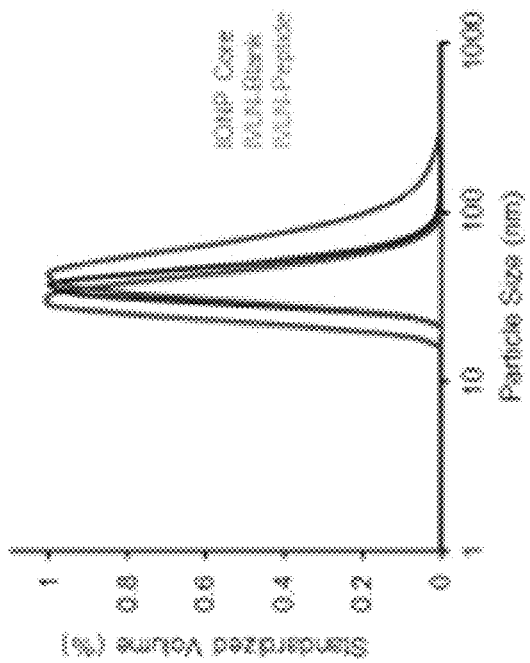
FIG. 2F shows the volume-weighted hydrodynamic particle distribution of IVLN at different stages of the formulation.
Figure 2E:
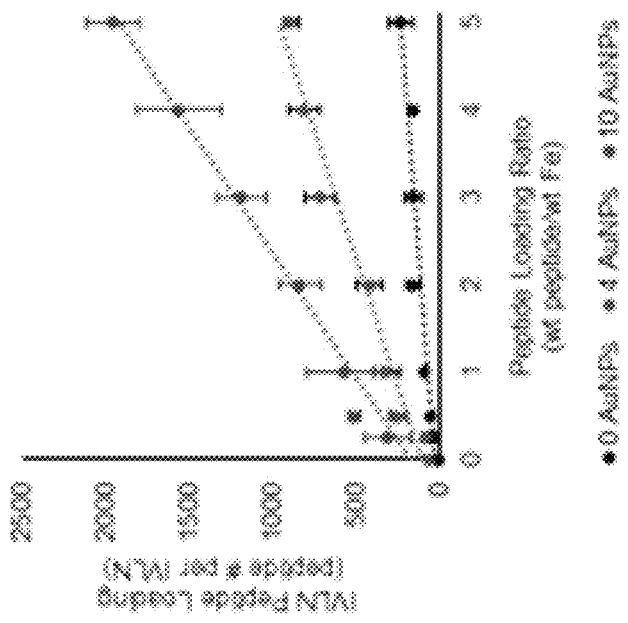
FIG. 2E shows peptide loading on IVLN surfaces and loading specificity to satellites.

After the evaluation of peptide loading, we next assessed the IVLN-peptide's material properties to determine if the material was suitable for in-vivo applications and appropriately aligned with viral-like properties (FIG. 2F). Before incubation with AuNPs, the IONP-polymer core of the IVLN was shown to have a 51±2 nm volume-weighted hydrodynamic particle size by dynamic light scattering (DLS) with a 0.15±0.03 polydispersity index (PDI). In addition, the zeta-potential of this material in milliQ water at pH 7 was determined to be −7±4 mV. Following formulation at a final weight loading ratio of 30% wt/wt Au/Fe, the IVLN-Blank was shown to have a 55±2 nm particle size, 0.20±0.05 PDI and a −16±4 mV zeta-potential before peptide loading. After peptide loading, the IVLN-Peptide was shown to have a 60±4 nm particle size, 0.20±0.05 PDI and a −17±1 mV zeta-potential. Taken together, the IVLN-peptide was determined to have optimal material properties for in-vivo applications. Moreover, these properties were deemed acceptably within the design criteria for viral mimicking nanoparticles, which includes particle size between 20-300 nm and negative overall surface charge.

Figure 3A:
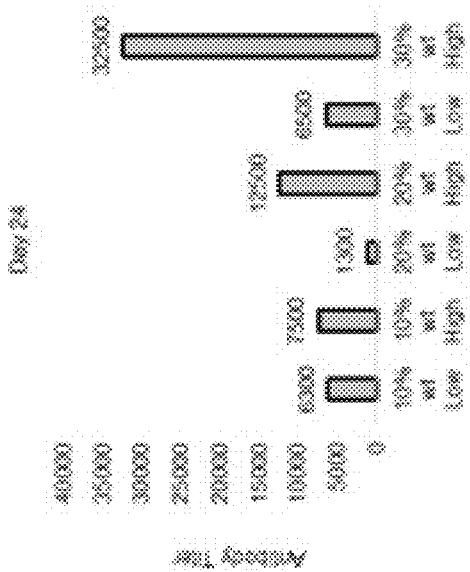
FIGS. 3A-C show results of Example 1 for antigen-specific antibody production in mice using IVLN-peptides.

Inorganic Virus-Like Nanoparticle (IVLN) for Antigen-Specific Antibody Production in Mice Viral mimicking nanoparticles have been utilized in a wide-range of in-vitro and in-vivo applications, but the one application that viral-like material properties are very good for is B-cell activation for antigen-specific antibody production. Accordingly, based on the establish viral-like material properties of IVLN-peptides. In this study, BALB/c mice (6-8 weeks old) were immunized with 50 µg of HER2 peptide plus 10 µg of cGAMP as adjuvant at day 0 and boosted once 14 days later. Mice were bled, and serum was collected for analysis 10-days following every administration (FIG. 3A).

Figure 3B:
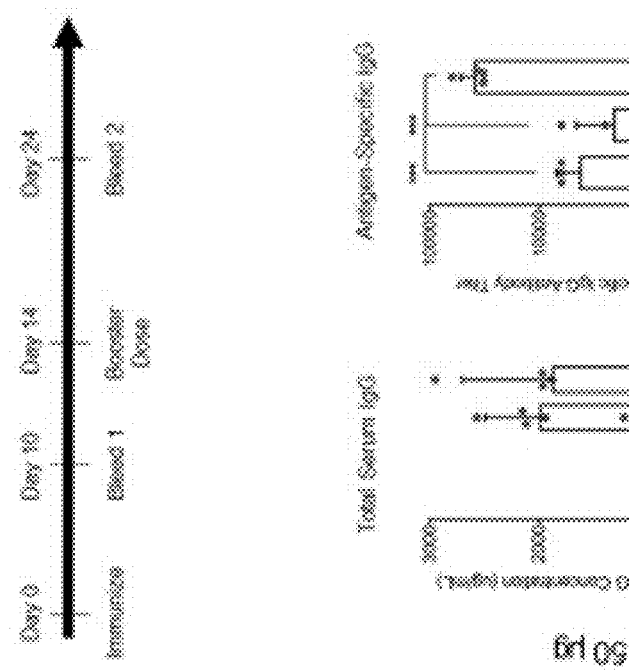

Based on an understanding of the requirement of B-cell receptor crosslinking for B-cell activation and germinal center formation, we first asked what the role of AuNP quantity and spatial distribution on IVLN surfaces at saturated peptide loading was. To answer this question, we evaluated the titer of antigen-specific IgG antibodies produced in mice after a booster immunization with IVLN at 10%, 20% and 30% wt/wt Au/Fe final weight loading ratios by indirect ELISA. From this analysis, it was determined that by day 24 the production of antigen-specific IgG, in terms of median antibody titers, was 7,500, 12,500 and 32,500 for 10%, 20% and 30% wt/wt formulations, respectively (FIG. 3B). This initial result suggested that increasing AuNP quantity on IVLN surfaces improved antibody production. Presumably, this improvement was the result of reduced AuNP spacing (10% wt=~11.25 nm; 20% wt=8.05 nm; 30% wt=6.25 nm) to facilitate more efficient B-cell receptor crosslinking.

Subsequent to the evaluation of AuNP surface density, we questioned what the role of peptide conjugation density on IVLNs was for a given Au/Fe weight loading ratio. Peptide density has been positively connected to increased B-cell activation with potential for dose sparing by numerous previous reports. Notably, peptide density negatively correlated to reduction of antibody specificity. For the 30% wt ratio, low density peptide on IVLN surfaces yielded a median antigen-specific IgG antibody titer of 6,500, while high density peptide on IVLN surface yielded a median titer of 32,500 (FIG. 3B). This trend was also observed at the 20% wt ratio condition, which produced median titers of 1,300 and 12,500 for low density and high density, respectively. However, this trend did not translate to the 10% wt ratio condition. Presumably, this is due to a greater than 10 nm spacing between AuNPs on IVLN surfaces. Based on the above analysis, it was determined that higher peptide density and higher number of AuNPs per IVLN surface were generally preferred for antigen-specific antibody production due to the increasingly viral-like nature of the material. Significantly, peptide density was demonstrated to improve antibody titers without a loss of antigen-specificity. Based on these results, the 30% wt ratio plus high-density peptide condition was employed in all assays moving forward and referred to simply as IVLN or IVLN-HER2.

To effectively evaluate the significance of viral-like character for the application of antigen-specific antibody production, we next asked how the IVLN would perform as directly compared to a traditional nanoparticle system. For this comparison, we utilized a lipid-coated iron-oxide nanoparticle (Lipid-IONP) as a control (see FIG. 1). This nanoparticle has a 30-nm iron-oxide nanoparticle core and a functionalized DSPE-PEG(2000)-maleimide shell that facilitates facile peptide conjugation. Significantly, Lipid-IONPs have similar material properties in terms of hydrodynamic particle size (69±1 nm), PDI (0.20±0.01 nm), and maximum peptide number per particle (2323±394 peptides per IVLN). However, as a traditional nanoparticle system, Lipid-IONPs have smooth PEGylated surfaces with homogeneous peptide distribution. Taken together, we believe that the side-by-side comparison of IVLNs and Lipid-IONPs would offer valuable insights into the role of viral mimicry for in-vivo functionality.

Figure 3C:
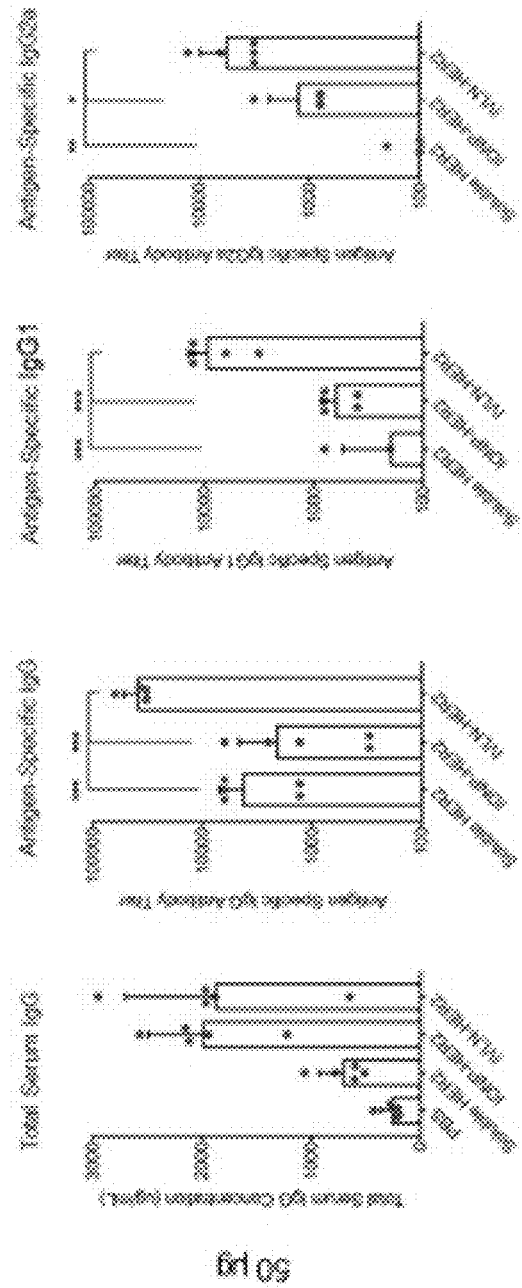

As before, BALB/c mice were immunized with 50 µg of HER2 peptide plus 10 µg of cGAMP as adjuvant at day 0 and boosted at day 14. At day 24, 10 days post-boost 1, serum was analyzed for total IgM, total IgG, antigen-specific IgG and the antigen-specific IgG isotypes, IgG1 and IgG2a (FIG. 3C). At this time point, no statistically significant difference in total IgM antibody production were observed ($p=0.09$), however a significant increase in total IgG was observed for both Lipid-IONP-HER2 and IVLN-HER2 as compared to PBS alone and soluble HER2 peptide treated mice. More specifically, an approximately 7-fold and 3-fold increase in total IgG was observed for both the Lipid-IONP-HER2 and IVLN-HER2 samples as compared to PBS alone ($p<0.001$; $p<0.001$) and soluble HER2 ($p<0.01$; $p<0.01$), respectively. No statistically significant difference between Lipid-IONP-HER2 and IVLN-HER2 was observed for total IgG ($p=0.98$). However, when antigen-specific IgG was evaluated a dramatic difference between IVLN-HER2 and Lipid-IONP-HER2 was observed. Namely, IVLN-HER2 was determined to have an 18.5-fold higher antigen-specific IgG titer (39,500 vs. 2,140; $p<0.001$) a 15-fold higher antigen-specific IgG1 titer (9,600 vs. 640; $p<0.001$) and a 4.5-fold higher antigen-specific IgG2a titer (5,760 vs. 1,280; $p<0.05$) as compared to Lipid-IONP-HER2. Moreover, IVLN-HER2 yielded an 9-fold higher antigen-specific IgG titer (39,500 vs. 4,300; $p<0.001$), a 48-fold higher antigen-specific IgG1 titer (9,600 vs. 200; $p<0.001$) and a 72-fold higher antigen-specific IgG2a titer (5,760 vs. 80; $p<0.01$) as directly compared to soluble HER2 peptide.

Viral-like characteristics are ideal material properties for the rational design and engineering of the delivery vehicles, immunostimulatory agents and cellular uptake vectors desperately needed for the advancement of nanotechnology in biotechnology and medical applications. Accordingly, here we report the development and evaluation of an alternative to viral-like particles with a more holistic approach to viral mimicry material design—inorganic virus-like nanoparticles (IVLN) and IVLN-peptides. In certain embodiments, the IVLNs are composed of a hybrid Au@Fe core-satellite type nanoparticle system, which utilizes a 16-nm polysiloxane containing diblock polymer coated iron-oxide nanoparticle core (IONP-polymer) with 2.5-nm gold nanoparticle satellites (AuNP). Based upon the formulation conditions, IVLNs can be produced with variable surface topography, antigen density and antigen spatial resolution. Moreover, the IVLN has optimal particle size, shape and surface charge for efficient lymph node delivery and retention. As such, these properties inform the viral-like character and functional potential of IVLNs.

Our results showed that viral-like character is truly significant for B-cell activation and antigen-specific antibody production. Specifically, by manipulating the spatial distribution of AuNPs on IVLN surface and the peptide density regional confined to those AuNPs, it was possible to increase the median antigen-specific IgG antibody titer from 6,300 to 32,500—a 5-fold increase. This result was further corroborated by direct comparison of IVLNs to Lipid-IONPs. Significantly, as compared to Lipid-IONP-HER2, IVLN-HER2 was determined to have 18.5-fold, 15-fold and 4.5-fold higher antigen-specific IgG, IgG1 and IgG2a titers, respectively (FIG. 3). With highly comparable hydrodynamic particle size, surface charge, core shape and peptide loading per unit nanoparticle, any quantifiable differences in antibody production by these two structures could be attributed to increasingly viral-like character. Mechanistically, this viral-like character led to enhanced antigen-specific antibody production as a result of greater delivery to and retention in the lymph nodes due to improved immune cell uptake, which promoted a significant increase in overall B-cell activation and germinal center formation.

Example 2

Virus-Like Nanoparticles for Antigen-Specific Antibody Production

This Examples describes the production and use of virus-like nanoparticles to produce antibodies. In order to achieve the viral-like structures, we engineered IVLNs, using a controllable and robust self-assembly process, to resemble spiky peplomers of virus, which have spiky antigen cluster topography, a certain distance between antigen clusters, and localized high antigen density on the spike.

In order to test IVLNs for viral functional mimicry, we evaluated the IVLNs to activate antigen-specific B cells and durable antigen-specific antibody response. We selected a well-known HER2 B cell epitope with overlap CD4 T cell epitope since the in vivo model for evaluation of durable antibody response is readily available by monitoring HER2 tumor growth without need of a biological safety level four lab. Three important viral like functions of IVLNs were evaluated: (1) antigen delivery efficiency and B cell zone uptake in the secondary lymph nodes; (2) antigen specific B cell activation by different density and spatial arrangements of antigen on the IVLN surface; and (3) follicular T helper cell activation in the Germinal center for B cell activation and durable antibody response. The durable function of antigen specific antibody was evaluated in vivo to inhibit HER2 cancer growth.

Materials and Methods

Materials

All reagents were used as obtained from commercial sources without further purification, except for γ-Methacryl oxypropyltrimethoxysilane (98%) that was purified by distillation under reduced pressure and 2,2-Azobis(isobutyronitrile) (98%) that was purified by recrystallization in ethanol. Iron oxide (III) (FeO(OH), hydrated, catalyst grade, 30-50 mesh), oleic acid (technical grade, 90%), ammonium iron (II) sulfate hexahydrate (ACS reagent, 99%), 1-octadecene (technical grade, 90%), anhydrous tetrahydrofuran (THF, 99.8%), carbon disulfide (99.9%), magnesium turnings (>99.5%), 2-chloro-2-phenylacetyl chloride (CPAC, 90%), poly(ethylene oxide) monomethyl ether (PEO), anhydrous dioxane (99.8%), dimethylformamide (DMF, 99.9%), dimethyl sulfoxide (DMSO, 99.9%), o-phenanthroline monohydrate (ACS reagent, 99%), hydroquinone (ACS reagent, 99%, sodium sulfide, chloroauric acid, nitric acid (ACS reagent, 70%), and hydrochloric acid (ACS reagent, 37%) were purchased from Sigma-Aldrich. Mouse uncoated IgG and IgM Total ELISA Kits, 1-Step Ultra TMB-ELISA substrate solution, HRP-conjugated goat anti-mouse IgG1 secondary antibody, HRP-conjugated goat anti-mouse IgG2a secondary antibody, Nunc Immobilizer Amino 96-well ELISA plates, BupH carbonate bicarbonate buffer packs (coating buffer), Pierce protein free PBS-tween blocking buffer, 20×PBS-tween wash buffer, Geneticin (G418) selective antibiotic, Invitrogen eBioscience fixable viability dye eFluor 780, and Molecular Probes streptavidin Alexa Fluor 647 conjugate were obtained from Thermo Fisher Scientific. HRP conjugated goat anti-mouse IgG secondary antibody, Zombie UV fixable viability kit, FITC anti-mouse CD19, PE/Dazzle 594 anti-mouse IgD, Alexa Fluor 647 anti-mouse/house GL7 antigen, Brilliant Violet 421 and PE/Dazzle 594 anti-mouse/human CD45R/B220, FITC anti-mouse CD95, Brilliant Violet 421 anti-mouse/human CD11b, FITC anti-mouse CD169 and PE goat anti-mouse IgG secondary antibody were purchased from BioLegend. HER2 peptides (CDDDPESFDGDPASNTAPLQPEQLQ (SEQ ID NO:1), Biotin-PESFDGDPASNTAPLQPEQLQ (SEQ ID NO:2), CDDDPESFDGDPASNTA-PLQPEQLQGGGK, SEQ ID NO:3) were custom synthesized by LifeTein. Iron-oxide nanoparticles (30 nm) stabilized by oleic acid in chloroform were purchased from Ocean Nanotech. DSPE-PEG (2000) and DSPE-PEG (2000)-maleimide were obtained from Avanti Polar Lipids. 2'3'-cGAMP was acquired from InvivoGen. Fluorescamine was purchased from MP Biomedicals. Sulfo-Cy5.5 NHS ester was acquired from Lumiprobe. Microvette 500 Z-Gel serum collection vials with clotting factor were obtained from Sarstedt. Matrigel Basement Membrane Matrix was purchased from Corning. Gold and iron ICP standards were purchased from Fluka Analytical.

Mice

All animal experiments were conducted according to the protocols approved by the University of Michigan Committee on Use and Care of Animals (UCUCA). BALB/c mice ages 5-7 weeks were purchased from Charles River Labs.

Cells

All cells were maintained at 37° C., 5% $CO_2$/95% air atmosphere and approximately 85% relative humidity. D2F2/E2 cells ((83)) were cultured in complete DMEM high glucose supplemented with 10% NCTC 109 media, 1% L-glutamine, 1% MEMs non-essential amino acids, 0.5% sodium pyruvate, 2.5% sodium bicarbonate, 1% pen/strep, 5% cosmic calf serum, 5% fetal bovine serum, 500 µg/mL Geneticin and 50 µM 2-mercaptoethanol. RAW264.7 macrophages were cultured in complete RPMI-1640 media supplemented with 10% fetal bovine serum, 1% L-glutamine, 1% MEMs non-essential amino acids, 1% sodium pyruvate and 1% pen/strep. Primary B-cells were cultured in RPMI-1640 media supplemented with 10% heat-inactivated fetal bovine serum.

Formulation and Characterization of Inorganic Virus-Like Nanoparticles (IVLN)

The IVLN was formulated generally as in Example 1. The final Au to Fe ratio of the formulated IVLN was quantified by inductively coupled plasma mass spectrometry (ICP-MS) using a Perkin-Elmer Nexion 2000 based on previously reported protocols modified from analysis by ICP-OES (78). IVLN formulations were imaged by s scanning transmission (electron microscopy (STEM) using a JEOL 2100F with a CEOS probe corrector. The true particle size of AuNPs, IONPs and IVLNs was quantified using ImageJ software. The volume-weighted hydrodynamic particle size, polydispersity index and zeta-potential of all formulations in milliQ water at 25° C. was evaluated with the Malvern Zetasizer Nano-ZS using dynamic light scattering and phase analysis light scattering, respectively.

Lipid-Coated Iron-Oxide Nanoparticle Formulations (IONP)

Lipid-coated iron-oxide nanoparticles were prepared as follows. DSPE-PEG (2000)-maleimide (10 mg) was added to 1 mg of 30-nm iron-oxide nanoparticles stabilized by oleic acid in chloroform as gently mixed. The resulting solution was subjected to solvent rotary evaporation to remove all chloroform and form a thin film. Simultaneously, this film and 100 mM PBS, pH 7.4 were heated to 75° C. in an oven. Upon reaching temperature, hot PBS was rapidly added to the film and mixed immediately and vigorously to facilitate thin film hydration. The resulting nanoparticle solution was stored at 4° C. to promote lipid self-assembly. Free phospholipid was removed by magnetic separation overnight at 4° C. using the EasySep magnetic separator device (StemCell).

IONP-HER2 and IVLN-HER2 Formulations

HER2 peptides were conjugated to both IONP and IVLN through thiol-mediated chemistries. Specifically, IONP-HER2 was formulated via maleimide chemistry and IVLN-HER2 was formulated via the gold-thiol linkage. HER2 peptide was added to IONP at 1.5× weight ratio excess in milliQ and incubated overnight at 4° C. HER2 peptide was added to IVLN-HER2 at 5× weight ratio excess in milliQ and incubated overnight at 4° C. Both materials were purified either by magnetic separation overnight at 4° C. using magnetic separation, or by centrifugal separation at 10,000×g for 30 minutes at 4° C. Peptide loading was determined using fluorescent quantification using a modified fluorescamine peptide quantification assay in the presence of nanoparticles (Ex/Em: 390/465 nm, Biotek Cytation 5)(86). Quantification was performed using a standard curve with increasing peptide concentration with standardized concentration of nanoparticles (IONP or IVLN) to account for quenching effects.

Immunizations and Serum Collection

At day 0, mice were immunized with the equivalent of 50 µg or 5 µg of HER2 peptide plus 10 µg of cGAMP regardless of formulation type. Subsequently, at day 14, mice were boosted twice at two-week intervals with 50% of the original dosage for both antigen and adjuvant (day 14 and 28). To evaluate serum antibody titers, blood was collected by submandibular puncture 10 days after each immunization (day 10, 24 and 38). Serum was separated from whole blood by centrifugal separation at 10,000×g for 5 minutes at 25° C. using the Microvette 500 Ser-Gel collection vessels with clotting activator.

Enzyme-Linked Immunosorbent Assay (ELISA)

Absolution quantification of total IgG and total IgM antibody analysis was performed using the mouse uncoated total IgG and total IgM ELISA kits based on manufacturer recommended protocols (Thermo Fisher). Antigen-specific IgG, IgG1 and IgG2a antibody titers were quantified based on previously established protocols for indirect ELISA with minor modifications (87). Specifically, HER2 peptides (200 µL, 100 µg/mL in 100 mM carbonate buffer, pH 9.4) were chemically conjugated to ELISA plates through the terminal amine group utilizing Nunc Immobilizer Amino immunoassay plates by overnight incubation with exposure to light at room temperature. Following overnight incubation, ELISA plates were washed three times with 100 mM PBS, pH 7.4 with 2% Tween-20. Subsequently, ELISA plates were blocked overnight at 4° C. with 300 µL of ELISA blocker (Pierce Protein-Free PBS Blocking Buffer). Following blocking, the ELISA plates were washed 3×. Serum samples containing primary antibodies were serially diluted ($10^1$-$10^8$ fold) using 100 mM PBS, pH 7.4 containing 10% ELISA blocker reagent and added to each well at 200 µL total for 2 hour incubation at room temperature. Following sample addition, the ELISA plates were washed 3×. 500-fold diluted anti-IgG-HRP, anti-IgG1-HRP, or anti-IgG2a-HRP was added at 100 µL to each well and incubated for 1 hour at room temperature. After 1 hour, the ELISA plates were washed 5×. Next, 100 µL of 1-Step Ultra TMB Substrate Solution was added to each well and allowed to incubate and develop color for 15-20 minutes at room temperature with gentle agitation. After 15-20 minutes, color development was stopped by the addition of 100 µL of 100 mM sulfuric acid. Colorimetric development was quantified by absorbance spectroscopy at 450 nm using the BioTek Cytation 5 plate reader. Antibody titers were determined by any absorbance signal at a given dilution factor that was greater than the PBS control absorbance signal plus three standard deviations(88).

Quantification of Nanoparticle Delivery to Lymph Nodes In-Vivo

Mice were injected subcutaneously in the left hock with either IONP or IVLN at a dose of 200 µg Fe per mouse. At the designated time intervals, mice were sacrificed and lymph nodes of interest were dissected for ex-vivo analysis. The extent of nanoparticle delivery to the lymph nodes was quantified using ICP-MS based on previously reported protocols (77).

Quantification of Peptide Delivery to Lymph Nodes In-Vivo

To facilitate quantification of peptide delivery to lymph nodes, lysine terminally modified HER2 peptides were chemically conjugated to sulfo-Cy5.5 NHS Ester. This conjugation was carried out at a 5-fold molar excess of sulfo-Cy5.5 NHS Ester to HER2 peptide. IONP-HER2-Cy5.5 and IVLN-HER2-Cy5.5 were subjected to Cy5.5 functionalization after initial peptide conjugation was completed in order to enable facile purification of excess fluorescent dye by magnetic separation. Subsequent to Cy5.5 functionalization, mice were injected as previously stated. After 3 hours, mice were sacrificed and lymph nodes of interest were dissected for ex-vivo analysis by IVIS imaging. IVIS imaging was utilized for semi-quantification of peptide delivery in terms of radiant efficiency.

In-Vivo Cell Uptake

IVLN-HER-Cy5.5 and IONP-HER2-Cy5.5 were injected subcutaneously in the left hock with either Lipid-IONP or IVLN at 200 µg total Fe per mouse. At 3 hours and 24 hours, mice were sacrificed and lymph nodes of interest were dissected for ex-vivo analysis by flow cytometry. Lymph nodes were dissociated by mechanical methods to prepare single cell suspensions. Single cell suspensions of lymph node cells were stained for analysis by flow cytometry using the MoFlo Astrios flow cytometer. Viable cells (Zombie UV) were identified as either B-cells ($B220^+$) or subcapsular sinus macrophages ($CD169^{high}CD11b^+$) and evaluated for positive nanoparticle interactions (Cy5.5). Flow cytometry data was analyzed by FCS express.

In-Vitro Cell Uptake

IVLN-HER2 and IONP-HER2 cellular uptakes were evaluated in RAW264.7 macrophages, dendritic cells (DC 2.4), and primary B-cells isolated from murine spleens using an EasySep Mouse B-cell isolation kit. Nanoparticle samples were incubated at 50 µg/mL Fe with cells for 18 hours in blank RPMI media at 37° C., 5% $CO_2$/95% air atmosphere and approximately 85% relative humidity. After 18 hours, cells were lifted by cell scraping and washed thrice with PBS. Following the wash steps, resulting cell pellets were re-suspended in 1 mL of PBS, cell counted and then digested in 1 mL aqua regia (1:3 molar ratio nitric acid: hydrochloric acid) for analysis by ICP-MS.

Mass Cytometry (CyTOF) to Analyze all Immune Cells

Fixed and frozen cell suspensions were thawed on ice. Samples were stained and prepared for CyTOF analysis as previously described (89, 90), using an optimized cocktail of 40 metal-conjugated antibodies designed to identify major and minor immune cell subsets in lymph nodes. Following acquisition on a CyTOF II (Fluidigm, San Francisco, CA), samples were normalized to internal bead standards. Cell subsets were identified by gating using FlowJo software. Global analysis using SPADE were performed for unsupervised clustering analysis based on the expression of marked genes in different subset of immune cells.

Antigen-Specific B-Cell and Germinal Center Flow Cytometry

Mice were immunized as previously introduced. At day 10, mice were sacrificed and lymph nodes were dissected for ex-vivo analysis by flow cytometry. Antigen-specific B-cell analysis was accomplished using tetramer staining based on previously established protocols with minor modifications (63). HER2/neu peptide tetramers were prepared by mixture of biotin-labeled HER2 peptide with Alexa Fluor 647 labeled streptavidin at a 4:1 molar ratio at room temperature for 1 hour without further purification. Antigen-specific B-cell population was identified using CD19, and the HER2-peptide tetramer using flow cytometry. Germinal center B-cell populations were identified using the following markers B220, IgD, GL7 and CD95 ($B220^+IgD^{low}GL7^+CD95^+$).

Tumor Studies

Forty-nine days after the primary immunization, mice were inoculated with $2.5 \times 10^5$ D2F2/E2 cells subcutaneously in the right flank. D2F2/E2 cells were prepared at $2.5 \times 10^6$ cells/mL in 100 µL and mixed at equal volume with Matrigel matrix. Tumor size was quantified by caliper measurements every 7 days. Tumor volumes were calculated by volume= $(width)^2 \times length/2$. End points were determined by using the End-Stage Illness Scoring System; mice receiving an End-Stage Illness Score greater than 6 were euthanized by $CO_2$ asphyxiation.

Statistics

Data are expressed as mean±standard deviation (SD), unless otherwise specified. Comparisons between two groups were made using the unpaired Student's t-test. Means of multiple groups were compared with the one-way analysis of variance (ANOVA), followed by post hoc Tukey's pairwise comparisons. All probability values are two-sided, and values of $p<0.05$ were considered statistically significant. Statistical analyses were carried out using the GraphPad Prism 7 software package.

Results

Figure 6:
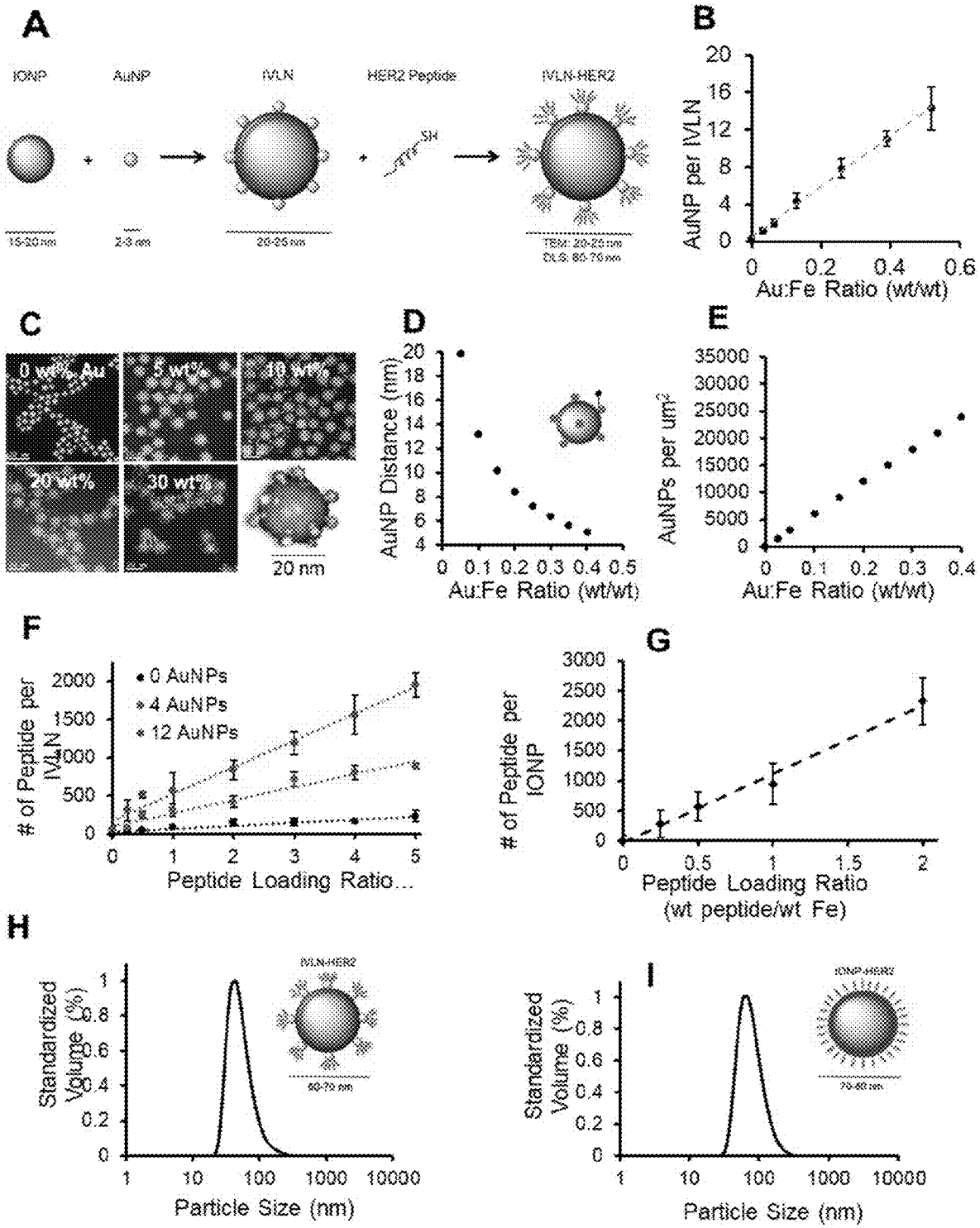
FIG. 6, panels A-I, shows, in certain embodiments, inorganic viral-like nanosatellites (IVLNs) have three important features that resemble the spiky antigen peplomer of virus: Spiky antigen cluster topography, optimal distance (5 nm) between antigen clusters, and localized high antigen density on the spike. (A) Schematic representation of the step-wise production of peptide functionalized inorganic virus-like nanoparticles (IVLN-HER2) by the (1) self-assembly of AuNPs to polymer-coated IONP surfaces via the gold-siloxane interaction (IVLN) followed by the (2) conjugation of terminal cysteine-modified HER2 peptide to IVLN via gold-thiol bond. (B) Gold nanoparticle (AuNP) loading per iron-oxide nanoparticles core (IONP) measured by ICP-MS. Data represent mean±SD, n≥6; curve is fit using linear regression model, $R^2$=0.998, p<0.001. (C) STEM HAADF images of IVLN at increasing AuNP/IONP ratios from 0-30%; scale-bar: 0% wt condition (50 nm); scale-bar: 5-30% wt conditions (20 nm). (C-insert) STEM image of single IVLN. (D) Distances between AuNPs on IVLN surfaces as calculated by mathematical modeling (FIG. S2). (E) AuNP density (per unit area) on IVLN surfaces as compared to the known antigen density on viral capsids as calculated by mathematical modeling. (F) Peptide loading on IVLNs with variable AuNP (0 AuNPs—black; 4 AuNPs—blue; 12 AuNPs—red) as determined by a modified fluorescamine fluorescent detection assay; data represent mean±SD, n=3; curve is fit using linear regression model, (0 AuNPs: $R^2$=0.904,p<0.01; 4 AuNPs: $R^2$=0.962, p<0.01; 12 AuNPs: $R^2$=0.977,p<0.001). (G) Peptide loading on lipid-coated iron-oxide nanoparticles (IONP-HER2) data represent mean±SD, n=3; curve is fit using linear regression model ($R^2$=0.989,p<0.001). (H) Diagram and volume-weighted particle size of IVLN-HER2 by dynamic light scattering (DLS). (I) Diagram and volume weighted particle size of lipid-coated iron-oxide nanoparticle-HER2 (IONP-HER2).
Figure 7:
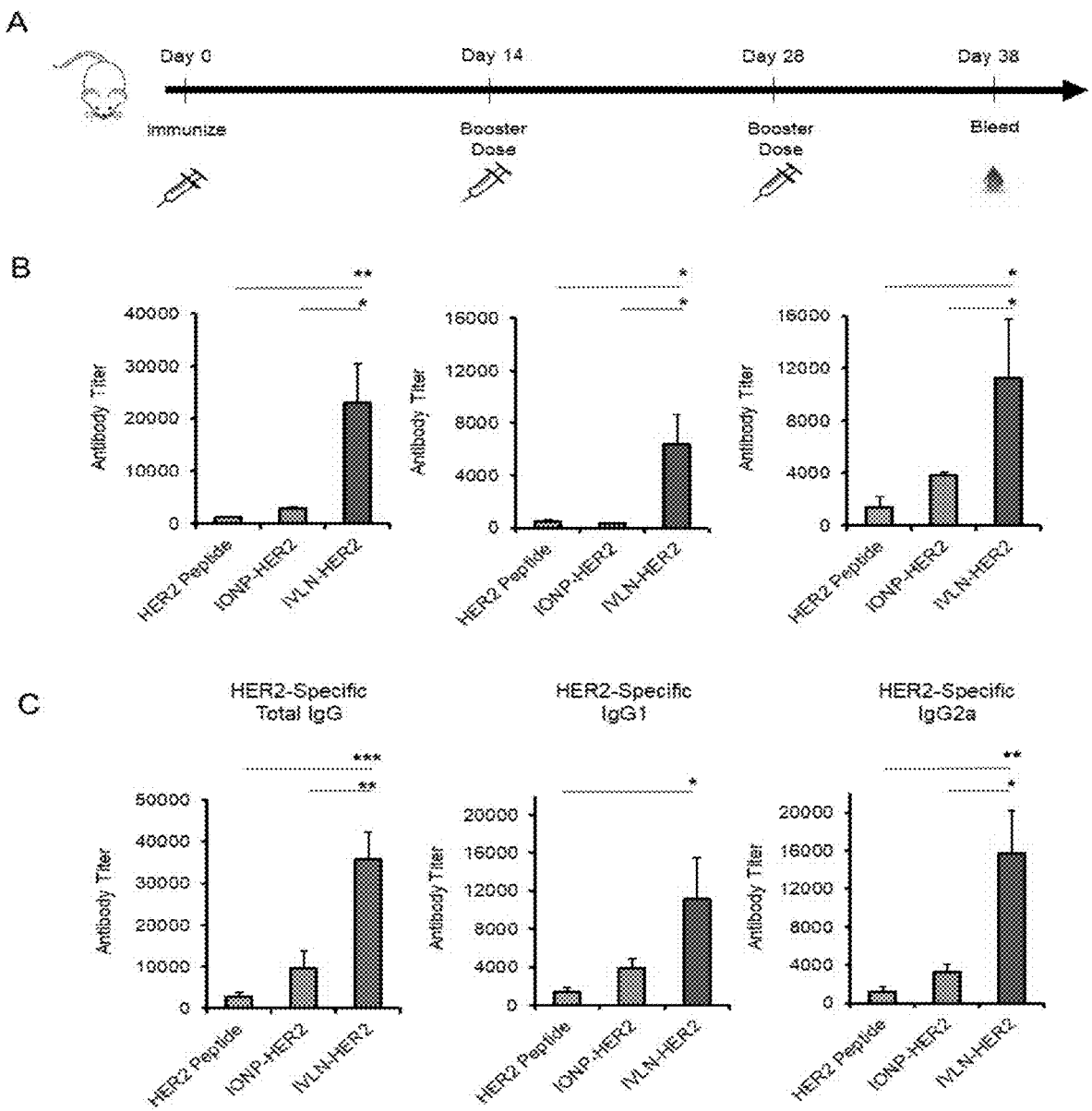

Engineer Inorganic Viral-Like Nanoparticles (IVLNs) to Mimic Viral-Like Spiky Structure We have developed a controllable and robust process to manufacture IVLNs using a self-assembly process. To achieve viral-like spiky topography, the AuNPs (2 nm) were attached onto the surface of IONP (15 nm) to produce IVLN (FIG. 6A). The attachment of AuNP and IONP was achieved by self-assembly from the interaction between reactive AuNP surfaces and free siloxane moieties present in the polymer used to coat the IONP. This process is controlled and robust for large-scale manufacture.

The IONP was synthesized by thermal decomposition to produce a 15-nm spherical core stabilized by oleic acid in chloroform. To achieve aqueous stabilization, the IONP was coated with a poly(siloxane) and poly(ethylene glycol) containing di-block co-polymer based on procedures previously reported (51). The ultra-small gold nanoparticles or satellites (AuNPs) with ~2-3 nm sizes were prepared using a modified precipitation method by reduction of chloroauric acid in aged sodium sulfide (53). The AuNP solution was added to an IONP solution at defined weight ratios and incubated overnight at 4° C. to allow for self-assembly of IVLNs. To control the number of viral-like spiky structures on IVLN from 4-14 (FIG. 6B, 6C), the ratios of AuNPs to IONPs were adjusted to 10%, 20% and 30% AuNP/IONP, as measured by ICP-MS (54, 55), yielded IVLNs with 4±2, 9±3 and 13±5 AuNPs per IVLN (FIG. 6B). The viral-like structure of IVLN was confirmed by scanning transmission electron microscopy (STEM) (FIG. 6C). The high-angle annular dark-field (HAADF) image of single IVLN (with 14 AuNPs) showed close resemblances of viral-like structure (FIG. 6C).

IVLNs Conjugated with Non-Capsid Antigen Peptides Resemble Spiky Peplomer Structure of a Virus with Three Viral-Like Features In order to mimic antigen structure similar to peplomers of virus, three features are employed: spiky antigen cluster topography, optimal distance (5 nm) between antigen clusters, and localized high antigen density on the spike.

The spiky antigen cluster topography was achieved by conjugating antigen peptides only to the spike AuNPs of IVLNs, but not on the polymer of IONP core. We used a non-viral-capsid and well-known HER2 B cell epitope with an overlapping CD4 T-cell epitope (CDDD-PESFDGD-PASNTAPLQPEQLQGGK (56-58). We selected HER2 B cell epitopes as a proof of concept study to study viral like structure and functional mimicry of IVLNs since the in vivo model is readily available to test antibody function by monitoring tumor growth without need a biosafety level 4 lab. The conjugation of HER2 peptides (with cysteine at the N-terminus) was achieved only to the spiky AuNP through S—Au reaction on IVLN, but not on the adjacent polymer coating on INOP (FIG. 6F, 1H). Polymer-coated IONP alone without AuNPs were used as control. High levels of peptide conjugation were observed for IVLNs with AuNPs, but not on the IONP core alone (FIG. 6F, black symbols). Additionally, a positive correlation between peptide loading and AuNP number were observed (R=0.95). These results suggest that, although there is a low-level non-specific association of HER2 peptides to INOP core (~12%), peptide conjugation is AuNP dependent, which achieved antigen spiky cluster topography on IVLN; these viral mimicry feature cannot be achieved by traditional nanoparticles that only have uniform Antigen distribution on their surface (FIG. 6I).

To control the distance between two spiky antigen clusters at 5-10 nm, which is an ideal distance for B cell receptor (BCR) cross-linking and activation (41, 59), we adjusted the number of AuNP at 14 on the IVLN surfaces using different ratios of AuNP/IONP, which produced distance between 5.1-6.3 nm (FIG. 6D).

To control the highly localized antigen density on the spike, we conjugated different amount of HER2 peptides on IVLN with 0%, 10% and 30% AuNP/IONP ratios, which correspond to 0, 4, 13 AuNP on the IVLN surface, respectively (FIG. 6F). The peptide loadings were 232±73, 888±42 and 1954±157 peptides per IVLN (227±5 peptides per AuNP, FIG. 6F). Therefore, IVLN achieved an density of 20,000-25,000 antigen clusters per $\mu^2$, which is comparable to the antigen density reported for VLPs(9) (e.g. Hepatitis B Virus, 20,000 antigens) (FIG. 6E).

To mimic the optimal viral size and surface charge (32, 34), IVLNs have a 50-60 nm particle size, 0.2 PDI and a −16 mV zeta-potential (FIG. 6H). In addition, under in-vivo relevant serum conditions, IVLN-HER2 were shown to be stable between 12 and 24 hours.

To effectively evaluate these three features of viral-mimicry structures of IVLNs, a traditional lipid-coated IONP (IONP-HER2) with similar size, charge, peptide density (2323±394 peptides per IONP, but a uniform antigen distribution) on the surface was generated as a control (FIG. 6G, 6I). IONP-HER2 has a 30-nm IONP core and a functionalized DSPE-PEG (2000)-maleimide shell that facilitates facile peptide conjugation. IONP-HER2 has similar material properties in terms of volume-weighted hydrodynamic particle size (68±5 nm), PDI (0.22±0.02) and maximal number per particle (2323±394 peptides per IONP) (FIG. 7G). Therefore, the side-by-side comparison of IVLN-HER2 and IONP-HER2 would offer valuable insights into the role of viral mimicry function.

IVLN-HER2 Enhanced 7 to 18-Fold HER2-Specific Antibody Production Vs. INOP-HER2

Viral mimicking nanoparticles have been utilized in a wide-range of in-vitro and in-vivo applications, but the most significant application of viral-like structure and function is to activate B-cells for antigen-specific antibody production (2, 6, 13, 57, 60-62). Therefore, we first tested if the IVLN-HER2 induced antigen-specific IgG production in-vivo against a non-capsid oncogenic human HER2-specific peptide (HER2).

The optimized IVLNs (~14 spiky antigen clusters, distance between two antigen clusters 5-6 nm, 2000 peptides/IVLN, 150 peptides/AuNP) were used to immunized BALB/c mice to produce HER2-specific antibody, in comparison with a traditional lipid-coated IONP-HER2 with similar HER2 peptide density (~2000 peptides/INOP, uniform antigen distribution). IVLN-HER2 and IONP-HER2 have similar size under TEM (30 nm) and DLS (65 nm). The same dose of HER2 peptides in all groups were used for immunization of BALB/c mice (5 ug, or 50 ug peptide, 10 μg cGAMP as adjuvant) at day 0 and boosted twice at 14-day intervals (FIG. 7A). Two doses (5 ug and 50 ug) of HER2 were used for immunization. Complete serum analysis was performed after two booster immunizations (day 38) because this time point was determined to be most responsive and therefore most relevant. Antibody responses were analyzed using ELISA after two booster immunizations (day 38) for total IgM, total IgG, HER2-specific IgG and the HER2-specific IgG isotypes (IgG1 and IgG2a).

At a low dose, IVLN-HER2 (5 ug) generated an 8-fold higher HER2-specific IgG titer, an 18-fold higher HER2-specific IgG1 titer, and a 13-fold higher HER2-specific IgG2a titer as compared to IONP-HER2. Moreover, IVLN-HER2 yielded a 14-fold higher Ag-specific IgG titer, a 7-fold higher Ag-specific IgG1 titer, and a 14-fold higher Ag-specific IgG2a titer as compared to soluble HER2 peptide (FIG. 7B).

Similarly, at a high dose (50 ug), IVLN-HER2 (50 ug) enhanced a 12-fold higher antigen-specific IgG titer, an 8-fold higher antigen-specific IgG1 titer, and a 14-fold higher antigen-specific IgG2a titer as compared to soluble HER2 peptide. In comparison with INOP-HER2, IVLN-HER2 (50 ug) enhanced 4 to 5-fold higher antigen-specific IgG titer, a 3-fold higher antigen-specific IgG1 titer, and a 5-fold higher antigen-specific IgG2a titer (FIG. 7C). No statistically significant difference in total IgM and total IgG antibody production was observed between any treatment groups. Overall, these data indicate that the viral-like properties of IVLNs are more efficient for antigen-specific antibody production.

The Spiky Antigen Cluster Numbers, Distance Between Two Antigen Clusters, and Localized Antigen Density on IVLNs Affect their Ability to Produce Antigen-Specific Antibody Viral-like features are important for B-cell activation through multivalent B-cell receptor crosslinking (9, 40, 41), which includes different numbers of spiky antigen clusters, different distances between clusters, and different localized antigen density (2, 6, 13, 57, 60-62). Therefore, we tested if different IVLN-HER2 viral-mimic features influence anti-HER2 antibody production in BALB/c mice. We immunized mice at day 0 and boosted once at day 14 using IVLN-HER2 with different spiky cluster numbers and distance but using the same amount of HER2 peptides (50 μg HER2 peptide, 10 μg cGAMP as adjuvant) (FIG. 8A).

We first evaluated the effect of the numbers of spiky antigen clusters and distance between antigen clusters on HER2-specific IgG antibody production using two different AuNP/IONP ratios: 10% and 30%, which corresponds with AuNP numbers on IONP ratios from 4, 14, and distances between AuNPs is ~15 and ~5 nm. The IVLNs (with 14 antigen cluster and optimal distances between clusters is 5 nm) produced 6-fold higher HER2-specific IgG tilters (64, 500) compared to IVLN (with 4 antigen clusters, 15 nm distance between clusters) that generated HER2-specific IgG titer at 10,540 (FIG. 8B) although same dose of HER2 antigen was used in immunization.

Subsequently, we evaluated the effect of localized antigen density on IVLN on HER2-specific antibody production. IVLNs (14 antigen clusters with distance between clusters is ~5 nm, high density 150 peptides/cluster) generated 4-fold higher titer of antigen-specific antibody than IVLNs (with 4 antigen clusters with distance between clusters is 15 nm, low antigen density 30 peptides/cluster) although same HER2 antigen dose was used in immunization (FIG. 8B). The data suggest that the number of antigen clusters (14 clusters in this Example), distance between antigen clusters (5-6 nm in this Example), and localized antigen density (2000 peptides/ IVLN, ~150 peptides/AuNP in this Example) generated high HER2-specific antibody.

IVLN-HER2 Improved Lymph Node Delivery Efficiency and B Cell Zone Uptake in Comparison with IONP-HER2

Efficient antigen delivery to lymph node is pre-requisite for effective B cell activation and antibody responses. We first evaluated IVLN-HER2 delivery efficiency and retention in the lymph nodes (69, 70). Second, within the lymph node, we determined if IVLN-HER2 can be specifically targeted to B-cell zones since the lymph nodes are primary sites for B-cell activation and the formation of germinal centers that are ultimately responsible for initiating antigen-specific IgG antibody production (71-73). Third, we also tested if IVLNs had viral-like cellular distribution patterns within lymph nodes. As sites with dense populations of antigen-presenting cells and lymphocytes, the lymph nodes are known to be critically important in viral sequestration and directed immune activation (74, 75). This functionality is the result of unique physiological features that have been developed for viral recognition and viral-specific immune activation. For example, subcapsular sinus macrophages are a highly specialized phenotype of macrophage that is responsible for viral uptake and direct presentation to B-cells to promote directed viral clearance via antigen-specific antibody production (75, 76).

The delivery efficiency and retention of IVLN-HER2 in the lymph nodes in comparison with IONP-HRR2 was evaluated using two different methods (69, 70): ICP-MS quantification of Fe in excised lymph node (77, 78) and IVIS imaging of fluorescent labeled IVLN-HER2 peptide (79). The $t_{max}$ of both IVLN-HER2 and IONP-HER2 was 3 hours post-administration that suggests rapid direct trafficking to the lymph nodes. Over 48 hours, IVLN-HER2 has a 3.5-fold higher in overall exposure vs. IONP-HER2 based on area under the curve (AUC) (FIG. 9A). In addition, fluorescently labeled peptides were also used to monitor the lymph node delivery for IVLN-HER2, IONP-HER2 and soluble HER2 peptides at 3 hours using IVIS imaging of excised popliteal and inguinal lymph nodes (FIG. 9B). IVIS imaging revealed that IVLN-HER2 led to a 4.3-fold improvement in lymph node delivery as compared to both the IONP-HER2 and soluble HER2 peptide, where IONP-HER2 and HER2 have no statistically significant difference in delivery.

Subsequently, we tested if IVLN-HER2 had viral-like distributions within the lymph node, especially in subcapsular sinus macrophage and B-cell populations, as compared to IONP-HER2 (72, 73, 76). Fluorescently labeled IVLN-HER2 were injected by subcutaneous hock immunization and flow cytometry was applied 3 hours post-administration to identify IVLN-HER2 or IONP-HER2 positive cells of different phenotypes. Subcapsular sinus macrophages where identified as $CD11b^+CD169^{high}$ double-positive and B-cells were identified as $B220^+$ (76, 80). IVLN-HER2 improved subcapsular sinus macrophage uptake by 1.7-fold and B-cell uptake by 3.4-fold (FIG. 9C) in comparison with INOP-HER2. The intracellular uptake of IVLN-HER2 and IONP-HER2 was confirmed in-vitro in RAW 264.7 macrophages and primary B-cells isolated from murine spleens. Compared to the IONP-HER2 control group, IVLN-HER2 improved cellular uptake by 3-fold in macrophages and 2-fold in B-cells (FIG. 9D). Taken together, these data suggest that viral structural mimicry of IVLNs improved lymph node delivery efficiency and preferred B cell zone distribution in the lymph node.

IVLN-HER2 Induced Antigen-Specific Antibody with Durable Function

We used a well-known B cell epitope of HER2 antigen so that we can easily test the function of the induced antibody in an established model by monitoring the tumor growth after IVLN-HER2 immunization in vivo. The HER2 peptide on IVLNs is a B cell epitope to produce pertuzumab (Perjeta®)(56), which is currently used to treat HER2+ breast cancer in humans (81, 82). Therefore, we employed IVLN-HER2 as a vaccine for its in-vivo prophylactic efficacy to prevent tumor growth of HER2 breast cancer xenograft model (D2F2/E2 murine breast cancer with high human HER2 expression) (83). The prophylactic tumor inhibition was initiated by subcutaneous flank inoculation with $2.5 \times 10^5$ cells per mouse at day 49 following a primary immunization plus three additional booster administrations at 14-day intervals (FIG. 10A). IVLN-HER2 immunization significantly inhibited tumor growth over 6-weeks at a dose of 50 µg ($125 \pm 239$ mm$^2$ vs. $1843 \pm 661$ mm$^2$, p<0.001) (FIG. 10B) and 5 µg ($583 \pm 392$ mm$^2$ vs. $1843 \pm 661$ mm$^2$, p<0.001) (FIG. 10C), which was superior than INOP-HER2 and HER2 peptide only group. In addition, the prophylactic anti-cancer efficacy appears to be directly correlated not only to the specificity of these endogenous antibodies to the D2F2/E2 cell line, but also to the titer of antigen-specific antibody. These data suggest that the antigen specific antibody by IVLN-HER2 has durable function in vivo.

IVLN-HER2 Induced Antigen-Specific Antibody with Durable Function

We used a well-known B cell epitope of HER2 antigen so that we can easily test the function of the induced antibody in an established model by monitoring the tumor growth after IVLN-HER2 immunization in vivo. The HER2 peptide on IVLNs is a B cell epitope to produce pertuzumab (Perjeta®)(56), which is currently used to treat HER2+ breast cancer in human(81, 82). Therefore, we employed IVLN-HER2 as a vaccine for its in-vivo prophylactic efficacy to prevent tumor growth of HER2 breast cancer xenograft model (D2F2/E2 murine breast cancer with high human HER2 expression) (83). The prophylactic tumor inhibition was initiated by subcutaneous flank inoculation with $2.5 \times 10^5$ cells per mouse at day 49 following a primary immunization plus three additional booster administrations at 14-day intervals (FIG. 110A). IVLN-HER2 immunization significantly inhibited tumor growth over 6-weeks at a dose of 50 µg ($125 \pm 239$ mm$^2$ vs. $1843 \pm 661$ mm$^2$, p<0.001) (FIG. 110B) and 5 µg ($583 \pm 392$ mm$^2$ vs. $1843 \pm 661$ mm$^2$, p<0.001) (FIG. 10C), which was superior than INOP-HER2 and HER2 peptide only group. In addition, the prophylactic anti-cancer efficacy appears to be directly correlated not only to the specificity of these endogenous antibodies to the D2F2/E2 cell line, but also to the titer of antigen-specific antibody. These data suggest that the antigen specific antibody by IVLN-HER2 has durable function in vivo.

B cell immunity against viral capsid protein antigens on the virus surface is highly desired to prevent infections. In such case, virus like structure of the capsid antigens on the inactivated/live attenuated virus and virus like particles (VLPs) using virus capsid proteins is highly effective to active B cell immunity against viral infections (1-4). However, B cell immunity against non-capsid protein antigens is also desired in three other scenarios to against bacteria toxin of deadly bacteria infection, oncogenic proteins of cancers, and peptide antigens for antibody production (20, 21). However, it is very difficult to make virus like particles using these non-capsid antigens and thus activate B cell immunity. B cell vaccine against bacterial toxin is highly desired for prevention of deadly bacteria infection such as *C. Anthracis* (Anthrax) and *C. Botulinum* (20, 21). These bacterial toxin B cell vaccines usually use toxoid as antigens to boost neutralizing antibody (20, 21). The successful bacterial toxin vaccines are currently used against Tetanus and Diphtheria. However, the safety and efficacy for bacterial toxoid B cell vaccines of *C. Anthracis* (Anthrax) and *C. Botulinum* are two major concerns (20, 21). Due to highly toxic nature of these two toxins, it is preferably to use peptides antigens of these toxoids as vaccines (22). However, the peptide antigens are very inefficient to boost B cell immunity using nanoparticle delivery system without a virus structure mimicry. In addition, B cell immunity against oncogenic antigen may have potential benefit in prevention/treatment of cancers. For instance, several HER2 B cells vaccines are currently in clinical trials although there is still debate for the benefits/risks of B cell activation in cancers (23, 24). Furthermore, efficient antibody production against various peptide antigens is highly desired in disease detection/treatment (25). However, the efficiency of these peptide antigens to generate antibody is low and they can only generate low titer of antibody in a short term.

The current strategy to enhance B cell immunity against non-capsid antigens is to use nanodelivery system to mimic viral like structures. However, most nanodelivery systems do not have true virus like structures that are inefficient to activate B cell immunity. Although the nanodelivery system without viral like structure is superior than soluble peptides for B cell immunity, they only able to activate low levels of antigen-specific B cells (less than 1-3%) and have short lived antibody responses (35-38). In contrast, the inorganic virus like nanoparticles (IVLNs) herein with HER2 peptides generated more than 17% antigen specific B cells in a follicular T helper cell dependent manner. These features induced durable antibody response to inhibit HER2 tumor growth in vivo. We selected HER2 B cell epitopes to study viral like structure and functional mimicry of IVLNs since the in vivo model is readily available to test antibody function by monitoring tumor growth without need a biosafety level 4 lab. However, the same principle can be applied to activate B cell immunity for other applications, such as antibody production against peptides, or B cell immunity against bacterial toxins of *C. Anthracis* (Anthrax) and *C. Botulinum*.

Example 3

Virus-Spike-Mimicry B Cell Nanovaccine, with LIGHT Peptide, Combined with αPD1 Achieve Remission in HER2+ Breast Cancer T cell cancer vaccines only achieve short-term efficacy while B cell cancer vaccines are controversial for cancer treatment. In this Example, we have engineered a virus spike mimicry B cell nanovaccine (VSM NanoVax) using HER2 B and CD4 T cell epitope and LIGHT peptide (FNFSF14), which resembles spiky antigen cluster topography to promote follicular T cell (Tfh)-dependent B cell activation in the lymph nodes and tertiary lymphoid structure (TLS) in tumor, achieved cancer remission in HER2+ breast cancer when combined with αPD1. VSM NanoVax was more efficient for lymph node homing, unique B cell zone localization, and crosslink with BCR in the lymph nodes. VSM NanoVax significantly increased antigen-specific B, Tfh, and GC cells in the lymph nodes. VSM NanoVax promoted TLS by remodeling tumor immune microenvironments through increasing GC, CD80+/IgM+ B, Tfh, and CD4+ EM cells. Such virus spike mimicry B cell nanovaccines could be used to achieve cancer remission in HER2+ breast cancer.

In this Example, we engineered a virus-spike-mimicry B cell nanovaccine (VSM NanoVax) using HER2 B cell and CD4+ T cell epitopes and LIGHT, which resembles the viral spiky antigen cluster topography to activate Tfh-dependent B cell activation in the lymph nodes and promote TLS formation by LIGHT in the tumor site. VSM NanoVax combined with anti-PD-1 antibody achieved cancer remission in HER2+ breast cancer (>180 days). HER2 antigen with B cell and CD4 epitope were used in VSM NanoVax, which is different from previously reported HER2 T cell anticancer vaccines using HER2 CD8 epitope. VSM NanoVax exhibited significantly better anticancer efficacy than Her-2 antibody and Her-2 T cell vaccine. VSM NanoVax (~30 nm) displayed HER2 B cell epitopes on the spike structure of nanoparticle, which mimics the "spiky glycoprotein peplomer" on the surface with spiky antigen cluster topography, optimal distance between clusters (5-10 nm), and localized high antigen density (>220 antigens/cluster, 20,000 antigens/um2). VSM NanoVax were efficiently drained to secondary lymphoid organs, primarily localized in the B cell zone, and efficiently cross linked with B cell receptor (BCR) for B cell activation. The CD4 epitopes on the VSM NanoVax, together with unique localization in the B cell zone and extensive BCR crosslink, stimulated follicular T helper cells, significantly increased antigen-specific B cell activation, and enhanced germinal center formation in the lymph nodes. Furthermore, VSM NanoVax (with LIGHT in the nanoformulation) promoted TLS formation, which is co-localized with VSM NanoVax in the tumor sites. The VSM NanoVax combined with anti-PD-1 antibody significantly remodeled immune microenvironments by increasing GC, CD80+/IgM+B cells, Tfh cells, and CD4+EM cells at tumor sites.

Materials and Methods

Materials

All reagents were used as obtained from commercial sources without further purification, except for γ-Methacryl oxypropyltrimethoxysilane (98%) that was purified by distillation under reduced pressure and 2,2-Azobis(isobutyronitrile) (98%) that was purified by recrystallization in ethanol. Iron oxide (III) (FeO(OH), hydrated, catalyst grade, 30-50 mesh), oleic acid (technical grade, 90%), ammonium iron (II) sulfate hexahydrate (ACS reagent, 99%), 1-octadecene (technical grade, 90%), anhydrous tetrahydrofuran (THF, 99.8%), carbon disulfide (99.9%), magnesium turnings (>99.5%), 2-chloro-2-phenylacetyl chloride (CPAC, 90%), poly(ethylene oxide) monomethyl ether (PEO), anhydrous dioxane (99.8%), dimethylformamide (DMF, 99.9%), dimethyl sulfoxide (DMSO, 99.9%), o-phenanthroline monohydrate (ACS reagent, 99%), hydroquinone (ACS reagent, 99%, sodium sulfide, chloroauric acid, nitric acid (ACS reagent, 70%), and hydrochloric acid (ACS reagent, 37%) were purchased from Sigma-Aldrich. Dulbecco's phosphate-buffered saline (DPBS) and Hank's buffered salt solution (HBSS) were obtained from Fisher Scientific. Mouse uncoated IgG and IgM Total ELISA Kits, 1-Step Ultra TMB-ELISA substrate solution, HRP-conjugated goat anti-mouse IgG1 secondary antibody, HRP-conjugated goat anti-mouse IgG2a secondary antibody, Nunc Immobilizer Amino 96-well ELISA plates, BupH carbonate bicarbonate buffer packs (coating buffer), Pierce protein free PBS-tween blocking buffer, 20×PBS-tween wash buffer, Geneticin (G418) selective antibiotic, Invitrogen eBioscience fixable viability dye eFluor 780, and Molecular Probes streptavidin Alexa Fluor 647 conjugate were obtained from Thermo Fisher Scientific. EasySep™ Mouse B Cell Isolation Kit was purchased from StemCell Technologies. Fluo-4 AM was purchased from Thermo Fisher Scientific. Alexa Fluor® 488-AffiniPure Fab Fragment Goat Anti-Mouse IgM, μ Chain Specific was purchased from Jackson ImmunoResearch Laboratory Inc. Alexa Fluor™ Plus 405 Phalloidin was purchased from Thermo Scientific. Anti-mouse PD-1 antibody (CD279) was purchased from Bio X Cell. Mouse Granulocyte-macrophage colony-stimulating factor (GM-CSF) was obtained from SHENANDOAH Biotechnology Inc.

Murinized Pertuzumab and Trastuzumab were purchased from GenScript. LIGHT (TNFSF14) was purchased from Sino Biological. HRP conjugated goat anti-mouse IgG secondary antibody, Zombie UV fixable viability kit, FITC anti-mouse CD19, PE/Dazzle 594 anti-mouse IgD, Alexa Fluor® 647 anti-mouse/house GL7 antigen, Brilliant Violet 421 and PE/Dazzle 594 anti-mouse/human CD45R/B220, FITC anti-mouse CD95, Brilliant Violet 421 anti-mouse/human CD11b, Alexa Fluor® 647 anti-mouse CD21/CD35 (CR2/CR1), Alexa Fluor® 594 anti-mouse CD169, FITC anti-mouse CD169 and PE goat anti-mouse IgG secondary antibody, FITC anti-mouse CD19, Brilliant Violet 605 anti-mouse CD19, Alexa Fluor® 594 anti-mouse CD19, APC/Cyanine7 anti-mouse CD86, FITC anti-mouse CD3 were purchased from BioLegend. HER2 peptides (CDDDPESFDGDPASNTAPLQPEQLQ (SEQ ID NO: 1), Biotin-PESFDGDPASNTAPLQPEQLQ (SEQ ID NO: 2), CDDDPESFDGDPASNTAPLQPEQLQGGGK (SEQ ID NO: 3), CDDDPESFDGDPASNTAPLQPEQLQ-GGG-{Lys(Np)} (SEQ ID NO: 14),DDDPESFDGDPASNTA-PLQPEQLQ-{Lys{N3}-DBCO-Cy3}-GGG-{Lys(Np)} (SEQ ID NO: 15), CDDDPESFDGDPASNTAPLQPEQLQ-EDFITC) (SEQ ID NO: 16), CDDDKIFGSLAFL (SEQ ID NO: 17) and E75 (HER2369-377 KIFGSLAFL(SEQ ID NO: 18)) were custom synthesized by LifeTein. Iron-oxide nanoparticles (30 nm) stabilized by oleic acid in chloroform were purchased from Ocean Nanotech. DSPE-PEG (2000) and DSPE-PEG (2000)-maleimide were obtained from Avanti Polar Lipids. Cyclic [G(2',5')pA(3',5')p] (2'3'-cGAMP) was acquired from InvivoGen. Fluorescamine was purchased from MP Biomedicals. Sulfo-Cy5.5 NHS ester was acquired from Lumiprobe. Microvette 500 Z-Gel serum collection vials with clotting factor were obtained from Sarstedt. Matrigel Basement Membrane Matrix was purchased from Corning. Gold and iron ICP standards were purchased from Fluka Analytical.

Mice

All animal experiments were conducted according to the protocols approved by the University of Michigan Committee on Use and Care of Animals (UCUCA). BALB/c mice ages 5-7 weeks were purchased from Charles River Labs.

Cells

All cells were maintained at 37° C., 5% $CO_2$/95% air atmosphere and approximately 85% relative humidity. D2F2/E2 cells (provided by Dr. Wei-Zen Wei)" were cultured in complete DMEM high glucose supplemented with 10% NCTC 109 media, 1% L-glutamine, 1% MEMs non-essential amino acids, 0.5% sodium pyruvate, 2.5% sodium bicarbonate, 1% pen/strep, 5% cosmic calf serum, 5% fetal bovine serum, 500 μg/mL Geneticin and 50 μM 2-mercaptoethanol. RAW264.7 macrophages were cultured in complete RPMI-1640 media supplemented with 10% fetal bovine serum, 1% L-glutamine, 1% MEMs non-essential amino acids, 1% sodium pyruvate and 1% pen/strep. Primary B-cells were cultured in RPMI-1640 media supplemented with 10% heat-inactivated fetal bovine serum.

Formulation and Characterization of Virus-Spiky-Mimicry B Cell Nanovaccine (VSMB)

The VSMB was formulated based on previously reported protocols by our group with minor modifications. The final Au to Fe ratio of the formulated VSMB was quantified by inductively coupled plasma mass spectrometry (ICP-MS) using a Perkin-Elmer Nexion 2000 based on previously reported protocols modified from analysis by ICP-OES. VSMB formulations were imaged by s scanning transmission (electron microscopy (STEM) using a JEOL 2100F with a CEOS probe corrector. The true particle size of AuNPs, DPNVs and VSMBs was quantified using ImageJ software. The volume-weighted hydrodynamic particle size, polydispersity index and zeta-potential of all formulations in milliQ water at 25° C. was evaluated with the Malvern Zetasizer Nano-ZS using dynamic light scattering and phase analysis light scattering, respectively.

Lipid-Coated Iron-Oxide Nanovaccine (DPNV)

Lipid-coated iron-oxide nanoparticles were prepared based on previously reported methods for thin-film hydration with minor modifications. DSPE-PEG (2000)-maleimide (10 mg) was added to 1 mg of 30-nm iron-oxide nanoparticles stabilized by oleic acid in chloroform as gently mixed. The resulting solution was subjected to solvent rotary evaporation to remove all chloroform and form a thin film. Simultaneously, this film and 100 mM PBS, pH 7.4 were heated to 75° C. in an oven. Upon reaching temperature, hot PBS was rapidly added to the film and mixed immediately and vigorously to facilitate thin film hydration. The resulting nanoparticle solution was stored at 4° C. to promote lipid self-assembly. Free phospholipid was removed by magnetic separation overnight at 4° C. using the EasySep™ magnetic separator device (StemCell Technologies).

DPNV-HER2 and VSMB-HER2 Formulations

HER2 peptides were conjugated to both DPNV and VSMB through thiol-mediated chemistries. Specifically, DPNV-HER2 was formulated via maleimide chemistry and VSMB-HER2 was formulated via the gold-thiol linkage. HER2 peptide was added to DPNV at 1.5× weight ratio excess in milliQ and incubated overnight at 4° C. HER2 peptide was added to VSMB-HER2 at 5× weight ratio excess in milliQ and incubated overnight at 4° C. Both materials were purified either by magnetic separation overnight at 4° C. using magnetic separation, or by centrifugal separation at 10,000×g for 30 minutes at 4° C. Peptide loading was determined using fluorescent quantification using a modified fluorescamine peptide quantification assay in the presence of nanoparticles (Ex/Em: 390/465 nm, Biotek Cytation 5)[74]. Quantification was performed using a standard curve with increasing peptide concentration with standardized concentration of nanoparticles (DPNV or VSMB) to account for quenching effects.

Murinized Pertuzumab and Trastuzumab

Murinized Trastuzumab (Murine 4D5): Mouse IgG2a constant chain chimeric with same variable region as human Trastuzumab (Herceptin®). Murinized Pertuzumab (Murine 2C4)[76]: Mouse IgG2a constant chain chimeric with same variable region as human Pertuzumab (Perjeta®). Both antibodies were synthesized by GenScript.

a. Murinized Trastuzumab (Murine 4D5) Amino Acids Sequences:

Heavy Chain Variable region:
(SEQ ID NO: 6)
EVQLQQSGPELVKPGASLKLSCTASGFNIKDTYIHWVKQRPEQGLEWIG

RIYPTNGYTRYDPKFQDKATITADTSSNTAYLQVSRLTSEDTAVYYCSR

WGGDGFYAMDYWGQGASVTVSS

Heavy Chain constant region (Mouse IgG2a):
(SEQ ID NO: 7)
AKTTAPSVYPLAPVCGDTTGSSVTLGCLVKGYFPEPVTLTWNSGSLSSG

VHTFPAVLQSDLYTLSSSVTVTSSTWPSQSITCNVAHPASSTKVDKKIE

PRGPTIKPCPPCKCPAPNLLGGPSVFIFPPKIKDVLMISLSPIVTCVVV

DVSEDDPDVQISWFVNNVEVHTAQTQTHREDYNSTLRVVSALPIQHQDW

MSGKEFKCKVNNKDLPAPIERTISKPKGSVRAPQVYVLPPPEEEMTKKQ

VTLTCMVTDFMPEDIYVEWTNNGKTELNYKNTEPVLDSDGSYFMYSKLR

VEKKNWVERNSYSCSVVHEGLHNHHTTKSFSRTPGK

Light Chain Variable region:
(SEQ ID NO: 8)
DIVMTQSHKFMSTSVGDRVSITCKASQDVNTAVAWYQQKPGHSPKLLIY

SASFRYTGVPDRFTGNRSGTDFTFTISSVQAEDLAVYYCQQHYTTPPTF

GGGTKLEIK

Light Chain constant region (Mouse Ig Kappa):
(SEQ ID NO: 9)
RADAAPTVSIFPPSSEQLTSGGASVVCFLNNFYPKDINVKWKIDGSERQ

NGVLNSWTDQDSKDSTYSMSSTLTLTKDEYERHNSYTCEATHKTSTSPI

VKSFNRNEC b. Murinized Pertuzumab (Murine 2C4) Amino Acids Sequences:

Heavy Chain Variable region:
(SEQ ID NO: 10)
EVQLQQSGPELVKPGTSVKISCKASGFTFTDYTMDWVKQSHGKSLEWIG

DVNPNSGGSIYNQRFKGKASLTVDRSSRIVYMELRSLTFEDTAVYYCAR

NLGPSFYFDYWGQGTTLTVSS

Heavy Chain constant region (Mouse IgG2a):
(SEQ ID NO: 11)
AKTTAPSVYPLAPVCGDTTGSSVTLGCLVKGYFPEPVTLTWNSGSLSSG

VHTFPAVLQSDLYTLSSSVTVTSSTWPSQSITCNVAHPASSTKVDKKIE

PRGPTIKPCPPCKCPAPNLLGGPSVFIFPPKIKDVLMISLSPIVTCVVV

DVSEDDPDVQISWFVNNVEVHTAQTQTHREDYNSTLRVVSALPIQHQDW

MSGKEFKCKVNNKDLPAPIERTISKPKGSVRAPQVYVLPPPEEEMTKKQ

VTLTCMVTDFMPEDIYVEWTNNGKTELNYKNTEPVLDSDGSYFMYSKLR

VEKKNWVERNSYSCSVVHEGLHNHHTTKSFSRTPGK

Light Chain Variable region:
(SEQ ID NO: 12)
DTVMTQSHKIMSTSVGDRVSITCKASQDVSIGVAWYQQRPGQSPKWYSA

SYRYTGVPDRFTGSGSGTDFTFTISSVQAEDLAVYYCQQYYIYPYTFGG

GTKLEIK

Light Chain constant region (Mouse Ig Kappa):
(SEQ ID NO: 13)
RADAAPTVSIFPPSSEQLTSGGASVVCFLNNFYPKDINVKWKIDGSERQ

NGVLNSWTDQDSKDSTYSMSSTLTLTKDEYERHNSYTCEATHKTSTSPI

VKSFNRNEC

Tumor Studies

BALB/c mice were inoculated with $2.5 \times 10^5$ D2F2/E2 cells subcutaneously in the right flank. D2F2/E2 cells were prepared at $2.5 \times 10^6$ cells/mL in 100 µL and mixed at equal volume with Matrigel matrix. Tumor size was quantified by caliper measurements every 7 days. Tumor volumes were calculated by volume=(width)$^2$×length/2. End points were determined by using the End-Stage Illness Scoring System; mice receiving an End-Stage Illness Score greater than 6 were euthanized by $CO_2$ asphyxiation. Mice were labelled by 3% Picric acid Ethanol solution. Mice were immunized with 50 µg amount of HER2 epitope (same mole amount of E75/HER2-T cell epitopes) 2 days after inoculation one time per week for 3 doses. 10 µg 2'3'-cGAMP was used for adjuvant (5 µg GM-CSF was used for E75). 100 µg Anti-mouse PD-1 antibody were injected 1 day and 4 day after every immunization. 50 µg LIGHT protein was used for dosing mixed with VSMB and soluble HER2 epitope before vaccination. 100 µg murinized Trastuzumab was dosed 1 day after immunization for 3 times. For anti-mouse PD-1 and murinized Pertuzumab groups, 100 µg Anti-mouse PD-1 antibody was dosed 7 days after inoculation biweekly. 100 µg murinized Pertuzumab was injected 7 days after inoculation once per week. For prophylactic experiments, mice were immunized at day 0, day 14, day 28 and day 49. Tumor challenge were then inoculated at day 49.

Mass Cytometry (CyTOF) to Analyze Immune Pattern from Lymph Nodes and Tumors

Lymph node and tumor samples were harvested and dissociated into single cell suspension 10 days after the second boost of vaccination. Fixed and frozen cell suspensions were thawed on ice. Samples were stained and prepared for CyTOF analysis as previously described, using an optimized cocktail of 40 metal-conjugated antibodies designed to identify major and minor immune cell subsets in lymph nodes. Following acquisition on a CyTOF II (Fluidigm, San Francisco, CA), samples were normalized to internal bead standards. Cell subsets were identified by gating using FlowJo software. Global analysis using SPADE were performed for unsupervised clustering analysis based on the expression of marked genes in different subset of immune cells.

Immunohistochemistry (IHC) Staining of Tumor Tissues

Tumor tissues were harvested at the end points or observation end point, and immediately go through paraformaldehyde fixation. The fixation tissues are then embedded in paraffin and cut by microtome to 5 µm and affixed to slides for later staining processes. After deparaffinization, rehydration and antigen unmasking, slides were then reacted with primary and secondary antibodies and developed for counterstaining. Phenotype markers include: CD20, CD3, CD21 and FOXP3.

Immunofluorescent Staining of Lymph Nodes and Tumor Tissues

For distribution investigation, lymph nodes and tumor tissues were harvested 24 hours after dosing. For TLSs immunofluorescent staining, tumor tissues were harvested at the end points or observation end point. Harvested tissues were immediately gone through 1% paraformaldehyde fixation for 1 hours and then immersed into 30% sucrose in 0.1% NaN3 in PBS overnight. Treated tissues were then embedded in OCT compound and freeze in $CO_2$(s)+EtOH bath. 15 μm slides were cut and dried for 3 hours before staining. After incubation with blocking buffer and staining solution, slides were then mounted with Fluoromount-G® or DAPI Fluoromount-G® for confocal imaging. Brilliant Violet605 CD19 and Alexa Fluor® 594 CD169 were used for lymph node staining. Alexa Fluor® 594 CD19, FITC CD3 and Alexa Fluor® 647 anti-mouse CD21/CD35 (CR2/CR1) were used for tumor staining.

Quantification of Nanoparticle Delivery to Lymph Nodes In-Vivo

Mice were injected subcutaneously in the left hock with either DPNV or VSMB at a dose of 200 μg Fe per mouse. At the designated time intervals, mice were sacrificed and lymph nodes of interest were dissected for ex-vivo analysis. The extent of nanoparticle delivery to the lymph nodes was quantified using ICP-MS based on previously reported protocols.

Quantification of Peptide Delivery to Lymph Nodes In-Vivo

To facilitate quantification of peptide delivery to lymph nodes, lysine terminally modified HER2 peptides were chemically conjugated to sulfo-Cy5.5 NHS Ester. This conjugation was carried out at a 5-fold molar excess of sulfo-Cy5.5 NHS Ester to HER2 peptide. DPNV-HER2-Cy5.5 and VSMB-HER2-Cy5.5 were subjected to Cy5.5 functionalization after initial peptide conjugation was completed to enable facile purification of excess fluorescent dye by magnetic separation. Subsequent to Cy5.5 functionalization, mice were injected as previously stated. After 3 hours, mice were sacrificed and lymph nodes of interest were dissected for ex-vivo analysis by IVIS imaging. IVIS imaging was utilized for semi-quantification of peptide delivery in terms of radiant efficiency.

In-Vivo Cell Uptake

VSMB-HER-Cy5.5 and DPNV-HER2-Cy5.5 were injected subcutaneously in the left hock with either Lipid-DPNV or VSMB at 200 μg total Fe per mouse. At 3 hours and 24 hours, mice were sacrificed and lymph nodes of interest were dissected for ex-vivo analysis by flow cytometry. Lymph nodes were dissociated by mechanical methods to prepare single cell suspensions. Single cell suspensions of lymph node cells were stained for analysis by flow cytometry using the MoFlo Astrios flow cytometer. Viable cells (Zombie UV) were identified as either B-cells (B220$^+$) or subcapsular sinus macrophages (CD169$^{high}$CD11b$^+$) and evaluated for positive nanoparticle interactions (Cy5.5). Flow cytometry data was analyzed by FCS express.

In-Vitro Cell Uptake

VSMB-HER2 and DPNV-HER2 cellular uptakes were evaluated in RAW264.7 macrophages, dendritic cells (DC 2.4), and primary B-cells isolated from murine spleens using an EasySep Mouse B-cell isolation kit. Nanoparticle samples were incubated at 50 μg/mL Fe with cells for 18 hours in blank RPMI media at 37° C., 5% $CO_2$/95% air atmosphere and approximately 85% relative humidity. After 18 hours, cells were lifted by cell scraping and washed thrice with PBS. Following the wash steps, resulting cell pellets were re-suspended in 1 mL of PBS, cell counted and then digested in 1 mL aqua regia (1:3 molar ratio nitric acid:hydrochloric acid) for analysis by ICP-MS.

Investigation of Crosslinking Activation

Quasi-Monoclonal (QM) mice is a mouse model for studying the generation of antibody diversity. The primary repertoire of B cell receptor is monospecific towards Hapten (4-hydroxy-3-nitrophenyl) acetyl (hapten-NP). And the Hapten (4-hydroxy-3-nitrophenyl) acetyl (hapten-NP) specific B Cells were isolated from splenocytes of QM mice through negative selection using EasySep™ Mouse B Cell Isolation Kit.

1. Early Activation

QM mice were immunized with soluble epitope, DPNV and VMSB in equal amount (50 μg) of epitope. Lymph nodes were harvested and dissociated into single cell suspension 6 hours after vaccination. FITC-CD19 and APC/Cyanine7 anti-mouse CD86 were then incubated with hapten-NP specific B cells for flow cytometry analysis.

2. B-Cell Calcium Flux Assay and Data Analysis

Hapten-NP B cells isolated from QM mice (1*10$^7$ cells/mL) were then incubated with Fluo-4 AM (10 μM) for 30 mins at 37° C. Fluo-4 AM labelled cells (2*10$^6$ cells/mL) were then transferred to 96-well microplate and incubated with soluble antigen, DPNV and VSMB in an equal concentration of antigen (20 nM). Real-time flux assays (6 s/time before adding antigen for 1 min, 3 s/time after adding antigen for 6 mins) were then conducted on a microplate reader (Biotek Cytation5) with 5 repeated samples. DPBS were used as blank control and Cells incubated with DPBS were serve as an experimental control. Normalized calcium signals were obtained by subtracting blank control calcium signals from original calcium signals with same numbering in experimental groups. Then the 5 repeated calcium signals at different groups were averaged for every timepoints as $I_{average}$. The maximum average of normalized calcium signal ($I_{max}$) among all the groups across all time points were set as standard ('1'). $I_{average}$ were then divided by the $I_{max}$ to get the normalized calcium signal ratio for plotting.

3. Crosslinking Activation Imaging

Hapten-NP B cells isolated from QM mice (5*10$^6$ cells/mL) were then incubated with 20 μg/ml Alexa Fluor® 488 AffiniPure Fab Fragment Goat Anti-Mouse IgM on ice for 30 mins in dark (Jackson: 115-547-020). Cells washed (2*10$^6$ cells/mL) were then incubated with antigen (equal amount of epitope, 20 nM, Cy3 labelled) at a total volume of 400 μL for 1 min, 3 mins and 5 mins at 37° C., respectively. After antigen incubation, cells were then fixed by 6% paraformaldehyde (800 μL) for 10 mins at 37° C. After fixation, cells were then permeabilized by 0.1% Triton-X HBSS solution (800 μL) for 10 mins. After permeabilization, cells were then incubated with Alexa Fluor™ Plus 405 Phalloidin in staining buffer (200 μL, 5 mg/mL BSA, 0.1% Triton-X in HBSS) on ice for 2 hours. After twice washing, cells were then planted onto 0.1% poly-1-lysine pretreated eight-well glass chambers (LabTech II) on ice for at least 4 hours before confocal imaging.

Antigen-Specific B-Cell and Germinal Center Flow Cytometry

Mice were immunized as previously introduced. At day 10, mice were sacrificed and lymph nodes were dissected for ex-vivo analysis by flow cytometry. Antigen-specific B-cell analysis was accomplished using tetramer staining based on previously established protocols with minor modifications. HER2/neu peptide tetramers were prepared by mixture of biotin-labeled HER2 peptide with Alexa Fluor 647 labeled streptavidin at a 4:1 molar ratio at room temperature for 1 hour without further purification. Antigen-specific B-cell population was identified using CD19, and the HER2-peptide tetramer using flow cytometry. Germinal center B-cell populations were identified using the following markers B220, IgD, GL7 and CD95 (B220$^+$IgD$^{low}$GL7$^+$CD95$^+$).

Immunizations and Serum Collection

At day 0, mice were immunized with the equivalent of 50 μg or 5 μg of HER2 peptide plus 10 μg of 2'3'-cGAMP regardless of formulation type. Subsequently, at day 14, mice were boosted twice at two-week intervals with 50% of the original dosage for both antigen and adjuvant (day 14 and 28). To evaluate serum antibody titers, blood was collected by submandibular puncture 10 days after each immunization (day 10, 24 and 38). Serum was separated from whole blood by centrifugal separation at 10,000×g for 5 minutes at 25° C. using the Microvette 500 Ser-Gel collection vessels with clotting activator.

Enzyme-Linked Immunosorbent Assay (ELISA)

Absolution quantification of total IgG and total IgM antibody analysis was performed using the mouse uncoated total IgG and total IgM ELISA kits based on manufacturer recommended protocols (Thermo Fisher). Antigen-specific IgG, IgG1 and IgG2a antibody titers were quantified based on previously established protocols for indirect ELISA with minor modifications[81]. Specifically, HER2 peptides (200 μL, 100 μg/mL in 100 mM carbonate buffer, pH 9.4) were chemically conjugated to ELISA plates through the terminal amine group utilizing Nunc Immobilizer Amino immunoassay plates by overnight incubation with exposure to light at room temperature. Following overnight incubation, ELISA plates were washed three times with 100 mM PBS, pH 7.4 with 2% Tween-20. Subsequently, ELISA plates were blocked overnight at 4° C. with 300 μL of ELISA blocker (Pierce Protein-Free PBS Blocking Buffer). Following blocking, the ELISA plates were washed 3×. Serum samples containing primary antibodies were serially diluted ($10^1$-$10^8$ fold) using 100 mM PBS, pH 7.4 containing 10% ELISA blocker reagent and added to each well at 200 μL total for 2 hour incubation at room temperature. Following sample addition, the ELISA plates were washed 3×. 500-fold diluted anti-IgG-HRP, anti-IgG1-HRP, or anti-IgG2a-HRP was added at 100 μL to each well and incubated for 1 hour at room temperature. After 1 hour, the ELISA plates were washed 5×. Next, 100 μL of 1-Step Ultra TMB Substrate Solution was added to each well and allowed to incubate and develop color for 15-20 minutes at room temperature with gentle agitation. After 15-20 minutes, color development was stopped by the addition of 100 μL of 100 mM sulfuric acid. Colorimetric development was quantified by absorbance spectroscopy at 450 nm using the BioTek Cytation 5 plate reader. Antibody titers were determined by any absorbance signal at a given dilution factor that was greater than the PBS control absorbance signal plus three standard deviations.

Statistics

Data are expressed as mean±standard deviation (SD), unless otherwise specified. Comparisons between two groups were made using the unpaired Student's t-test. Means of multiple groups were compared with the one-way analysis of variance (ANOVA), followed by post hoc Tukey's pairwise comparisons. All probability values are two-sided, and values of $p<0.05$ were considered statistically significant. Statistical analyses were carried out using the GraphPad Prism 7 software package.

Mathematical Modeling:

Gold Nanoparticle (AuNP) Loading Per Inorganic-Virus Like Nanoparticle (VSMB)

The extent of gold nanoparticle (AuNP) loading to inorganic virus-like nanoparticle (VSMB) surfaces was determined by ICP-MS determination of total elemental gold (Au) and iron (Fe) weights. These weights were then utilized to quantify total number spheres of a given element and particle size based on previously reported methods. The ratio of these experimental values was then interpreted as AuNPs per VSMB, or the number of AuNPs per single DPNV core.

Due to the crystalline structure of iron-oxide nanoparticles, it is possible to quantify the number of nanoparticles per unit Fe based on known particle size accordingly to previously establish methodologies (Table 7).

TABLE 7

| Channel | Specificity |
| --- | --- |
| 112Cd | CD19 |
| 141Pr | IFNg |
| 142Nd | CD86 |
| 143Nd | CD80 |
| 144Nd | Siglec-F |
| 145Nd | CD4 |
| 146Nd | B220 |
| 147Sm | CD206 |
| 148Nd | CD138 |
| 149Sm | CD8 |
| 150Nd | mPDCA-1 |
| 151Eu | DX5 |
| 152Sm | Ly-6C |
| 153Eu | IFNb |
| 154Sm | CD11c |
| 155Gd | IA-IE |
| 156Gd | CD25 |
| 158Gd | TIM-3 |
| 159Tb | Ly-6G |
| 160Gd | Il-4 |
| 161Dy | Il-17a |
| 162Dy | TCRγδ |
| 163Dy | Il-17f |
| 164Dy | Il-10 |
| 165Ho | CD115 |
| 166Er | Cxcr5 |
| 167Er | FR4 |
| 168Er | NOS2 |
| 169Tm | Ly-6A/E |
| 170Er | CD62L |
| 171Yb | CD44 |
| 172Yb | CD11b |
| 173Yb | PD-1 |
| 174Yb | CTLA-4 |
| 175Lu | F4/80 |
| 176Yb | GmzB |
| 209Bi | CD3 |
| 89Y | CD45 |
| 195Pt | Viability |
| 191/193Ir | DNA |

Using transmission electron microscopy (TEM), the exact particle size of iron-oxide nanoparticles was quantified using the ImageJ software. The particle size of the polymer-coated iron-oxide nanoparticle core of the VSMB was 15 nm, while the particle size of the lipid-coated iron-oxide nanoparticle control was 30 nm. Based on the known unit cell volume of iron-oxide ($Fe_3O_4$) and quantified particle size, the number of nanoparticles per gram Fe was determined to be $1.5\times10^{17}$ and $1.9\times10^{16}$ for 15 nm and 30 nm cores, respectively (Table 7).

The number of gold nanoparticles per unit Au was quantified by two considerations. First, based on literature values reported by Lu et al, AuNPs with 3 nm diameters have 479 gold atoms per nanoparticle, which is 56% of the number of gold atoms per solid gold metallic colloids of the same diameter (835 gold atoms per nanoparticle). Therefore, by conversion from weight of Au to atoms of Au through Avogadro's Number it is possible to quantify the number of gold nanoparticle per unit Au. Quantification by this methodology revealed that number gold nanoparticle per gram Au was $6.38\times10^{17}$ (Table 8).

TABLE 8

Iron-oxide nanoparticle calculations. Quantification of total number of spheres per unit Fe and total surface area per unit Fe for 15-nm and 30-nm iron-oxide nanocrystal cores. Calculations were performed based on equations outlined previously by Kokate et al.

| Description | Value |
|---|---|
| Unit cell volume of $Fe_3O_4$ | 0.5905 $nm^3$ |
| Fe atoms per unit $Fe_3O_4$ cell | 24 |
| Molecular weight of Fe | 55.85 g/mole |
| Avogadro's Number | $6.022 \times 10^{23}$ |
| Volume of 15 nm IONP core - single sphere | 1766 $nm^3$ |
| Volume of 30 nm IONP core - single sphere | 14130 $nm^3$ |
| Surface Area per Sphere - 15 nm IONP core | 707 $nm^2$ |
| Surface Area per Sphere - 30 nm IONP core | 2826 $nm^2$ |
| Number of Fe atoms per g Fe | $1.08 \times 10^{22}$ |
| Number of $Fe_3O_4$ unit cells per g Fe | $4.5 \times 10^{20}$ |
| Number of $Fe_3O_4$ unit cells per Single Sphere - 15 nm IONP core | 2944 |
| Number of $Fe_3O_4$ unit cells per Single Sphere - 30 nm IONP core | 23550 |
| Total Number of Spheres per g Fe - 15 nm IONP core | $1.5 \times 10^{17}$ |
| Total Number of Spheres per g Fe - 30 nm IONP core | $1.9 \times 10^{16}$ |
| Total Surface Area per g Fe - 15 nm IONP core | $1.1 \times 10^{20}$ $nm^2$ |
| Total Surface Area per g Fe - 30 nm IONP core | $2.7 \times 10^{20}$ $nm^2$ |

TABLE 9

Gold nanoparticle calculations. Quantification of total number of spheres per unit Au for 3 nm AuNPs

| Description | Value |
|---|---|
| Method 1 | |
| Density of Gold | 19.32 $g/cm^3$ |
| Atomic Number | 197 |
| Average # of Gold Atoms per AuNP (3 nm) | 479 |
| Number of AuNPs per g Fe (3 nm) | 6.38E+18 |
| Method 2 | |
| Mass of Single AuNP (g) | 2.67E−19 |
| Number of AuNPs per g Au (3 nm) | 3.67E+18 |

Gold Nanoparticle Spatial Distribution—Inter-Nanoparticle Distance

The distance between AuNPs on VSMB surfaces was modeled based on two methodologies. The first technique was based on the arc length equation for a circle. If homogeneous distribution of AuNPs on a sphere is assumed, the loading of 2, 6 and 14 AuNPs on VSMB surface will yield AuNPs in a single plane (circle) oriented at central angles equivalent to 180°, 90° and 45°, respectively. Using the arc length equation for a circle with radius 7.5 nm, 2, 6 and 14 AuNPs will be located 23.6, 11.8 and 5.9 nm apart, respectively. Plotting these three points and using a power function curve fitting model ($R^2$=0.99) allows for interpolations of inter-nanoparticle distances between 2-14 AuNPs per VSMB surface (Table 9). The benefit of this technique is that it accounts for arc length and is not a straight-line distance calculation. However, this model represent AuNPs are single points and only has three points for the curve fitting model thereby limiting potential power and accuracy.

The second technique used to quantify inter-nanoparticle distance on VSMB surfaces was based on a triangulation methodology. With the number of AuNPs per VSMB surface known and assuming homogeneous distribution of AuNPs on a sphere around a single central focal point, AuNPs can be triangulated. For AuNP per VSMB equal to or greater than 4, the number of triangles formed around a central focal point is 2n, where n is the number of AuNPs per VSMB.

AuNP Triangles per IONP core=AuNP per IONP core×2

With the number of triangles determined, the surface occupied by a single triangle was quantified given the surface area of spherical VSMB with 7.5 nm radius.

$$\text{Surface Area per Triangle} = \frac{\text{Surface Area of IVLN}}{\text{Number of Triangles}}$$

Assuming an equilateral triangle, the surface area of a single triangle can be used to determine the length of a side of the triangle, and therefore the distance between AuNPs represented as single points. By subtracting 2× the radius of the AuNPs, a better surface to surface contact distance can be interpreted (Table 10).

$$\text{Distance between AuNPs} = \sqrt{\frac{4 \times \text{Triangle Surface Area}}{\sqrt{3}}} - (2 \times \text{AuNP radius})$$

The benefit of this technique is that does not rely on interpolation. However, this model is limited due to the reliance of straight-line distances between AuNPs.

TABLE 10

Inter-nanoparticle distance: Arc Length Interpolation Model. Interpolation data set for inter-AuNP distances based on AuNP per VSMB determined by ICP-MS (FIG. 2.2A) and the curve fitting model ($y = 39.51x^{-.708}$, $R^2 = 0.99$).

| Au/Fe Ratio (wt/wt) | AuNP per VSMB | Inter-Nanoparticle Distance Arc Length (nm) |
|---|---|---|
| 0.05 | 2.1 | 23.18 |
| 0.1 | 4.2 | 14.19 |
| 0.15 | 6.4 | 10.65 |
| 0.2 | 8.5 | 8.69 |
| 0.25 | 10.6 | 7.42 |
| 0.3 | 12.7 | 6.52 |
| 0.35 | 14.9 | 5.84 |
| 0.4 | 17.0 | 5.32 |

TABLE 11

Inter-nanoparticle distance: Triangulation Model. Data set for inter-AuNP distances based on AuNP per VSMB determined by ICP-MS (FIG. 2.2A) and mathematic modeling presented above, and curve fitting model presented in FIG. S2 ($y = 28.69x^{-.649}$, $R^2 = 0.99$).

| Au/Fe Ratio (wt/wt) | AuNP per VSMB | Inter-Nanoparticle Distance Arc Length (nm) |
|---|---|---|
| 0.05 | 2.1 | 17.10 |
| 0.1 | 4.2 | 11.36 |
| 0.15 | 6.4 | 8.82 |
| 0.2 | 8.5 | 7.30 |
| 0.25 | 10.6 | 6.27 |
| 0.3 | 12.7 | 5.50 |
| 0.35 | 14.9 | 4.91 |
| 0.4 | 17.0 | 4.43 |

TABLE 5

VSM material properties before and after peptide conjugation under saturating conditions.

|  | VSM Blank | VSM Peptide |
|---|---|---|
| Particle Size (nm) | 52 ± 3 | 60 ± 2 |
| Polydispersity Index (PDI) | 0 19 ± 0.04 | 0.20 ± 0.03 |
| Zeta-Potential (mV) | −16 ± 4 | −17 ± 1 |

TABLE 6

Lipid-coated IONP material properties before and after peptide conjugation under saturating conditions.

|  | Lipid IONP | IONP-HER2 |
|---|---|---|
| Particle Size (nm) | 52 ± 4 | 68 ± 5 |
| Polydispersity Index (PDI) | 0.16 ± 0.05 | 0.22 ± 0.02 |

Second, based on literature values reported for the mass of a single AuNP for 2 nm, 5 nm and 10 nm particle size, the mass of a single 2 nm AuNP was interpolated based on curve fitting. Through curve fitting, the mass of a single 3 nm AuNP was determined to be $2.67 \times 10^{-19}$ grams or $3.67 \times 10^{18}$ AuNPs per gram Au (Table 8). Notably, this quantified value matches those values reported for solid gold colloids based on 835 gold atoms per nanoparticle and is therefore was not considered truly representative of our materials.

Generation of Virus-Spike-Mimicry B Cell Nanovaccine (VSM NanoVax) to Resemble Virus Spiky Peplomer-Like Antigen Cluster Topography In order to stimulate a robust Tfh cell dependent B cell activation, three features are important for the antigen display on the surface of nanoparticles: spiky antigen cluster topography, distance (e.g., about 5 nm) between antigen clusters, and localized high antigen density on the spike.

Firstly, we have developed a facile and controllable protocol to manufacture viral-like spiky topography of VSM NanoVax through self-assembly process. The Au nanodots (AuND) (or "satellites") (2 nm) were attached onto the surface of poly(siloxane) and poly (ethylene glycol) containing di-block co-polymer coated iron nanoparticle (IONP, 15 nm) to produce the spiky topography as we previously reported. The attachment of AuND onto IONP was achieved by self-assembly from the interaction between reactive AuND surfaces and free siloxane moieties present in the polymer used to coat the IONP. This process is controlled and robust for facile large-scale manufacture. To control the optimal distance between spiky antigen clusters at 5-10 nm, which is an important distance for BCR crosslinking and activation, we adjusted the distance/density of viral-like spiky structures on VSM NanoVax surfaces using different ratios of AuND/IONP, which yielded with 4±2, 9±3 and 13±5 AuND per VSMB (distance between 5.1-20 nm). To mimic the optimal viral size and surface charge, VSM NanoVax have around 50-60 nm particle size, 0.2 PDI and a −16 mV zeta-potential. In addition, under in-vivo relevant serum conditions, VSM NanoVax were shown to be stable between 12 and 24 hours.

Secondly, the spiky antigen cluster topography was achieved by conjugating antigen peptides with cysteine at the N-terminus pinpoint to the spiky AuND of VSM NanoVax through thiol-Au reaction. We used a HER2 B cell epitope with an overlapping CD4 T-cell epitope (CDDDPESFDGDPASNTAPLQPEQLQ-(GGK) (SEQ ID NO:3). High levels of peptide conjugation were observed for VSM NanoVax with AuND, but not on the IONP core alone. Additionally, a positive correlation between peptide loading and AuND number were observed (R=0.95). These results suggest that, although there is a low-level non-specific association of HER2 peptides to IONP core (~12%), peptide conjugation is AuND dependent, which achieved antigen spiky cluster topography on VSM NanoVax; these viral mimicry feature cannot be achieved by traditional nanoparticles that only have uniform Antigen distribution on their surface. To control the highly localized antigen density on the spike, we conjugated different amount of HER2 peptides on VSM NanoVax with 0%, 10% and 30% AuND/IONP ratios, which correspond to 0, 4, 13 AuND on VSMB surface, respectively. The peptide loadings were 232±73, 888±42 and 1954±157 peptides per VSM NanoVax (227±5 peptides per AuND). Therefore, VSM NanoVax achieved an density of 20,000-25,000 antigen clusters per $\mu m^2$, which is comparable to the antigen density reported for VLPs (e.g. Hepatitis B Virus, ~20,000 antigen).

To evaluate these three unique features of viral-mimicry structures of VSM NanoVax, in vivo animal test with different distance of viral spikes and density of antigen clusters were conducted. Immunization with same HER2 antigen dose, VSM NanoVax (14 antigen clusters with ~5 nm distance between clusters, high antigen density 150 peptides/cluster) generated 4-fold higher titer of antigen-specific antibody than VSM NanoVax (4 antigen clusters with ~15 nm distance between clusters, low antigen density 30 peptides/cluster). The data suggest that important antigen clusters (about 14 clusters), important distance between antigen clusters (about 5-6 nm), and important localized antigen density (about 2000 peptides/VSM NanoVax, ~150 peptides/AuND) generated high HER2-specific antibody.

To effectively evaluate these three unique features of viral-mimicry structures of VSM NanoVax, a traditional lipid-coated IONP (IONP-HER2) with similar size, charge, peptide density (2323±394 peptides per IONP, but without a spiky topography) on the surface was generated as a control. IONP-HER2 has a 30-nm IONP core and a functionalized DSPE-PEG (2000)-maleimide shell that facilitates facile peptide conjugation. IONP-HER2 has similar material properties in terms of volume-weighted hydrodynamic particle size (68±5 nm), PDI (0.22±0.02) and maximal number per particle (2323±394 peptides per IONP).

Virus-Spike-Mimicry B Cell Nanovaccine (VSM NanoVax), Combined with Anti-PD-1 Antibody, Induced TLS Formation and Achieved Cancer Remission in HER2+ Breast Cancer The therapeutic efficacy of VSM NanoVax (with virus spike mimicry and LIGHT in the formulation) was evaluated in the HER2+ breast cancer in combination with anti-PD-1 antibody. VSM NanoVax (three vaccination doses) inhibited tumor growth by 90% and achieved cancer remission in 44% mice (4/9, >200 days). This data is significant since most other cancer vaccines in combination with anti-PD-1/PD-L1 only exhibit short-term anticancer efficacy (<1-3 months) without achieving long term cancer remission.

Immunostaining demonstrated that VSM NanoVax (with virus spike mimicry and LIGHT in the formulation) induced substantial TLS formation inside tumors, which were marked by rich B cell zones surrounded by T cell zones, as well as the follicular dendritic cells (FIG. 12). These cell compositions in the TLS are similar to the reported TLS in human cancer patients who have better clinical responses to anti-PD-1 therapy. Interestingly, VSM NanoVax was also observed in the tumor tissues, which was co-localized with B cells in the tumors. These data suggest that the long term efficacy of VSM NanoVax in combination with anti-PD-1 antibody to achieve cancer remission may be benefited from the formation of B cell-rich TLS in the tumors.

In order to investigate the effect of virus spike mimicry of the nanoparticle, we compared the anticancer efficacy of VSM Nano (without LIGHT) and IONP (without LIGHT) with same HER2 antigens (B cell epitope+CD4 T cell epitope). The VSM NanoVax (without LIGHT) significantly inhibit cancer growth (by 70%) and achieves cancer remission in 11% of mice (1/9, >200 days), while INOP Vax only slightly inhibited tumor growth by 30% (P>0.05 vs. control). These data suggest virus spike mimicry is important for its efficacy of VSM NanoVax. It worth noting that VSM Nano with HER2 T cell epitope (E75) did not exhibit significant anticancer efficacy (P>0.05 vs. control). None of other groups have exhibited significant inhibition of cancer growth (P>0.05 vs. control) (FIG. 12).

In addition, we also compared the efficacy between VSM Nano with B cell epitope (without LIGHT) and anti-HER2 antibody treatment (mαHER2, which is equivalent to clinical used Pertuzumab against the same B cell epitope) and clinically used formulation of HER2 T-cell cancer vaccine (E75+GM-CSF), in combination with anti-PD-1 antibody. VSM Nano with B cell epitope achieved significantly better efficacy compared to mαHER2 antibody treatment or E75 T cell vaccine treatment, although the plasma antibody levels of mαHER2 group (~21300 units at 6 hours after injection and −10700 unit at 2 days after injection) is higher than the plasma HER2 specific antibody levels in VSM Nano vaccine group at 10 days after vaccination. These data suggest the efficacy of VSM Nano B cell vaccine is benefited from other factors in addition to antibody production. Furthermore, VSM Nano with B cell epitope (without LIGHT) also stimulated the B cell-rich TLS formation inside tumors although they are less obvious compared to with VSM NanoVax (with LIGHT) (FIG. 12). In contrast, T cell cancer vaccine (E75+GM-CSF) group slightly increased T cell infiltrating, but rare B cell infiltrating and no B/T cell zone structure. mαHER2 treatment group did not show obvious lymphocyte infiltration in the tumors. These data again suggest VSM NanoVax indeed stimulate more TLS, which contributed to its superior anticancer efficacy to other treatments.

Virus-Spike-Mimicry B Cell Nanovaccine (VSM NanoVax) Facilitates Better Lymphatic Homing, Unique B Cell Zone Localization, Efficient Cross-Link of BCR Subsequently, we tested the unique B cell zone localization of VSM NanoVax in the lymph nodes vs. INOP Vax using confocal microscopy. VSM NanoVax was primarily co-localized in the around B cell zone of the lymph nodes, as well as macrophage to a less extent (FIG. 13A). In sharp contrast, INOP Vax did not much co-localization in the B cell zone and also much less in macrophage. Taken together, these data indicate that viral structural mimicry of VSM NanoVax improved lymph node delivery efficiency and preferred B cell zone distribution in the lymph node.

After efficiently homing to the B cell zone of the lymph nodes, the central goal of B cell vaccine is to activate antigen specific B cells. Multivalent cross-link with BCR by the antigens on the virus spike mimicry may greatly enhance B cell activation, which include spike topography, highly localized density of antigen clusters, and optimal distance between clusters (e.g., 5-10 nm). To directly test the cross-link of the antigens in virus spike mimicry in VSM NanoVax vs. INOP Vax, we used the B cells from Quasi-Monoclonal (QM) mouse, majority of whose B cells could specifically bind to hapten (4-hydroxy-3-nitrophenyl) acetyl (hapten-NP) with high affinity. We conjugate this hapten-NP with HER2-epitope so that they could be displayed onto the spiky surface of VSM NanoVax, which was incubated with B cells (1 min) isolated from Quasi-Monoclonal (QM) mouse. Crosslinking of Hapten-NP with BCR was observed under dynamic confocal imaging after staining of BCR. The data showed clear overlap between VSM NanoVax—hapten with BCR in—NP immediately after 1 min incubation, which was gradually accumulated and sustained with increase of as the incubation time. The control group INOP Vax-Hapten showed significant less overlaps with BCR staining (FIG. 13). In addition, to investigate the B cell activation by VSM NanoVax-hapten crosslink with BCR, we also measured calcium flux assay in the B cells from Quasi-Monoclonal (QM) mouse after incubation with VSM NanoVax—hapten vs. INOP Vax—hapten. VSM NanoVax—hapten induced significant higher calcium signaling compared to INOP Vax-Hapten and soluble NP-Hapten (FIG. 13). Finally, to directly confirm the early B cell activation in vivo QM mice by VSM NanoVax-hapten, we immunized QM mice with VSM NanoVax—hapten. 4.5 hours after immunization, VSM NanoVax—hapten showed 6-fold and 40-folder higher B cell early activation than INOPVax—Hapten and soluble HER2-Hapten (FIG. 13).

Virus-Spike-Mimicry B Cell Nanovaccine (VSM NanoVax) Promoted Tfh Dependent B Cell Activation and Enhanced Formation of GC Center.

In order to test the capability of the Virus-Spike-Mimicry B cell Nanovaccine (VSM NanoVax) vs. INOP Vax for Tfh cell dependent B cell activation, we measured antigen (HER2) specific B cells, Germinal Center (GC) B cells, foculicular T helper cells (Tfh), and long-lived plasma cells (PC) in the lymph nodes of vaccinated mice Tetramer assay showed that VSM NanoVax) generated a 3-fold and 14-fold higher Ag specific B cells (10.01%) than INOP Vax i (3.67%), and soluble epitope group (0.7%) in lymph nodes (FIG. 14A). In addition, we also assessed GC formation at 10 days (peak of GC response) after the primary immunization by flow cytometry analysis. VSM NanoVax) resulted in a 2.6-fold and a 8-fold increase in the GC formation in comparison with V. INOP Vax and HER2 peptide immunized groups (FIG. 14B). It is worth noting that the 10.01% Ag specific B cells activation and more than 17% Germinal enter formation are rarely seen by any other cancer vaccine in various delivery systems. These data suggest that the viral spike mimicry of VSM NanoVax) uniquely enhanced Ag-specific B cells in comparison with traditional nanoplatforms. Furthermore, in the germinal center (GC), B cell activation needs the interaction with follicular T cells to generate long lived plasma cells (PC), which produces long-term durable antibody response.

CyTOF Analysis of Immune Cells Reveals that IVLN-HER2 Enhanced Tfh-Dependent B Cell Activation in the Lymph Node In the germinal center (GC), B cell activation needs the interaction with follicular T cells to generate long lived plasma cells (PC), which produces long-term durable antibody response. Therefore, CyTOF analysis was used to evaluate the T cell dependent B cell activation by evaluating immune cells in the lymph nodes after immunization, which include macrophage, dendritic cells, B cell, CD4+, CD8+ T cells, NK cells in the lymph nodes and spleen using 40-makers with heavy medal labeled antibodies.

Global analysis using SPADE showed that IVLN-HER increased GC, plasma B cells, and follicular T cells (FIG. 14 E, F) in the lymph node, but it showed no significance other changes in the immune cells in lymph node and spleen.

Detail analysis revealed that IVLN-HER2 stimulated more germinal center B cells (CD19+/GL7+ or B220+/GL7+) (FIG. 14), T follicular helper cells (Tfh) (CD4+/CXCR5+/PD-1+) (FIG. 14), and plasma cells (PC) (FIG. 14) in comparison with IONP-HER2 immunized group, which is critical for antibody secretion. These data provide strong evidence that IVLN-HER2 induced Tfh-dependent B cell activation in the GC of the lymph nodes, explaining why IVLN-HER2 produced higher tilter antigen-specific antibody.

Virus-Spike-Mimicry B Cell Nanovaccine (VSM NanoVax) Uniquely Remodeled Immune Microenvironment in Tumors by CyTOF Analysis We monitored the tumor immune microenvironment remodeling by the VSM NanoVax in comparison with antibody treatment and T cell (E75) vaccine, through CyTOF. The SPADE analysis of CyTOF data in tumor showed that VSM NanoVax increased 17-fold and 6-fold the B cells, 2-fold and 5-fold Tfh cells, 23-fold and 27-fold CD8$^+$ T cells compared to antibody treatment and T cell vaccines (E75+GM-CSF), respectively (FIG. 15). Then we explored the effect of virus mimicry of VSM NanoVax on tumor microenvironment compared to IONP-HER2 without virus mimicry and soluble HER2 epitope using CyTOF analysis (FIG. 15). SPADE analysis showed that VSM NanoVax increased Tfh cells by 100% and 200%, increased GC B cells by 260% and 30%, CD4+ memory T cells by 80% and 60% compared to IONP-HER2 and soluble HER2 epitope. In addition, SPADE analysis also showed that NanoVax (with LIGHT) dramatically increased GC B cells, Tfh cells, CD4+ and CD8+ memory T cells compared to soluble HER2 epitope (with LIGHT). These data suggest VSM NanoVax with LIGHT showed durable anticancer efficacy through remodeling tumor microenvironment.

Although many T cell cancer vaccines, including HER2 T cell vaccine (E75), have been extensively developed and evaluated, they only achieved limited short term efficacy (1-3 months) with/without combination with anti-PD-1/PD-L1 antibody immunotherapy in both preclinical cancer models and clinical cancer patients, which rarely achieve cancer remission. In contrast, B cell cancer vaccines has not been well studied due either the controversial roles of B cell activation in cancer growth or widely available antibody anticancer therapy. However, most recent studies have revealed that clinical efficacy of anti-PD-1/PD-L1 immunotherapy is highly associated with B cell status and B-rich TLS in tumors. These new discoveries may change the paradigm of cancer vaccine development by altering B and T cell immunity in both lymph nodes and in tumors in combination with anti-PD-1/PD-L1 immunotherapy. Here, we engineered a virus-spike-mimicry B Cell Nanovaccine (VSM NanoVax) using HER2 B and CD4 T cell epitopes, when combined with anti-PD-1/PD-L1 antibody, achieving cancer remission in HER2+ breast cancer (>200 days), which is superior to combination of anti-PD-1/PD-L1 and anti-HER antibodies and clinical used T cells HER2 vaccine (E75+GM-CSF). VSM NanoVax resembled three unique features compared with other nanoparticle delivery system: spiky antigen topography, highly localized antigen cluster density, and optimal distance between Ag clusters. These features of VSM NanoVax improved its lymph nodes homing and displayed a unique B cell zone localization in the lymph nodes compared to other nanoparticles without virus like feature. In addition, the virus spike mimicry of VSM NanoVax also more efficiently crosslink with BCR and activated B cells in vitro and in vivo compared to nanoparticle delivery without virus spike mimicry. In the lymph nodes, VSM NanoVax increased antigens (HER2) specific B cell, GC B cells, Tfh cells compared to standard nanoparticle antigens delivery as measured by flow cytometry and CyTOF. VSM NanoVax also enhanced antibody production by 8 fold compared to nano particle delivery system without virus like feature. In the tumors, VSM NanoVax promoted formation of B cell rich TLS. Single cell RNA-seq and CyTOF revealed that VSM NanoVax increased tumor infiltration B/T cells, specifically increased GC B cells, Tfh cells, memory B/T cells and plasma cells in tumors. VSM NanoVax also promote the TLS formation in tumor by increasing, the VEGFC for HEV genesis, the addressins for lymphocytes trafficking and the chemotaxis factors for lymphocytes recruitment and TLS structure organization. These data suggest that virus spike mimicry B cell Nanovaccine (VSM NanoVax) using HER2 B and CD4 T cell epitopes, combined with anti-PD-1/PD-L1 antibody, should achieve durable anticancer efficacy and long term remission by stimulating Tfh cell-dependent B cell activation in the lymph nodes and B cell-rich TLS formation in the tumors.

REFERENCES

1. B. D. Hill, A. Zak, E. Khera, F. Wen, Engineering Virus-like Particles for Antigen and Drug Delivery. Curr Protein Pept Sci 19, 112-127 (2018).
2. E. M. Plummer, M. Manchester, Viral nanoparticles and virus-like particles: platforms for contemporary vaccine design. Wiley Interdiscip Rev Nanomed Nanobiotechnol 3, 174-196 (2011).
3. J. K. Pokorski, N. F. Steinmetz, The art of engineering viral nanoparticles. Mol Pharm 8, 29-43 (2011).
4. A. Zeltins, Construction and characterization of virus-like particles: a review. Mol Biotechnol 53, 92-107 (2013).
5. P. Roy, R. Noad, Virus-like particles as a vaccine delivery system: myths and facts. Hum Vaccin 4, 5-12 (2008).
6. M. G. Masavuli, D. K. Wijesundara, J. Torresi, E. J. Gowans, B. Grubor-Bauk, Preclinical Development and Production of Virus-Like Particles As Vaccine Candidates for Hepatitis C. Front Microbiol 8, (2017).
7. J. W. Wang, R. B. S. Roden, Virus-like particles for the prevention of human papillomavirus-associated malignancies. Expert Review of Vaccines 12, 129-141 (2013).
8. W. A. Rodriguez-Limas, K. Sekar, K. E. J. Tyo, Virus-like particles: the future of microbial factories and cell-free systems as platforms for vaccine development. Curr. Opin. Biotechnol. 24, 1089-1093 (2013).
9. W. Cheng, The Density Code for the Development of a Vaccine? J Pharm Sci 105, 3223-3232 (2016).
10. S. K. Pierce, W. Liu, The tipping points in the initiation of B cell signalling: how small changes make big differences. Nat Rev Immunol 10, 767-777 (2010).
11. S. E. Olsson et al., Induction of immune memory following administration of a prophylactic quadrivalent human papillomavirus (HPV) types 6/11/16/18 L1 virus-like particle (VLP) vaccine. Vaccine 25, 4931-4939 (2007).
12. L. Shi et al., GARDASIL: prophylactic human papillomavirus vaccine development—from bench top to bedside. Clin Pharmacol Ther 81, 259-264 (2007).
13. J. T. Schiller, D. R. Lowy, Understanding and learning from the success of prophylactic human papillomavirus vaccines. Nat Rev Microbiol 10, 681-692 (2012).
14. B. Chackerian, D. R. Lowy, J. T. Schiller, Conjugation of a self-antigen to papillomavirus-like particles allows for efficient induction of protective autoantibodies. J. Clin. Invest. 108, 415-423 (2001).

15. A. Roldao, M. C. Mellado, L. R. Castilho, M. J. Carrondo, P. M. Alves, Virus-like particles in vaccine development. Expert Rev Vaccines 9, 1149-1176 (2010).
16. L. J. Chang et al., Safety and tolerability of chikungunya virus-like particle vaccine in healthy adults: a phase 1 dose-escalation trial. Lancet 384, 2046-2052 (2014).
17. J. J. Treanor et al., A novel intramuscular bivalent norovirus virus-like particle vaccine candidate—reactogenicity, safety, and immunogenicity in a phase 1 trial in healthy adults. J Infect Dis 210, 1763-1771 (2014).
18. N. Landry et al., Preclinical and clinical development of plant-made virus-like particle vaccine against avian H5N1 influenza. PLoS One 5, e15559 (2010).
19. M. O. Mohsen, L. Zha, G. Cabral-Miranda, M. F. Bachmann, Major findings and recent advances in virus-like particle (VLP)-based vaccines. Semin Immunol 34, 123-132 (2017).
20. L. M. Zarebski et al., Analysis of epitope information related to *Bacillus anthracis* and *Clostridium botulinum*. Expert Rev Vaccines 7, 55-74 (2008).
21. S. R. Crowe et al., Select human anthrax protective antigen epitope-specific antibodies provide protection from lethal toxin challenge. J Infect Dis 202, 251-260 (2010).
22. M. L. Nguyen et al., Sequential B-cell epitopes of *Bacillus anthracis* lethal factor bind lethal toxin-neutralizing antibodies. Infect Immun 77, 162-169 (2009).
23. T. Bekaii-Saab et al., Phase I Immunotherapy Trial with Two Chimeric HER-2 B-Cell Peptide Vaccines Emulsified in Montanide ISA 720VG and Nor-MDP Adjuvant in Patients with Advanced Solid Tumors. Clin Cancer Res 25, 3495-3507 (2019).
24. H. Miyako et al., Antitumor effect of new HER2 peptide vaccination based on B cell epitope. Anticancer Res 31, 3361-3368 (2011).
25. B. S. Lee, J. S. Huang, L. P. Jayathilaka, J. Lee, S. Gupta, Antibody Production with Synthetic Peptides. Methods Mol Biol 1474, 25-47 (2016).
26. J. Fuenmayor, F. Godia, L. Cervera, Production of virus-like particles for vaccines. New Biotechnol 39, 174-180 (2017).
27. L. A. Palomares, O. T. Ramirez, Challenges for the production of virus-like particles in insect cells: The case of rotavirus-like particles. Biochem Eng J 45, 158-167 (2009).
28. M. J. McCluskie et al., The effect of preexisting anti-carrier immunity on subsequent responses to CRM197 or Qb-VLP conjugate vaccines. Immunopharmacol Immunotoxicol 38, 184-196 (2016).
29. A. Jegerlehner et al., Carrier induced epitopic suppression of antibody responses induced by virus-like particles is a dynamic phenomenon caused by carrier-specific antibodies. Vaccine 28, 5503-5512 (2010).
30. A. Palladini et al., Virus-like particle display of HER2 induces potent anti-cancer responses. Oncoimmunology 7, e1408749 (2018).
31. S. Chattopadhyay, J. Y. Chen, H. W. Chen, C. J. Hu, Nanoparticle Vaccines Adopting Virus-like Features for Enhanced Immune Potentiation. Nanotheranostics 1, 244-260 (2017).
32. M. F. Bachmann, G. T. Jennings, Vaccine delivery: a matter of size, geometry, kinetics and molecular patterns. Nat Rev Immunol 10, 787-796 (2010).
33. G. Spohn, M. F. Bachmann, Exploiting viral properties for the rational design of modern vaccines. Expert Rev Vaccines 7, 43-54 (2008).
34. M. Somiya, Q. Liu, S. Kuroda, Current Progress of Virus-mimicking Nanocarriers for Drug Delivery. Nanotheranostics 1, 415-429 (2017).
35. C. Lee et al., Rabies Virus-Inspired Silica-Coated Gold Nanorods as a Photothermal Therapeutic Platform for Treating Brain Tumors. Adv Mater 29, (2017).
36. C. Lee et al., Virus-mimetic polymer nanoparticles displaying hemagglutinin as an adjuvant-free influenza vaccine. Biomaterials 183, 234-242 (2018).
37. J. Ingale et al., High-Density Array of Well-Ordered HIV-1 Spikes on Synthetic Liposomal Nanoparticles Efficiently Activate B Cells. Cell Rep 15, 1986-1999 (2016).
38. V. Riitho et al., Design and evaluation of the immunogenicity and efficacy of a biomimetic particulate formulation of viral antigens. Sci Rep 7, 13743 (2017).
39. W. Cheng, The Density Code for the Development of a Vaccine? J. Pharm. Sci. 105, 3223-3232 (2016).
40. M. F. Bachmann et al., The influence of antigen organization on B cell responsiveness. Science 262, 1448-1451 (1993).
41. H. J. Hinton, A. Jegerlehner, M. F. Bachmann, Pattern recognition by B cells: the role of antigen repetitiveness versus Toll-like receptors. Curr Top Microbiol Immunol 319, 1-15 (2008).
42. S. A. Oracki, J. A. Walker, M. L. Hibbs, L. M. Corcoran, D. M. Tarlinton, Plasma cell development and survival. Immunol Rev 237, 140-159 (2010).
43. K. A. Pape, J. J. Taylor, R. W. Maul, P. J. Gearhart, M. K. Jenkins, in Science. (2011), vol. 331, pp. 1203-1207.
44. M. McHeyzer-Williams, S. Okitsu, N. Wang, L. McHeyzer-Williams, Molecular programming of B cell memory. Nat Rev Immunol 12, 24-34 (2012).
45. R. Brink, T. G. Phan, D. Paus, T. D. Chan, Visualizing the effects of antigen affinity on T-dependent B-cell differentiation. Immunol Cell Biol 86, 31-39 (2008).
46. L. J. McHeyzer-Williams, M. G. McHeyzer-Williams, Antigen-specific memory B cell development. Annu Rev Immunol 23, 487-513 (2005).
47. P. D. Minor, Live attenuated vaccines: Historical successes and current challenges. Virology 479-480, 379-392 (2015).
48. L. A. VanBlargan, L. Goo, T. C. Pierson, Deconstructing the Antiviral Neutralizing-Antibody Response: Implications for Vaccine Development and Immunity. Microbiol Mol Biol Rev 80, 989-1010 (2016).
49. N. Nayerossadat, T. Maedeh, P. A. Ali, Viral and nonviral delivery systems for gene delivery. Adv Biomed Res 1, 27 (2012).
50. Y. S. Tan et al., Mitigating SOX2-potentiated Immune Escape of Head and Neck Squamous Cell Carcinoma with a STING-inducing Nanosatellite Vaccine. Clin Cancer Res 24, 4242-4255 (2018).
51. H. W. Chen et al., Facile Fabrication of Near-Infrared-Resonant and Magnetic Resonance Imaging-Capable Nanomediators for Photothermal Therapy. Acs Appl Mater Inter 7, 12814-12823 (2015).
52. H. W. Chen et al., Highly crystallized iron oxide nanoparticles as effective and biodegradable mediators for photothermal cancer therapy. J Mater Chem B 2, 757-765 (2014).
53. A. M. Gobin, E. M. Watkins, E. Quevedo, V. L. Colvin, J. L. West, Near-infrared-resonant gold/gold sulfide nanoparticles as a photothermal cancer therapeutic agent. Small 6, 745-752 (2010).

54. Y. Lu, L. Wang, D. Chen, G. Wang, Determination of the concentration and the average number of gold atoms in a gold nanoparticle by osmotic pressure. Langmuir 28, 9282-9287 (2012).
55. M. Kokate, K. Garadkar, A. Gole, One pot synthesis of magnetite-silica nanocomposites: applications as tags, entrapment matrix and in water purification. J Mater Chem A 1, 2022-2029 (2013).
56. J. Rockberg, J. M. Schwenk, M. Uhlen, Discovery of epitopes for targeting the human epidermal growth factor receptor 2 (HER2) with antibodies. Mol Oncol 3, 238-247 (2009).
57. S. Shukla, A. M. Wen, U. Commandeur, N. F. Steinmetz, Presentation of HER2 epitopes using a filamentous plant virus-based vaccination platform. J Mater Chem B 2, 6249-6258 (2014).
58. J. Jasinska et al., Inhibition of tumor cell growth by antibodies induced after vaccination with peptides derived from the extracellular domain of Her-2/neu. Int J Cancer 107, 976-983 (2003).
59. S. K. Pierce, W. L. Liu, The tipping points in the initiation of B cell signalling: how small changes make big differences. Nat Rev Immunol 10, 767-777 (2010).
60. C. Balmelli et al., Nasal immunization of mice with human papillomavirus type 16 virus-like particles elicits neutralizing antibodies in mucosal secretions. J Virol 72, 8220-8229 (1998).
61. H. Elsayed et al., Intrastructural Help: Harnessing T Helper Cells Induced by Licensed Vaccines for Improvement of HIV Env Antibody Responses to Virus-Like Particle Vaccines. J Virol 92, (2018).
62. Y. T. Lee et al., Intranasal vaccination with M2e5x virus-like particles induces humoral and cellular immune responses conferring cross-protection against heterosubtypic influenza viruses. PLoS One 13, e0190868 (2018).
63. B. Franz, K. F. May, Jr., G. Dranoff, K. Wucherpfennig, Ex vivo characterization and isolation of rare memory B cells with antigen tetramers. Blood 118, 348-357 (2011).
64. M. N. E. Forsell, L. Kvastad, S. K. Sedimbi, J. Andersson, M. C. I. Karlsson, Regulation of Subunit-Specific Germinal Center B Cell Responses to the HIV-1 Envelope Glycoproteins by Antibody-Mediated Feedback. Front Immunol 8, 738 (2017).
65. C. Chen et al., Uhrf1 regulates germinal center B cell expansion and affinity maturation to control viral infection. J Exp Med 215, 1437-1448 (2018).
66. L. Galluzzi, T. Yamazaki, S. Demaria, Heavy Metal to Rock the Immune Infiltrate. Trends Immunol 38, 539-541 (2017).
67. S. Chevrier et al., An Immune Atlas of Clear Cell Renal Cell Carcinoma. Cell 169, 736-749 e718 (2017).
68. Y. Lavin et al., Innate Immune Landscape in Early Lung Adenocarcinoma by Paired Single-Cell Analyses. Cell 169, 750-765 e717 (2017).
69. H. H. Tam et al., Sustained antigen availability during germinal center initiation enhances antibody responses to vaccination. Proc Natl Acad Sci USA 113, E6639-E6648 (2016).
70. R. Cubas et al., Virus-like particle (VLP) lymphatic trafficking and immune response generation after immunization by different routes. J Immunother 32, 118-128 (2009).
71. N. S. De Silva, U. Klein, Dynamics of B cells in germinal centres. Nat Rev Immunol 15, 137-148 (2015).
72. Y. R. Carrasco, F. D. Batista, B cells acquire particulate antigen in a macrophage-rich area at the boundary between the follicle and the subcapsular sinus of the lymph node. Immunity 27, 160-171 (2007).
73. M. O. Mohsen, A. C. Gomes, M. Vogel, M. F. Bachmann, Interaction of Viral Capsid-Derived Virus-Like Particles (VLPs) with the Innate Immune System. Vaccines (Basel) 6, (2018).
74. C. P. Loo et al., Lymphatic Vessels Balance Viral Dissemination and Immune Activation following Cutaneous Viral Infection. Cell Rep 20, 3176-3187 (2017).
75. T. Junt et al., Subcapsular sinus macrophages in lymph nodes clear lymph-borne viruses and present them to antiviral B cells. Nature 450, 110-114 (2007).
76. M. Kuka, M. Iannacone, The role of lymph node sinus macrophages in host defense. Ann N Y Acad Sci 1319, 38-46 (2014).
77. B. Chertok, A. J. Cole, A. E. David, V. C. Yang, Comparison of electron spin resonance spectroscopy and inductively-coupled plasma optical emission spectroscopy for biodistribution analysis of iron-oxide nanoparticles. Mol Pharm 7, 375-385 (2010).
78. R. M. Clauson, M. Chen, L. M. Scheetz, B. Berg, B. Chertok, Size-Controlled Iron Oxide Nanoplatforms with Lipidoid-Stabilized Shells for Efficient Magnetic Resonance Imaging-Trackable Lymph Node Targeting and High-Capacity Biomolecule Display. ACS Appl Mater Interfaces 10, 20281-20295 (2018).
79. T. Kamala, Hock immunization: a humane alternative to mouse footpad injections. J Immunol Methods 328, 204-214 (2007).
80. E. E. Gray, J. G. Cyster, Lymph node macrophages. J Innate Immun 4, 424-436 (2012).
81. A. Ocana, E. Amir, A. Pandiella, Dual targeting of HER2-positive breast cancer with trastuzumab emtansine and pertuzumab: understanding clinical trial results. Oncotarget 9, 31915-31919 (2018).
82. S. M. Swain et al., Pertuzumab, trastuzumab, and docetaxel in HER2-positive metastatic breast cancer. N Engl J Med 372, 724-734 (2015).
83. P. J. Whittington et al., Her-2 DNA versus cell vaccine: immunogenicity and anti-tumor activity. Cancer Immunol Immunother 58, 759-767 (2009).
84. S. Tong, S. Hou, B. Ren, Z. Zheng, G. Bao, Self-assembly of phospholipid-PEG coating on nanoparticles through dual solvent exchange. Nano Lett 11, 3720-3726 (2011).
85. E. V. Shtykova et al., Structure and properties of iron oxide nanoparticles encapsulated by phospholipids with poly(ethylene glycol) tails. J Phys Chem C 111, 18078-18086 (2007).
86. S. Udenfriend et al., Fluorescamine: a reagent for assay of amino acids, peptides, proteins, and primary amines in the picomole range. Science 178, 871-872 (1972).
87. A. B. Sanchez et al., A general process for the development of peptide-based immunoassays for monoclonal antibodies. Cancer Chemother Pharmacol 66, 919-925 (2010).
88. A. M. van Loon, J. van der Veen, Enzyme-linked immunosorbent assay for quantitation of toxoplasma antibodies in human sera. J Clin Pathol 33, 635-639 (1980).
89. M. Mingueneau et al., Single-cell mass cytometry of TCR signaling: Amplification of small initial differences results in low ERK activation in NOD mice. P Natl Acad Sci USA 111, 16466-16471 (2014).
90. A. C. Billi et al., The female-biased factor VGLL3 drives cutaneous and systemic autoimmunity. JCI Insight 4, (2019).

91. Lu, T. T. & Browning, J. L. Role of the Lymphotoxin/ LIGHT System in the Development and Maintenance of Reticular Networks and Vasculature in Lymphoid Tissues.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A composition comprising: a nano-satellite complex, wherein said nano-satellite complex surface has a negative charge, and wherein said nano-satellite complex comprises:
    a) a core nanoparticle complex comprising a biocompatible coating surrounding a nanoparticle core;
    b) 10-20 gold satellite particles attached to, or absorbed to, said biocompatible coating;
    c) a plurality of antigenic peptides conjugated to, or absorbed to, said satellite particles; and
    d) wherein said nano-satellite complex comprises all of the following properties:
        i) wherein the weight-to-weight ratio of all of said satellite particles to said nanoparticle core is 10-40%;
        ii) wherein the diameter of each of said satellite particles is 1-5 nm, and the diameter of the nano-satellite complex is 20-70 nm;
        iii) wherein said plurality of antigenic peptides is 1500-2500 antigenic peptides;
        iv) wherein 100-225 of said plurality of said antigenic peptides are present on each of said satellite particles; and
        v) wherein the average distance between each of said satellite particles is 4-7 nm.

2. The composition of claim 1, further comprising an immune checkpoint inhibitor.

3. The composition of claim 1, wherein said core nanoparticle comprises $Fe_3O_4$.

4. The composition of claim 1, wherein said biocompatible coating comprises polysiloxane.

5. The composition of claim 1, wherein said antigenic peptide comprises: i) a neoantigenic determinant, ii) at least one epitope from a tumor antigen, iii) at least one epitope from a viral oncoprotein, iv) a least one epitope from an infectious virus, v) at least one epitope from a parasite, or vi) at least one epitope from an infectious bacteria.

6. A method of eliciting an immune response in a subject comprising: administering to a subject said composition of claim 1.

7. The method of claim 6, wherein said subject is a human.

8. The method of claim 6, wherein said subject is administered a type I interferon agonist agent, either in said composition or separately.

9. The method of claim 6, wherein said subject is administered an immune checkpoint inhibitor, either in said composition or separately.

* * * * *

```
                         SEQUENCE LISTING

<160> NUMBER OF SEQ ID NOS: 18

<210> SEQ ID NO 1
<211> LENGTH: 25
<212> TYPE: PRT
<213> ORGANISM: Artificial sequence
<220> FEATURE:
<223> OTHER INFORMATION: Synthetic HER2 peptide

<400> SEQUENCE: 1

Cys Asp Asp Asp Pro Glu Ser Phe Asp Gly Asp Pro Ala Ser Asn Thr
1               5                   10                  15

Ala Pro Leu Gln Pro Glu Gln Leu Gln
            20                  25

<210> SEQ ID NO 2
<211> LENGTH: 21
<212> TYPE: PRT
<213> ORGANISM: Artificial sequence
<220> FEATURE:
<223> OTHER INFORMATION: Synthetic HER2 peptide

<400> SEQUENCE: 2

Pro Glu Ser Phe Asp Gly Asp Pro Ala Ser Asn Thr Ala Pro Leu Gln
1               5                   10                  15

Pro Glu Gln Leu Gln
            20

<210> SEQ ID NO 3
<211> LENGTH: 29
<212> TYPE: PRT
<213> ORGANISM: Artificial sequence
<220> FEATURE:
<223> OTHER INFORMATION: Synthetic HER2 peptide

<400> SEQUENCE: 3

Cys Asp Asp Asp Pro Glu Ser Phe Asp Gly Asp Pro Ala Ser Asn Thr
1               5                   10                  15

Ala Pro Leu Gln Pro Glu Gln Leu Gln Gly Gly Gly Lys
            20                  25

<210> SEQ ID NO 4
<211> LENGTH: 1255
<212> TYPE: PRT
<213> ORGANISM: Homo sapiens

<400> SEQUENCE: 4

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
```

```
            50                  55                  60
Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
            130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
            370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480
```

```
Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
        500                 505                 510

Gln Leu Cys Ala Arg Gly His Cys Trp Gly Pro Gly Pro Thr Gln Cys
    515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
        580                 585                 590

Pro Pro Phe Cys Val Ala Arg Cys Pro Ser Gly Val Lys Pro Asp Leu
    595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
            645                 650                 655

Ala Val Val Gly Ile Leu Leu Val Val Leu Gly Val Val Phe Gly
        660                 665                 670

Ile Leu Ile Lys Arg Arg Gln Gln Lys Ile Arg Lys Tyr Thr Met Arg
    675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
            725                 730                 735

Gly Ile Trp Ile Pro Asp Gly Glu Asn Val Lys Ile Pro Val Ala Ile
        740                 745                 750

Lys Val Leu Arg Glu Asn Thr Ser Pro Lys Ala Asn Lys Glu Ile Leu
    755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
        820                 825                 830

Met Ser Tyr Leu Glu Asp Val Arg Leu Val His Arg Asp Leu Ala Ala
    835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
            885                 890                 895
```

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
        930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 5
<211> LENGTH: 240
<212> TYPE: PRT
<213> ORGANISM: Homo sapiens

<400> SEQUENCE: 5

```
Met Glu Glu Ser Val Val Arg Pro Ser Val Phe Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Met Gly
            35                  40                  45

Ala Gly Leu Ala Val Gln Gly Trp Phe Leu Leu Gln Leu His Trp Arg
50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
            115                 120                 125

His Asp Gly Ala Leu Val Val Thr Lys Ala Gly Tyr Tyr Tyr Ile Tyr
            130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
            165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
            195                 200                 205

Leu Glu Ala Gly Glu Lys Val Val Val Arg Val Leu Asp Glu Arg Leu
210                 215                 220

Val Arg Leu Arg Asp Gly Thr Arg Ser Tyr Phe Gly Ala Phe Met Val
225                 230                 235                 240

<210> SEQ ID NO 6
<211> LENGTH: 120
<212> TYPE: PRT
<213> ORGANISM: Mus musculus

<400> SEQUENCE: 6

Glu Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
            35                  40                  45

Gly Arg Ile Tyr Pro Thr Asn Gly Tyr Thr Arg Tyr Asp Pro Lys Phe
50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Ala Ser Val Thr Val Ser Ser
            115                 120
```

<210> SEQ ID NO 7
<211> LENGTH: 330
<212> TYPE: PRT
<213> ORGANISM: Mus musculus

<400> SEQUENCE: 7

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 8
<211> LENGTH: 107
<212> TYPE: PRT
<213> ORGANISM: Mus musculus

<400> SEQUENCE: 8

Asp Ile Val Met Thr Gln Ser His Lys Phe Met Ser Thr Ser Val Gly

-continued

```
              1               5                  10                 15
            Asp Arg Val Ser Ile Thr Cys Lys Ala Ser Gln Asp Val Asn Thr Ala
                            20                  25                 30

Val Ala Trp Tyr Gln Gln Lys Pro Gly His Ser Pro Lys Leu Leu Ile
                        35                  40                 45

Tyr Ser Ala Ser Phe Arg Tyr Thr Gly Val Pro Asp Arg Phe Thr Gly
                    50                  55                 60

Asn Arg Ser Gly Thr Asp Phe Thr Phe Thr Ile Ser Ser Val Gln Ala
             65                 70                  75                 80

Glu Asp Leu Ala Val Tyr Tyr Cys Gln Gln His Tyr Thr Thr Pro Pro
                            85                  90                 95

Thr Phe Gly Gly Gly Thr Lys Leu Glu Ile Lys
                            100                 105

<210> SEQ ID NO 9
<211> LENGTH: 107
<212> TYPE: PRT
<213> ORGANISM: Mus musculus

<400> SEQUENCE: 9

Arg Ala Asp Ala Ala Pro Thr Val Ser Ile Phe Pro Pro Ser Ser Glu
             1               5                  10                 15

Gln Leu Thr Ser Gly Gly Ala Ser Val Val Cys Phe Leu Asn Asn Phe
                            20                  25                 30

Tyr Pro Lys Asp Ile Asn Val Lys Trp Lys Ile Asp Gly Ser Glu Arg
                        35                  40                 45

Gln Asn Gly Val Leu Asn Ser Trp Thr Asp Gln Asp Ser Lys Asp Ser
                    50                  55                 60

Thr Tyr Ser Met Ser Ser Thr Leu Thr Leu Thr Lys Asp Glu Tyr Glu
             65                 70                  75                 80

Arg His Asn Ser Tyr Thr Cys Glu Ala Thr His Lys Thr Ser Thr Ser
                            85                  90                 95

Pro Ile Val Lys Ser Phe Asn Arg Asn Glu Cys
                            100                 105

<210> SEQ ID NO 10
<211> LENGTH: 119
<212> TYPE: PRT
<213> ORGANISM: Mus musculus

<400> SEQUENCE: 10

Glu Val Gln Leu Gln Gln Ser Gly Pro Glu Leu Val Lys Pro Gly Thr
             1               5                  10                 15

Ser Val Lys Ile Ser Cys Lys Ala Ser Gly Phe Thr Phe Thr Asp Tyr
                            20                  25                 30

Thr Met Asp Trp Val Lys Gln Ser His Gly Lys Ser Leu Glu Trp Ile
                        35                  40                 45

Gly Asp Val Asn Pro Asn Ser Gly Gly Ser Ile Tyr Asn Gln Arg Phe
                    50                  55                 60

Lys Gly Lys Ala Ser Leu Thr Val Asp Arg Ser Ser Arg Ile Val Tyr
             65                 70                  75                 80

Met Glu Leu Arg Ser Leu Thr Phe Glu Asp Thr Ala Val Tyr Tyr Cys
                            85                  90                 95

Ala Arg Asn Leu Gly Pro Ser Phe Tyr Phe Asp Tyr Trp Gly Gln Gly
                            100                 105                110

Thr Thr Leu Thr Val Ser Ser
```

<210> SEQ ID NO 11
<211> LENGTH: 330
<212> TYPE: PRT
<213> ORGANISM: Mus musculus

<400> SEQUENCE: 11

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
    275                 280                 285

Met Tyr Ser Lys Leu Arg Val Glu Lys Lys Asn Trp Val Glu Arg Asn
290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
            325                 330

<210> SEQ ID NO 12
<211> LENGTH: 107
<212> TYPE: PRT
<213> ORGANISM: Mus musculus

```
<400> SEQUENCE: 12

Asp Thr Val Met Thr Gln Ser His Lys Ile Met Ser Thr Ser Val Gly
1               5                   10                  15

Asp Arg Val Ser Ile Thr Cys Lys Ala Ser Gln Asp Val Ser Ile Gly
            20                  25                  30

Val Ala Trp Tyr Gln Gln Arg Pro Gly Gln Ser Pro Lys Leu Leu Ile
        35                  40                  45

Tyr Ser Ala Ser Tyr Arg Tyr Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Tyr Tyr Ile Tyr Pro Tyr
                85                  90                  95

Thr Phe Gly Gly Gly Thr Lys Leu Glu Ile Lys
            100                 105

<210> SEQ ID NO 13
<211> LENGTH: 107
<212> TYPE: PRT
<213> ORGANISM: Mus musculus

<400> SEQUENCE: 13

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 14
<211> LENGTH: 29
<212> TYPE: PRT
<213> ORGANISM: Artificial sequence
<220> FEATURE:
<223> OTHER INFORMATION: Synthetic HER2 peptide

<400> SEQUENCE: 14

Cys Asp Asp Asp Pro Glu Ser Phe Asp Gly Asp Pro Ala Ser Asn Thr
1               5                   10                  15

Ala Pro Leu Gln Pro Glu Gln Leu Gln Gly Gly Gly Lys
            20                  25

<210> SEQ ID NO 15
<211> LENGTH: 29
<212> TYPE: PRT
<213> ORGANISM: Artificial sequence
<220> FEATURE:
<223> OTHER INFORMATION: Synthetic HER2 peptide

<400> SEQUENCE: 15

Asp Asp Asp Pro Glu Ser Phe Asp Gly Asp Pro Ala Ser Asn Thr Ala
```

```
1               5                  10                 15
Pro Leu Gln Pro Glu Gln Leu Gln Lys Gly Gly Gly Lys
            20                 25

<210> SEQ ID NO 16
<211> LENGTH: 27
<212> TYPE: PRT
<213> ORGANISM: Artificial sequence
<220> FEATURE:
<223> OTHER INFORMATION: Synthetic HER2 peptide

<400> SEQUENCE: 16

Cys Asp Asp Pro Glu Ser Phe Asp Gly Asp Pro Ala Ser Asn Thr
1               5                  10                 15

Ala Pro Leu Gln Pro Glu Gln Leu Gln Glu Asp
            20                 25

<210> SEQ ID NO 17
<211> LENGTH: 13
<212> TYPE: PRT
<213> ORGANISM: Artificial sequence
<220> FEATURE:
<223> OTHER INFORMATION: Synthetic HER2 peptide

<400> SEQUENCE: 17

Cys Asp Asp Lys Ile Phe Gly Ser Leu Ala Phe Leu
1               5                  10

<210> SEQ ID NO 18
<211> LENGTH: 9
<212> TYPE: PRT
<213> ORGANISM: Artificial sequence
<220> FEATURE:
<223> OTHER INFORMATION: Synthetic HER2 peptide

<400> SEQUENCE: 18

Lys Ile Phe Gly Ser Leu Ala Phe Leu
1               5
```